United States Patent
Pastor Fernández et al.

(10) Patent No.: US 9,073,927 B2
(45) Date of Patent: Jul. 7, 2015

(54) INHIBITORS OF PI3 KINASE

(75) Inventors: Joaquin Pastor Fernández, Madrid (ES); Sonia Martinez Gonzalez, Madrid (ES); Rosa Maria Álvarez Escobar, Madrid (ES); Antonio Rodriguez Hergueta, Madrid (ES); Jose Ignacio Martin Hernando, Madrid (ES); Francisco Javier Ramos Lima, Madrid (ES)

(73) Assignee: FUNDACION CENTRO NACIONAL DE INVESTIGACIONES ONCOLOGICAS CARLOS III, Madrid (ES)

( * ) Notice: Subject to any disclaimer, the term of this patent is extended or adjusted under 35 U.S.C. 154(b) by 107 days.

(21) Appl. No.: 13/574,018

(22) PCT Filed: Jan. 24, 2011

(86) PCT No.: PCT/GB2011/000086
§ 371 (c)(1),
(2), (4) Date: Nov. 8, 2012

(87) PCT Pub. No.: WO2011/089400
PCT Pub. Date: Jul. 28, 2011

(65) Prior Publication Data
US 2013/0053371 A1    Feb. 28, 2013

(30) Foreign Application Priority Data
Jan. 22, 2010   (EP) ..................................... 10380012

(51) Int. Cl.
*A61K 31/5377* (2006.01)
*C07D 413/14* (2006.01)
*C07D 487/04* (2006.01)

(52) U.S. Cl.
CPC .......... *C07D 487/04* (2013.01); *A61K 31/5377* (2013.01); *C07D 413/14* (2013.01)

(58) Field of Classification Search
CPC .................... A61K 31/5377; C07D 413/14
USPC ......................................... 544/117; 514/233.2
See application file for complete search history.

(56) References Cited

U.S. PATENT DOCUMENTS

| | | | |
|---|---|---|---|
| 3,995,039 A | 11/1976 | Rooney et al. | |
| 4,478,835 A | 10/1984 | Wade | |
| 4,814,470 A | 3/1989 | Colin et al. | |
| 5,438,072 A | 8/1995 | Bobee et al. | |
| 5,698,582 A | 12/1997 | Bastart et al. | |
| 5,714,512 A | 2/1998 | Bastart et al. | |
| 5,750,561 A | 5/1998 | Bastart et al. | |
| 6,713,485 B2 | 3/2004 | Carter et al. | |
| 6,727,256 B1 | 4/2004 | Carter et al. | |
| 6,933,299 B1 | 8/2005 | Cokerill et al. | |
| 6,960,614 B2 | 11/2005 | Barrett et al. | |
| 6,972,298 B2 | 12/2005 | Baragi et al. | |
| 7,084,147 B2 | 8/2006 | Cokerill et al. | |
| 7,109,333 B2 | 9/2006 | Carter et al. | |
| 7,141,576 B2 | 11/2006 | Lackey et al. | |

(Continued)

FOREIGN PATENT DOCUMENTS

| | | |
|---|---|---|
| DE | 2 424 334 A1 | 12/1974 |
| FR | 2662163 A1 | 11/1991 |

(Continued)

OTHER PUBLICATIONS

Abdel-Magid, A. F. et al., "Reductive Amination of Aldehydes and Ketones with Weakly Basic Anilines Using Sodium Triacetoxyborohydride." Synthesis Letters, (1990), pp. 537-539.

Abdel-Magid. A. F. et al., Reductive Amination of Aldehydes and Ketones J. Org. Chem. (1996), vol. 61, pp. 3849-3862.

Abignente, E. et al., "Research on Heterocyclic compounds, XXVII. Synthesis and Antinflammatory Activity of 2-Phenlimidazo(1,2b]Pyridazine-3-Carboxylic Acids", IL Farmaco (1990), vol. 45, pp. 1075-1087.

Andanappa K. Gadad et al., Synthesis and anti-tubercular activity of a series of 2-sulfonamido/trifluoromethyl-6-substituted imidaxol-[2,1-6]-1,34-thiadiazole derivatives Biorganic & Medicinal Chemistry (2004), vol. 12, pp. 5651-5659.

Asunción Marín et al., Synthesis and Anthelmintic Activity of Carbamates Derived from Imidazo[2,1-b][1,3,4] Thiadiazole and Imidazo[2,1-b]Thiazole(*), Farmaco, (1992), vol. 47 (1), pp. 63-75.

Bellamy, F.D. et al., "Selective Reduction of Aromatic Nitro Compounds with Stannous Chloride in Non Acidic and Non Aqueous Medium", Tetrahedron Letters (1984), vol. 25, No. 8, pp. 839-842.

(Continued)

*Primary Examiner* — Rebecca Anderson
(74) *Attorney, Agent, or Firm* — McCarter & English, LLP; Steven G. Davis; Wei Song

(57) ABSTRACT

There is provided compounds of formula (I), wherein $A_1$, $A_4$, $A_{4a}$, $A_5$, $B^1$, $B^{1a}$, $B^2$, $B^{2a}$, $B^3$, $B^{3a}$, $B^4$, $B^{4a}$ and $R^3$ have meanings given in the description, and pharmaceutically-acceptable esters, amides, solvates or salts thereof, which compounds are useful in the treatment of diseases in which inhibition of a protein or lipid kinase (e.g. a PI3-K and/or mTOR) is desired and/or required, and particularly in the treatment of cancer or a proliferative disease.

(I)

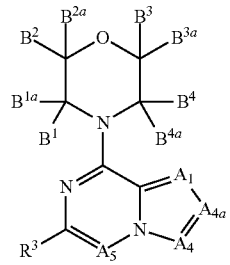

15 Claims, No Drawings

(56) References Cited

U.S. PATENT DOCUMENTS

| | | |
|---|---|---|
| 7,157,466 B2 | 1/2007 | McClure et al. |
| 2004/0147478 A1 | 7/2004 | Merriman |
| 2005/0085550 A1 | 4/2005 | Macikenas et al. |
| 2006/0084650 A1 | 4/2006 | Dong et al. |
| 2007/0078136 A1 | 4/2007 | Vaccaro et al. |
| 2008/0045536 A1 | 2/2008 | Vaccaro et al. |
| 2009/0163489 A1 | 6/2009 | Booker et al. |

FOREIGN PATENT DOCUMENTS

| | | |
|---|---|---|
| FR | 26661163 A1 | 11/1991 |
| JP | 2005/089352 A | 4/2005 |
| WO | WO-01/23389 A2 | 4/2001 |
| WO | WO-02/060492 A1 | 8/2002 |
| WO | 03/000693 A1 | 1/2003 |
| WO | 03/044021 A2 | 5/2003 |
| WO | 2004/005290 A1 | 1/2004 |
| WO | 2004/005291 A1 | 1/2004 |
| WO | 2004/092177 A1 | 10/2004 |
| WO | 2005/035532 A1 | 4/2005 |
| WO | 2005/042537 A1 | 5/2005 |
| WO | WO-2005/079195 A2 | 9/2005 |
| WO | 2006/027346 A2 | 3/2006 |
| WO | 2006/044687 A2 | 4/2006 |
| WO | 2006/046040 A2 | 5/2006 |
| WO | 2007/032936 A2 | 3/2007 |
| WO | 2007/038314 A2 | 4/2007 |
| WO | WO-2007/061737 A2 | 5/2007 |
| WO | 2007/088168 A1 | 8/2007 |
| WO | 2007/127175 A2 | 11/2007 |
| WO | 2008/113469 A2 | 9/2008 |
| WO | 2008/116064 A2 | 9/2008 |
| WO | 2008/131050 A1 | 10/2008 |
| WO | 2009/007029 A1 | 1/2009 |
| WO | 2009/021990 A1 | 2/2009 |
| WO | 2009/060197 A1 | 5/2009 |
| WO | 2009/085230 A1 | 7/2009 |
| WO | WO-2010/002954 A1 | 1/2010 |
| WO | 2010/105008 A2 | 9/2010 |
| WO | 2010/119264 A1 | 10/2010 |

OTHER PUBLICATIONS

Marie-Christine Bissery et al., "Experimental antitumor activity of taxotere (RP 56976, NSC 628503), a taxol analogue" Cancer Research (1991), vol. 51, pp. 4845-4852.
Bretonnet, et al., "NMR Screening Applied to the Fragment-based Generation of Inhbitors of Creatine Kinase Exploiting a New Interaction Proximate to the ATP Binding Site", Journal of Medicinal Chemistry (2007), vol. 50, pp. 1865-1875.
Chorvat Robert J. et al., "Synthesis, corticotropin-releasing factor receptor binding affinity, and pharmacokinetic properties of triazolo-imidazo, and pyrrolopyrimidines and pyridines" Journal of Medicinal Chemistry (1999), vol. 42, No. 5, pp. 833-848.
Cohen, P., "The development and therapeutic potential of protein kinase inhibitors", Curr. Opin. Chem. Biol. (1999), vol. 3, pp. 459-465.
Davies, et al., Docetaxel in non-small cell lung cancer: a review Expert Opin. Pharmacother (2003), vol. 4(4), pp. 553-565.
Defacqz, N. et al., "Synthesis of C5-substituted imidazolines" Tetrahedron Letters (2003), vol. 44, pp. 9111-9114.
Dermer, O. C., "Metallic Salts of Alcohols and Alcohol Analogs" Chem. Rev. (1934). vol. 14, pp. 385-430.
Easton, J. B. et al., "mTOR and cancer therapy" Oncogene (2006), vol. 25, pp. 6436-6446.
El-Sherbeny, A. et al., "Synthesis and cardiotonic activity of certain imidazol[2,1-b]-1,3,4-thiadiazole derivatives" Boll. Chim. Farmaceutico (1997), vol. 136, No. 3, pp. 253-256.
Fabio, P. F. et al., "Synthesis of Carbon-14 and Deuterium Labeled 3-Nitro-6-Propoxyimidazo [1,2-B]Pyridazine—An Antiparasitic Agent" Journal of Labelled Compounds and Radiopharmaceuticals (1978), vol. 15, pp. 407-413.
Gregson, S. J. et al., "Linker length Modulates DNA Cross-Linking Reactivity and Cytotoxic Potency of C8/C8 Ether-Linked C2-exo-Unsaturated Pyrrolo[2,1-c][1,4]benzodiazepine (PBD) Dimers" J. Med. Chem. (2004), vol. 47, 1161-1174.
Han, S.Y. et al., "Recent development of peptide coupling reagents in organic synthesis" Tetrahedron (2004), vol. 60, pp. 2447-2467.
Hennessy, B. T. et al., "Exploiting the PI3K/AKT Pathway for Cancer Drug Discovery" Nature Rev. Drug Dis. (2005), vol. 4, pp. 988-1004.
Herbst et al., "Mode of action of docetaxel—a basis for combgination with novel anticancer agents" Cancer Treatment Reviews (2003), vol. 29, pp. 407-415.
Ikemoto, T. et al., "Reactions with N-Chlorosuccinimide of various 5-Methylimidazo[1,2-a]pyridine derivatives with an Electron-Withdrawing Group Substituted at the 3-Position" Heterocycles (2001), vol. 55, No. 1, pp. 99-108.
Ikemoto, T. et al., "A Practical Synthesis of the Chronic Renal Disease Agent, 4,5-Dihydro-3H-1,48b-triazaacenaphthylen-3-one Derivatives, Using Regioselective Chlorination of Ethyl 5-methylimidazol[1,2-a]pyridine-3-carboxylate with N-Chlorosuccinimide" Tetrahedron (2000), vol. 56, pp. 7915-7921.
Katso, et al., "Cellular Function of Phosphoinositide 3-Kinases: Implications for Development, Immunity, Homeostasis, and Cancer" Annu. Rev. Cell. Dev. Boil. (2001), vol. 17, pp. 615-675.
Kobe, J. et al., "Synthesis of Pyridazine Derivatives—XV Some Electrophilic Substitutions on Imidazo[1,2-b]-Pyridazines" Tetrahedron (1968), vol. 24, pp. 239-245.
Kuwahara, M. et al., "Synthetic Studies on Condensed-Azole Derivatives. IV. synthesis and Anti-asthmatic Activites of ω-Sulfamoylalkylozyimidazo[1,2-b]pyridazines" Chem. Pharm Bull. (1996), vol. 44, No. 1, pp. 122-131.
Lainton J. A. H. et al., "Design and Synthesis of a Diverse Morpholine Template Library" J. Comb. Chem. (2003), vol. 5, pp. 400-407.
Leslie, et al., "Phosphoinositide-Regulated kinases and Phosphoinositide Phosphatases" Chem. Rev. (2001), vol. 101, pp. 2365-2380.
Managatal et al., "Application of the vicinal oxyamination reaction with asymmetric induction to the hemisynthesis of taxol and analogues" Tetrahedron (1989), vol. 45, No. 13, pp. 4177-4190.
Parsons, D. W. et al., "Colorectal Cancer Mutations in a signalling pathway" Nature (2005), vol. 436, p. 792.
Paul et al., "Uber cinige umsetzungen von 2,5-diamino-sowie 2-amino-1,3,4-thiadiazolen mit allalogenketonen zu Imidazo[2,1—b]-1,3,4-thiadiazolen" Monatshefte fur Chemie (1977), vol. 108, pp. 665-680.
Plotkin, M. et al., "A practical approach to highly functionalized benzodihydrofurans" Tetrahedron Letters (2000), vol. 41, pp. 2269-2273.
Ringel et al., "Studies with PR 56979 (Taxotere): A Semisynthetic Analogue of Taxol" J. National Cancer Institute (1991), vol. 83, pp. 288-291.
Schlosser M., et al., Organometallics in Synthesis. A Manual, (M. Schlosser, Ed.), Wiley & Sons Ltd: Chichester, UK, (2002).
Severinsen, R. et al., "Versatile strategies for the solid phase synthesis of small heterocyclic scaffolds: [1,3,4]-thiadiazoles and [1,3,4]-oxadiazoles" Tetrahedron (2005), vol. 61, pp. 5565-5575.
Seyden-Penne J., "Reductions by the alumino-and borohydrides in organic synthesis" VCH (1991).
Shintani R. et al., "Carbon—Carbon Bond-Forming Enantioselective Synthesis of Chiral Organosilicon Compounds by Rhodium/Chiral Diene-Catalyzed Asymmetric 1,4-Addition Reaction" Organic Letters (2005), vol. 7, No. 21, pp. 47574759.
Toker et al. "Phosphoinositides and signal transduction" Cell Mol. Life Sciences (2002), vol. 59, pp. 761-779.
Vanhaesebroeck, B. et al., "Signaling by distinct Classes of Phosphoinositide 3-Kinases" Experimental Cell Research (1999), vol. 253, pp. 239-254.
Vanhaesebroeck, B. et al., "Phosphoinositide 3-kinases: a conserved family of signal transducers" Trends Biochem. Science (1997), vol. 22, pp. 267-272.

(56) References Cited

OTHER PUBLICATIONS

Wengwei, L. et al., "Preparation of highly functionalized arylmagnesium reagents by the addition of magnesium phenylselenide to arynes", Tetrahedron Letters (2006), vol. 47, pp. 1941-1944.
Werber, G. et al., "The synthesis and Reactivity of some 2-Amino-5-bromo-1,3,4-thiadiazoles and the Corresponding Δ2-1,3,4-Thiadiazolines" J. Heterocycl. Chem. (1977), vol. 14, pp. 823-827.
Wiggins, J. M. Synth., "A convenient procedure for the reduction of diarylmethanols with dichlorodimethylsilane/sodium iodide" Communications (1988), vol. 18, No. 7, pp. 741-749.
Wipf, P. et al., "Formal Total Synthesis of (+)-Diepoxin σ" J. Org. Chem. (2000), vol. 65, pp. 6319-6337.
The International Preliminary Report on Patentability (IPRP) for International Application No. PCT/GB2010/000086 dated Jul. 24, 2012.
IUPAC Compendium of Chemical Terminology "Cycloalkanes" (2nd Edition, 1997).
Mukaiyama et al. *Bioorg. Med. Chem.* 2007, 15, pp. 868-885.
Trcek et al. *ARKIVOC* 2003, 14, pp. 246-252.
Trcek et al. *Synthesis* 2006, 20, pp. 3437-3442.
Gadad et al. *Bioorg. Med. Chem.* 2004, 12, 5651-5659.
Heinz et al. *Monatshefte für Chemie.* 1977, 108, 665-680.
Marin et al. *Farmaco.* 1992, 47, 63-75.

INHIBITORS OF PI3 KINASE

This application is a U.S. national phase of International Application No. PCT/GB2011/000086, filed Jan. 24, 2011, the disclosure of which is hereby incorporated by reference in its entirety.

FIELD OF THE INVENTION

This invention relates to novel pharmaceutically-useful compounds, which compounds are useful as inhibitors of protein or lipid kinases (such as inhibitors of the phosphoinositide 3'OH kinase (PI3 kinase) family, particularly the PI3K class I sub-type. The compounds may also be useful as inhibitors of the mammalian target of rapamycin (mTOR)). The compounds are of potential utility in the treatment of diseases such as cancer. The invention also relates to the use of such compounds as medicaments, to the use of such compounds for in vitro, in situ and in vivo diagnosis or treatment of mammalian cells (or associated pathological conditions), to pharmaceutical compositions containing them, and to synthetic routes for their production.

BACKGROUND OF THE INVENTION

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis. PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, *Current Opinion in Chemical Biology* 1999, 3, 459-465.

Phosphatidylinositol 3-kinases (PI3Ks) are a family of lipid and serine/threonine kinases that catalyze the phosphorylation of the membrane lipid phosphatidylinositol (PI) on the 3'-OH of the inositol ring to produce phosphoinositol-3-phosphate (PIP), phosphoinositol-3,4-diphosphate ($PIP_2$) and phosphoinositol-3,4,5-triphosphate ($PIP_3$), which act as recruitment sites for various intracellular signalling proteins, which in turn form signalling complexes to relay extracellular signals to the cytoplasmic face of the plasma membrane. These 3'-phosphoinositide subtypes function as second messengers in intracellular signal transduction pathways (see e.g. Trends Biochem. Sci 22 87, 267-72 (1997) by Vanhaesebroeck et al.; Chem. Rev. 101 (8), 2365-80 (2001) by Leslie et al (2001); Annu. Rev. Cell. Dev. Boil. 17, 615-75 (2001) by Katso et al; and Cell. Mol. Life. Sci. 59 (5), 761-79 (2002) by Toker et al).

Multiple PI3K isoforms categorized by their catalytic subunits, their regulation by corresponding regulatory subunits, expression patterns and signalling specific funtions (p110α, β, δ, γ) perform this enzymatic reaction (Exp. Cell. Res. 25 (1), 239-54 (1999) by Vanhaesebroeck and Katso et al., 2001, above).

The closely related isoforms p110α and β are ubiquitously expressed, while δ and γ are more specifically expressed in the haematopoietic cell system, smooth muscle cells, myocytes and endothelial cells (see e.g. Trends Biochem. Sci. 22 (7), 267-72 (1997) by Vanhaesebroeck et al). Their expression might also be regulated in an inducible manner depending on the cellular, tissue type and stimuli as well as disease context. Inductibility of protein expression includes synthesis of protein as well as protein stabilization that is in part regulated by association with regulatory subunits.

Eight mammalian PI3Ks have been identified so far, including four class I PI3Ks. Class Ia includes PI3Kα, PI3Kβ and PI3Kδ. All of the class Ia enzymes are heterodimeric complexes comprising a catalytic subunit (p100α, p110β or p110δ) associated with an SH2 domain containing p85 adapter subunit. Class Ia PI3Ks are activated through tyrosine kinase signalling and are involved in cell proliferation and survival. PI3Kα and PI3Kβ have also been implicated in tumorigenesis in a variety of human cancers. Thus, pharmacological inhibitors of PI3Kα and PI3Kβ are useful for treating various types of cancer.

PI3Kγ, the only member of the Class Ib PI3Ks, consists of a catalytic subunit p110γ, which is associated with a p110 regulatory subunit. PI3Kγ is regulated by G protein coupled receptors (GPCRs) via association with 3' subunits of heterotrimeric G proteins. PI3Kγ is expressed primarily in hematopoietic cells and cardiomyocytes and is involved in inflammation and mast cell function. Thus, pharmacological inhibitors of PI3Kγ are useful for treating a variety of inflammatory diseases, allergies and cardiovascular diseases.

These observations show that deregulation of phosphoinositol-3-kinase and the upstream and downstream components of this signalling pathway is one of the most common deregulations associated with human cancers and proliferative diseases (see e.g. Parsons et al., Nature 436:792 (2005); Hennessey et al., Nature Rev. Drug Discovery 4: 988-1004 (2005).

The mammalian target of rapamycin (mTOR) also known as FK506 binding protein 12-rapamycin associated protein 1 (FRAP1) is a protein which in humans is encoded by the FRAP1 gene. mTOR is a serine/threonine protein kinase that regulates cell growth, cell proliferation, cell motility, cell survival, protein synthesis, and transcription. The inhibition of mTORs are believed to be useful for treating various diseases/conditions, such as cancer (for example, as described in Easton et al. (2006). "mTOR and cancer therapy". Oncogene 25 (48): 6436-46).

The listing or discussion of an apparently prior-published document in this specification should not necessarily be taken as an acknowledgement that the document is part of the state of the art or is common general knowledge.

US patent application US 2009/0163489 and international patent application WO 2009/085230 both disclose various molecules containing a 6,5-fused bicyclic core, which may be useful as inhibitors of PI3 kinase (PI3-K). However, these documents do not relate to 6,5-bicyclic compounds that are substituted on the 6-membered ring with at least two substituents, an aromatic group and a morpholinyl group, or compounds that are substituted on the 5-membered ring with an alkyl or heterocycloalkyl moiety (linked via a carbon atom).

International patent applications WO 2007/127175 and WO 2006/046040 both disclose various thienopyrimidines and furopyrimidines, of potential use as PI3-K inhibitors. However, these documents do not disclose or suggest any other 6,5-fused bicyclic compounds.

International patent application WO 2004/092177 discloses various triazolopyrazines for use in modulating the $A_{2a}$ adenosine receptor signalling pathways. International patent applications WO 2006/027346, WO 2007/032936, WO 2005/042537, WO 2007/088168, WO 2008/131050, WO 03/000693, WO 2004/005290 and WO 2004/005291 and US patent application US 2006/0084650 (and international patent application WO 2006/044687) disclose various bicyclic compounds that may be useful for treating diseases/disorders such as cancer, pain, neurodegenerative disorders and/or that may be useful as kinase inhibitors. However, these documents do not relate to such bicycles that are directly substituted with both an aromatic group and a morpholinyl group.

International patent applications WO 2008/113469 and WO 2009/007029 disclose various compounds including bicyclic compounds, for use in treating diseases such as haematological diseases. However, these documents do not relate to bicycles that are substituted with a morpholinyl group.

Journal article Chorvat et al., *J. Med. Chem.* 1999, 42, 833 discloses various bicyclic compounds that may possess biological activity. However, there is no disclosure of 6,5-fused bicycles in which the 6-membered ring is directly substituted with an aromatic group.

International patent application WO 2005/035532 discloses various triazolopyrazinones that may be useful in the treatment of asthma or another glycogen synthase kinase mediated condition. However, this document only discloses 6,5-bicyclic compounds in which there is a carbonyl group attached to the 5-membered ring.

US patent applications US 2007/078136 and US 2008/045536 (and equivalent application WO 2007/038314) as well as international patent application WO 2008/116064 both disclose various compounds, including bicycles, which may be useful in the treatment of inflammatory and immune diseases. However, these documents do not predominantly relate to 6,5-fused bicyclic compounds that are substituted with both an aromatic group and a morpholinyl group.

French patent application FR 26661163 discloses various 6,5-fused bicycles, but does not specifically relate to 6,5-bicycles bearing an aromatic group and a morpholinyl group on the 6-membered ring. Nor does this document relate to kinase inhibitors.

International patent application WO 2010/119264 discloses various imidazopyrazines for use as kinase inhibitors, which imidazopyrazines may be substituted with an aromatic group and a morpholinyl group. However, this document only relates to imidazopyrazines.

DISCLOSURE OF THE INVENTION

According to the invention, there is now provided a compound of formula I,

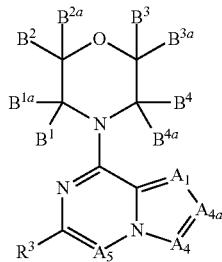

wherein:
$A_1$ represents N or $C(R^1)$;
$A_4$ represents N or $C(R^{1a})$;
$A_{4a}$ represents N or $C(R^{1b})$;
wherein at least one of $A_4$ and $A_{4a}$ does not represent N;
$A_5$ represents N or $C(R^2)$;

each $B^1$, $B^{1a}$, $B^2$, $B^{2a}$, $B^3$, $B^{3a}$, $B^4$ and $B^{4a}$ independently represent hydrogen or a substituent selected from halo, —C(=Y)—$R^{10a}$, —C(=Y)—$OR^{10a}$, —C(=Y)N($R^{10a}$)$R^{11a}$, —S(O)$_2$N($R^{10a}$)$R^{11a}$, $C_{1-12}$ alkyl, heterocycloalkyl (which latter two groups are optionally substituted by one or more substituents selected from =O and $E^1$), aryl and/or heteroaryl (which latter two groups are optionally substituted by one or more substituents selected from $E^2$); or any two $B^1$, $B^{1a}$, $B^2$, $B^{2a}$, $B^3$, $B^{3a}$, $B^4$ and $B^{4a}$ substituents that are attached to the same carbon atom (i.e. $B^1$ and $B^{1a}$; $B^2$ and $B^{2a}$; $B^3$ and $B^{3a}$; and/or $B^4$ and $B^{4a}$) may together form a =O group;

or, any two $B^1$, $B^{1a}$, $B^2$, $B^{2a}$, $B^3$, $B^{3a}$, $B^4$ and $B^{4a}$ substituents may be linked together to form a further 3- to 12-membered (e.g. 3- to 6-membered) ring, optionally containing (in addition to the atom(s) of the morpholine ring) one or more (e.g. two or, preferably, one) heteroatom(s) (preferably selected from sulfur, oxygen and nitrogen), which ring optionally contains one or more (e.g. one to three) double bonds, and which ring is itself optionally substituted by one or more substituents selected from halo, =O and $C_{1-3}$ alkyl optionally substituted by one or more fluoro atoms;

$R^1$ and $R^2$ (when present) independently represent hydrogen or a substituent selected from halo, —CN, —$OR^{10b}$, —$N(R^{10b})R^{11b}$, —$C(O)N(R^{10b})R^{11b}$, $C_{1-12}$ (e.g. $C_{1-6}$) alkyl and heterocycloalkyl (e.g. a 3- to 7-membered heterocycloalkyl), which latter two groups are optionally substituted by one or more substituents selected from $E^3$ and =O;

$R^{1b}$ (when present) represents:
(i) $C_{1-12}$ alkyl optionally substituted by one or more substituents selected from $Q^{1a}$;
(ii) heterocycloalkyl (linked to the requisite bicycle of formula I via a carbon atom of that heterocycloalkyl group) optionally substituted by one or more substituents selected from =O and $Q^{1b}$; or
(iii) a fragment of formula IA;

$R^{1a}$ (when present) represents:
(i) hydrogen;
(ii) $Q^1$;
(iii) $C_{1-12}$ alkyl optionally substituted by one or more substituents selected from =O, =S, =N($R^{10a}$) and $Q^2$; or
(iv) a fragment of formula IA;
the fragment of formula IA represents:

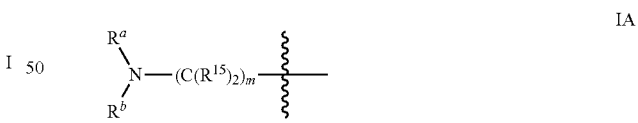

wherein:
m represents 1, 2, 3, 4, 5 or 6;
each $R^{15}$ represents hydrogen, halo (e.g. fluoro) or $C_{1-6}$ alkyl optionally substituted by one or more substituents selected from $E^4$; or any two $R^{15}$ groups may be linked together to form (along with the requisite carbon atom to which those $R^{15}$ groups are necessarily attached) a 3- to 6-membered (e.g. spiro-cyclic, when the two $R^{15}$ groups are attached to the same carbon atom) ring, which ring optionally contains one or more double bonds, and optionally contains a further heteroatom selected from nitrogen, sulfur and oxygen, and which ring is optionally substituted by one or more substituents selected from $E^5$;

$R^a$ and $R^b$ are linked together, along with the requisite nitrogen atom to which they are necessarily attached, to form a first 3- to 7-membered cyclic group, optionally containing one further heteroatom selected from nitrogen, sulfur and oxygen, and which ring:

(a) is fused to a second ring that is either a 3- to 7-membered saturated heterocycloalkyl group containing one to four heteroatoms selected from oxygen, sulfur and nitrogen (preferably oxygen and nitrogen), a 3- to 12-membered saturated carbocyclic ring, or an unsaturated 5- to 12-membered carbocyclic or heterocyclic ring (in which the heteroatoms are preferably selected from sulfur and, especially, nitrogen and oxygen);

(b) comprises a linker group $—(C(R^X)_2)_p—$ and/or $—(C(R^X)_2)_r—O—(C(R^X)_2)_s—$ (wherein p is 1 or 2; r is 0 or 1; s is 0 or 1; and each $R^x$ independently represents hydrogen or $C_{1-6}$ alkyl), linking together any two non-adjacent atoms of the first 3- to 7-membered ring (i.e. forming a bridged structure); or (c) comprises a second ring that is either a 3- to 12-membered saturated carbocyclic ring or a 3- to 7-membered saturated heterocycloalkyl group containing one to four heteroatoms selected from oxygen and nitrogen, and which second ring is linked together with the first ring via a single carbon atom common to both rings (i.e. forming a spiro-cycle), all of which cyclic groups, defined by the linkage of $R^a$ and $R^b$, are optionally substituted by one or more substituents selected from $=NOR^{10a}$, preferably, $=O$ and $E^6$;

$R^3$ represents aryl or heteroaryl (both of which are optionally substituted by one or more substituents selected from $E^7$);

each $Q^{1a}$, $Q^{1b}$, $Q^1$ and $Q^2$ independently represents, on each occasion when used herein:

halo, —CN, —NO$_2$, —N(R$^{10a}$)R$^{11a}$, —OR$^{10a}$, —C(=Y)—R$^{10a}$, —C(=Y)—OR$^{10a}$, —C(=Y)N(R$^{10a}$)R$^{11a}$, —C(=Y)N(R$^{10a}$)—OR$^{11c}$, —OC(=Y)—R$^{10a}$, —OC(=Y)—OR$^{10a}$, —OC(=Y)N(R$^{10a}$)R$^{11a}$, —OS(O)$_2$OR$^{10a}$, —OP(=Y)(OR$^{10a}$)(OR$^{10a}$), —OP(OR$^{10a}$)(OR$^{11a}$), —N(R$^{12a}$)C(=Y)R$^{11a}$, —N(R$^{12a}$)C(=Y)OR$^{11a}$, —N(R$^{12a}$)C(=Y)N(R$^{10a}$)R$^{11a}$, —NR$^{12a}$S(O)$_2$R$^{10a}$, —NR$^{12a}$S(O)$_2$N(R$^{10a}$)R$^{11a}$, —S(O)$_2$N(ROa)R$^{11a}$, —SC(=Y)R$^{10a}$, —S(O)$_2$R$^{10a}$, —SR$^{10a}$, —S(O)R$^{10a}$, $C_{1-12}$ alkyl, heterocycloalkyl (which latter two groups are optionally substituted by one or more substituents selected from $=O$, $=S$, $=N(R^{10a})$ and $E^8$), aryl or heteroaryl (which latter two groups are optionally substituted by one or more substituents selected from $E^9$);

each $R^{11c}$ independently represents $C_{1-12}$ alkyl, heterocycloalkyl (which latter two groups are optionally substituted by one or more substituents selected from $=O$, $=S$, $=N(R^{20})$ and $E^{10}$), aryl or heteroaryl (which latter two groups are optionally substituted by one or more substituents selected from $E^{11}$); each $R^{10a}$, $R^{11a}$, $R^{10b}$, $R^{11b}$ and $R^{12a}$ independently represent, on each occasion when used herein, hydrogen, $C_{1-12}$ alkyl, heterocycloalkyl (which latter two groups are optionally substituted by one or more substituents selected from $=O$, $=S$, $=N(R^{20})$ and $E^{10}$), aryl or heteroaryl (which latter two groups are optionally substituted by one or more substituents selected from $E^{11}$); or any relevant pair of $R^{10a}$ and $R^{11a}$ or $R^{10b}$ and $R^{11b}$ (for example, when attached to the same atom, adjacent atom (i.e. 1,2-relationship) or to atoms that are two atoms apart, i.e. in a 1,3-relationship) may be linked together to form (e.g. along with the requisite nitrogen atom to which they may be attached) a 4- to 20- (e.g. 4- to 12-) membered ring, optionally containing one or more heteroatoms (for example, in addition to those that may already be present, e.g. (a) heteroatom(s) selected from oxygen, nitrogen and sulfur), optionally containing one or more unsaturations (preferably, double bonds), and which ring is optionally substituted by one or more substituents selected from $=O$, $=S$, $=N(R^{20})$ and $E^{12}$;

each $E^1$, $E^2$, $E^3$, $E^4$, $E^5$, $E^6$, $E^7$, $E^8$, $E^{10}$, $E^{11}$ and $E^{12}$ independently represents, on each occasion when used herein:

(i) $Q^4$;

(ii) $C_{1-12}$ alkyl optionally substituted by one or more substituents selected from $=O$ and $Q^5$; or any two $E^1$, $E^2$, $E^3$, $E^4$, $E^5$, $E^6$, $E^7$, $E^8$, $E^{10}$, $E^{11}$ or $E^{12}$ groups (for example on $C_{1-12}$ alkyl groups, e.g. when they are attached to the same or adjacent carbon atoms, or, on aromatic groups, when attached to adjacent atoms), may be linked together to form a 3- to 12-membered ring, optionally containing one or more (e.g. one to three) unsaturations (preferably, double bonds), and which ring is optionally substituted by one or more substituents selected from $=O$ and $J^1$;

each $Q^4$ and $Q^5$ independently represent, on each occasion when used herein:

halo, —CN, —NO$_2$, —N(R$^{20}$)R$^{21}$, —OR$^{20}$, —C(=Y)—R$^{20}$, —C(=Y)—OR$^{20}$, —C(=Y)N(R$^{20}$)R$^{21}$, —C(=Y)N(R$^{20}$)—O—R$^{21a}$, —OC(=Y)—R$^{20}$, —OC(=Y)—OR$^{20}$, —OC(=Y)N(R$^{20}$)R$^{21}$, —OS(O)$_2$OR$^{20}$, —OP(=Y)(OR$^{20}$)(OR$^{21}$), —OP(OR$^{20}$)(OR$^{21}$), —N(R$^{22}$)C(=Y)R$^{21}$, —N(R$^2$)C(=Y)OR$^{21}$, —N(R$^{22}$)C(=Y)N(R$^{20}$)R$^{21}$, —NR$^{22}$S(O)$_2$R$^{20}$, —NR$^{22}$S(O)$_2$N(R$^{20}$)R$^{21}$, —S(O)$_2$N(R$^{20}$)R$^{21}$, —SC(=Y)R$^{20}$, —S(O)$_2$R$^{20}$, —SR$^{20}$, —S(O)R$^{20}$, $C_{1-6}$alkyl, heterocycloalkyl (which latter two groups are optionally substituted by one or more substituents selected from $=O$ and $J^2$), aryl or heteroaryl (which latter two groups are optionally substituted by one or more substituents selected from $J^3$);

each Y independently represents, on each occasion when used herein, $=O$, $=S$, $=NR^{23}$ or $=N—CN$;

each $R^{21a}$ represents $C_{1-6}$ alkyl, heterocycloalkyl (which latter two groups are optionally substituted by one or more substituents selected from $J^4$ and $=O$), aryl or heteroaryl (which latter two groups are optionally substituted by one or more substituents selected from $J^5$);

each $R^{20}$, $R^{21}$, $R^{22}$ and $R^{23}$ independently represent, on each occasion when used herein, hydrogen, $C_{1-6}$ alkyl, heterocycloalkyl (which latter two groups are optionally substituted by one or more substituents selected from $J^4$ and $=O$), aryl or heteroaryl (which latter two groups are optionally substituted by one or more substituents selected from $J^5$); or any relevant pair of $R^{20}$, $R^{21}$ and $R^{22}$ may (for example, when attached to the same atom, adjacent atom (i.e. 1,2-relationship) or to atoms that are two atoms apart, i.e. in a 1,3-relationship) be linked together to form (e.g. along with the requisite nitrogen atom to which they may be attached) a 4- to 20- (e.g. 4- to 12-) membered ring, optionally containing one or more heteroatoms (for example, in addition to those that may already be present, e.g. (a) heteroatom(s) selected from oxygen, nitrogen and sulfur), optionally containing one or more unsaturations (preferably, double bonds), and which ring is optionally substituted by one or more substituents selected from $J^6$ and $=O$;

each $J^1$, $J^2$, $J^3$, $J^4$, $J^5$ and $J^6$ independently represents, on each occasion when used herein:

(i) $Q^7$;

(ii) $C_{1-6}$ alkyl or heterocycloalkyl, both of which are optionally substituted by one or more substituents selected from $=O$ and $Q^8$;

each $Q^7$ and $Q^8$ independently represents, on each occasion when used herein:

halo, —CN, —N(R$^{50}$)R$^{51}$, —OR$^{50}$, —C(=Y$^a$)—R$^{50}$, —C(=Y$^a$)—OR$^{50}$, —C(=Y$^a$)N(R$^{50}$)R$^{51}$, —N(R$^{52}$)C(=Y$^a$)R$^{51}$, —NR$^2$S(O)$_2$R$^5$, —S(O)$_2$N(R$^{50}$)R$^{51}$, —N(R$^{52}$)—C(=Y$^a$)—N(R$^{50}$)R$^{51}$, —S(O)$_2$R$^{50}$, —SR$^{50}$, —S(O)R$^{50}$, C$_{1-6}$alkyl (optionally substituted by one or more fluoro atoms), heterocyclalkyl, aryl or heteroaryl (which latter three groups are optionally substituted by one or more substituents selected from halo, —OR$^{60}$ and —N(R$^{61}$)R$^{62}$);
each Y$^a$ independently represents, on each occasion when used herein, =OO, =S, =NR$^{53}$ or =N—CN;
each R$^{50}$, R$^{51}$, R$^{52}$ and R$^{53}$ independently represents, on each occasion when used herein, hydrogen or C$_{1-6}$ alkyl optionally substituted by one or more substituents selected from fluoro, —OR$^{60}$ and —N(R$^{61}$)R$^{62}$; or
any relevant pair of R$^{50}$, R$^{51}$ and R$^{52}$ may (for example when attached to the same or adjacent atoms) be linked together to form, a 3- to 8-membered ring, optionally containing one or more heteroatoms (for example, in addition to those that may already be present, heteroatoms selected from oxygen, nitrogen and sulfur), optionally containing one or more unsaturations (preferably, double bonds), and which ring is optionally substituted by one or more substituents selected from =O and C$_{1-3}$ alkyl;
R$^{60}$, R$^{61}$ and R$^{62}$ independently represent hydrogen or C$_{1-6}$ alkyl optionally substituted by one or more fluoro atoms;
or a pharmaceutically acceptable ester, amide, solvate or salt thereof,
which compounds, esters, amides, solvates and salts are referred to hereinafter as "the compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

By "pharmaceutically acceptable ester, amide, solvate or salt thereof", we include salts of pharmaceutically acceptable esters or amides, and solvates of pharmaceutically acceptable esters, amides or salts. For instance, pharmaceutically acceptable esters and amides such as those defined herein may be mentioned, as well as pharmaceutically acceptable solvates or salts.

Pharmaceutically acceptable esters and amides of the compounds of the invention are also included within the scope of the invention. Pharmaceutically acceptable esters and amides of compounds of the invention may be formed from corresponding compounds that have an appropriate group, for example an acid group, converted to the appropriate ester or amide. For example, pharmaceutically acceptable esters (of carboxylic acids of compounds of the invention) that may be mentioned include optionally substituted C$_{1-6}$ alkyl, C$_{5-10}$ aryl and/or C$_{5-10}$ aryl-C$_{1-6}$ alkyl-esters. Pharmaceutically acceptable amides (of carboxylic acids of compounds of the invention) that may be mentioned include those of the formula —C(O)N(R$^{z1}$)R$^{z2}$, in which R$^{z1}$ and R$^{z2}$ independently represent optionally substituted C$_{1-6}$ alkyl, C$_{5-10}$ aryl, or C$_{5-10}$ aryl-C$_{1-6}$ alkylene-. Preferably, C$_{1-6}$ alkyl groups that may be mentioned in the context of such pharmaceutically acceptable esters and amides are not cyclic, e.g. linear and/or branched.

Further compounds of the invention that may be mentioned include carbamate, carboxamido or ureido derivatives, e.g. such derivatives of existing amino functional groups.

For the purposes of this invention, therefore, prodrugs of compounds of the invention are also included within the scope of the invention.

The term "prodrug" of a relevant compound of the invention includes any compound that, following oral or parenteral administration, is metabolised in vivo to form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration.

Prodrugs of compounds of the invention may be prepared by modifying functional groups present on the compound in such a way that the modifications are cleaved, in vivo when such prodrug is administered to a mammalian subject. The modifications typically are achieved by synthesising the parent compound with a prodrug substituent. Prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. 1-92, Elesevier, New York-Oxford (1985).

Compounds of the invention may contain double bonds and may thus exist as E (entgegen) and Z (zusammen) geometric isomers about each individual double bond. Positional isomers may also be embraced by the compounds of the invention. All such isomers (e.g. if a compound of the invention incorporates a double bond or a fused ring, the cis- and trans-forms, are embraced) and mixtures thereof are included within the scope of the invention (e.g. single positional isomers and mixtures of positional isomers may be included within the scope of the invention).

Compounds of the invention may also exhibit tautomerism. All tautomeric forms (or tautomers) and mixtures thereof are included within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person.

All stereoisomers (including but not limited to diastereoisomers, enantiomers and atropisomers) and mixtures thereof (e.g. racemic mixtures) are included within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$O, $^{17}$O, $^{18}$O, $^{32}$P, $^{33}$P, $^{35}$S, $^{18}$F, $^{36}$Cl, $^{123}$I, and $^{125}$I. Certain isotopically-labeled compounds of the present invention (e.g., those labeled with $^3$H and $^{14}$C) are useful in compound and for substrate tissue distribution assays. Tritiated ($^3$H) and carbon-14 ($^{14}$C) isotopes are useful for their ease of preparation and detectability. Further, substitution with heavier isotopes such as deuterium (i.e., $^2$H may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Scheme 1 and/or in the Examples herein below, by substituting an isotopically labeled reagent for a non-isotopically labeled reagent.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). Such cycloalkyl groups may be monocyclic or bicyclic and may further be bridged. Further, when there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group).

Unless otherwise stated, the term $C_{1-q}$ alkylene (where q is the upper limit of the range) defined herein may be straight-chain or, when there is a sufficient number of carbon atoms, be saturated or unsaturated (so forming, for example, an alkenylene or alkynylene linker group). However, such $C^{1-q}$ alkylene groups may not be branched.

$C_{3-q}$ cycloalkyl groups (where q is the upper limit of the range) that may be specifically mentioned may be monocyclic or bicyclic alkyl groups, which cycloalkyl groups may further be bridged (so forming, for example, fused ring systems such as three fused cycloalkyl groups). Such cycloalkyl groups may be saturated or unsaturated containing one or more double bonds (forming for example a cycloalkenyl group). Substituents may be attached at any point on the cycloalkyl group. Further, where there is a sufficient number (i.e. a minimum of four) such cycloalkyl groups may also be part cyclic.

The term "halo", when used herein, preferably includes fluoro, chloro, bromo and iodo.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is between 3 and 20 (e.g. between three and ten, e.g. between 3 and 8, such as 5- to 8-). Such heterocycloalkyl groups may also be bridged. Further, such heterocycloalkyl groups may be saturated or unsaturated containing one or more double and/or triple bonds, forming for example a $C_{2-q}$ heterocycloalkenyl (where q is the upper limit of the range) group. $C_{2-q}$ heterocycloalkyl groups that may be mentioned include 7-azabicyclo[2.2.1]heptanyl, 6-azabicyclo[3.1.1]heptanyl, 6-azabicyclo[3.2.1]-octanyl, 8-azabicyclo-[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo-[3.2.1]octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form. Heterocycloalkyl mentioned herein may be stated to be specifically monocyclic or bicyclic.

For the avoidance of doubt, the term "bicyclic" (e.g. when employed in the context of heterocycloalkyl groups) refers to groups in which the second ring of a two-ring system is formed between two adjacent atoms of the first ring. The term "bridged" (e.g. when employed in the context of cycloalkyl or heterocycloalkyl groups) refers to monocyclic or bicyclic groups in which two non-adjacent atoms are linked by either an alkylene or heteroalkylene chain (as appropriate).

Aryl groups that may be mentioned include $C_{6-20}$, such as $C_{6-20}$ (e.g. $C_{6-10}$) aryl groups. Such groups may be monocyclic, bicyclic or tricyclic and have between 6 and 12 (e.g. 6 and 10) ring carbon atoms, in which at least one ring is aromatic. $C_{6-10}$ aryl groups include phenyl, naphthyl and the like, such as 1,2,3,4-tetrahydro-naphthyl. The point of attachment of aryl groups may be via any atom of the ring system. For example, when the aryl group is polycyclic the point of attachment may be via atom including an atom of a non-aromatic ring. However, when aryl groups are polycyclic (e.g. bicyclic or tricyclic), they are preferably linked to the rest of the molecule via an aromatic ring.

Unless otherwise specified, the term "heteroaryl" when used herein refers to an aromatic group containing one or more heteroatom(s) (e.g. one to four heteroatoms) preferably selected from N, O and S. Heteroaryl groups include those which have between 5 and 20 members (e.g. between 5 and 10) and may be monocyclic, bicyclic or tricyclic, provided that at least one of the rings is aromatic (so forming, for example, a mono-, bi-, or tricyclic heteroaromatic group). When the heteroaryl group is polycyclic the point of attachment may be via atom including an atom of a non-aromatic ring. However, when heteroaryl groups are polycyclic (e.g. bicyclic or tricyclic), they are preferably linked to the rest of the molecule via an aromatic ring. Heteroaryl groups that may be mentioned include 3,4-dihydro-1H-isoquinolinyl, 1,3-dihydroisoindolyl, 1,3-dihydroisoindolyl (e.g. 3,4-dihydro-1H-isoquinolin-2-yl, 1,3-dihydroisoindol-2-yl, 1,3-dihydroisoindol-2-yl; i.e. heteroaryl groups that are linked via a non-aromatic ring), or, preferably, acridinyl, benzimidazolyl, benzodioxanyl, benzodioxepinyl, benzodioxolyl (including 1,3-benzodioxolyl), benzofuranyl, benzofurazanyl, benzothiadiazolyl (including 2,1,3-benzothiadiazolyl), benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form. Heteroaryl groups mentioned herein may be stated to be specifically monocyclic or bicyclic. When heteroaryl groups are polycyclic in which there is a non-aromatic ring present, then that non-aromatic ring may be substituted by one or more =O group.

It may be specifically stated that the heteroaryl group is monocyclic or bicyclic. In the case where it is specified that the heteroaryl is bicyclic, then it may be consist of a five-, six- or seven-membered monocyclic ring (e.g. a monocyclic heteroaryl ring) fused with another a five-, six- or seven-membered ring (e.g. a monocyclic aryl or heteroaryl ring).

Heteroatoms that may be mentioned include phosphorus, silicon, boron and, preferably, oxygen, nitrogen and sulfur.

For the avoidance of doubt, where it is stated herein that a group (e.g. a $C_{1-12}$ alkyl group) may be substituted by one or more substituents (e.g. selected from $E^6$), then those substituents (e.g. defined by $E^6$) are independent of one another. That is, such groups may be substituted with the same substituent (e.g. defined by $E^6$) or different substituents (defined by $E^6$).

For the avoidance of doubt, in cases in which the identity of two or more substituents in a compound of the invention may be the same, the actual identities of the respective substituents are not in any way interdependent. For example, in the situation in which there is more than one e.g. $Q^1$, $Q^2$ or $E^1$ to $E^{12}$ (such as $E^6$) substituent present, then those $Q^1$, $Q^2$ or $E^1$ to $E^{12}$ (e.g. $E^6$) substituents may be the same or different. Further, in the case where there are e.g. $Q^1$, $Q^2$ or $E^1$ to $E^{12}$ (such as $E^6$) substituents present, in which one represents —$OR^{10a}$ (or e.g. —$OR^{20}$, as appropriate) and the other represents —$C(O)_2R^{10a}$ (or e.g. —$C(O)_2R^{20}$, as appropriate), then those $R^{10a}$ or $R^{20}$ groups are not to be regarded as being interdependent. Also, when e.g. there are two —$OR^{10a}$ substituents present, then those —$OR^{10a}$ groups may be the same or different (i.e. each $R^{10a}$ group may be the same or different).

For the avoidance of doubt, when a term such as "$E^1$ to $E^{12}$" is employed herein, this will be understood by the skilled person to mean $E^1$, $E^2$, $E^3$, $E^4$, $E^5$, $E^6$, $E^7$, $E^8$, $E^9$ (if present), $E^{10}$, $E^{11}$ and $E^{12}$, inclusively. The term "$B^1$ to $B^{4}$" as employed herein will be understood to mean $B^1$, $B^{1a}$, $B^2$, $B^{2a}$, $B^3$, $B^{3a}$, $B^4$ and $B^{4a}$, inclusively.

All individual features (e.g. preferred features) mentioned herein may be taken in isolation or in combination with any other feature (including preferred feature) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

Compounds of the invention that may be mentioned include those in which:

each $Q^{1a}$, $Q^{1b}$, $Q^1$ and $Q^2$ independently represents, on each occasion when used herein:

halo, —CN, —$NO_2$, —$N(R^{10a})R^{11a}$, —$OR^{10a}$, —$C(=Y)$—$R^{10a}$, —$C(=Y)$—$OR^{10a}$, —$C(=Y)N(R^{10a})R^{11a}$, —$OC(=Y)$—$R^{10a}$, —$OC(=Y)$—$OR^{10a}$, —$OC(=Y)N(ROa)R^{11a}$, —$OS(O)_2OR^{10a}$, —$OP(=Y)(OR^{10a})(OR^{11a})$, —$OP(OR^{10a})(OR^{11a})$, —$N(R^{12a})C(=Y)R^{10a}$, —$N(R^{12a})C(=Y)OR^{11a}$, —$N(R^{12a})C(=Y)N(R^{10a})R^{11a}$, —$NR^{12a}S(O)_2R^{10a}$, —$NR^{12a}S(O)_2N(R^{10a})R^{11a}$, —$S(O)_2N(R^{10a})R^{11a}$, —$SC(=Y)R^{10a}$, —$S(O)_2R^{10a}$, —$SR^{10a}$, —$S(O)R^{10a}$, $C_{1-12}$ alkyl, heterocycloalkyl (which latter two groups are optionally substituted by one or more substituents selected from =O, =S, =$N(R^{10a})$ and $E^8$), aryl or heteroaryl (which latter two groups are optionally substituted by one or more substituents selected from $E^9$);

each $Q^4$ and $Q^5$ independently represent, on each occasion when used herein:

halo, —CN, —$NO_2$, —$N(R^{20})R^{21}$, —$OR^{20}$, —$C(=Y)$—$R^{20}$, —$C(=Y)$—$OR^{20}$, —$C(=Y)N(R^{20})R^{21}$, —$OC(=Y)$—$R^{20}$, —$OC(=Y)$—$OR^{20}$, —$OC(=Y)N(R^{20})R^{21}$, —$OS(O)_2R^{20}$, —$OP(=Y)(OR^{20})(OR^{21})$, —$OP(OR^{20})(OR^{21})$, —$N(R^{22})C(=Y)R^{21}$, —$N(R^{22})C(=Y)OR^{21}$, —$N(R^{22})C(=Y)N(R^{20})R^{21}$, —$NR^{22}S(O)_2R^{20}$, —$NR^{21}S(O)_2N(R^{20})R^{21}$, —$S(O)_2N(R^{20})R^{21}$, —$SC(=Y)R^{20}$, —$S(O)_2R^{20}$, —$SR^{20}$, —$S(O)R^{20}$, $C_{1-6}$ alkyl, heterocycloalkyl (which latter two groups are optionally substituted by one or more substituents selected from =O and $J^2$), aryl or heteroaryl (which latter two groups are optionally substituted by one or more substituents selected from $J^3$);

each $Q^7$ and $Q^8$ independently represents, on each occasion when used herein:

halo, —CN, —$N(R^{50})R^{51}$, —$OR^{50}$, —$C(=Y^a)$—$R^{50}$, —$C(=Y^a)$—$OR^{50}$, —$C(=Y^a)N(RO)R^{51}$, —$N(R^{52})C$ ($=$$Y^a$)$R^{51}$, $-NR^{52}S(O)_2R^{50}$, $-S(O)_2R^{50}$, $-SR^{50}$, $-S(O)R^{50}$ or $C_{1-6}$ alkyl optionally substituted by one or more fluoro atoms.

The skilled person will appreciate that the bicyclic core of the compounds of the invention (containing $A_1$, $A_4$, $A_{4a}$ and $A_5$) is/are aromatic. It is further stated herein that at least one of $A_4$ and $A_{4a}$ does not represent N, i.e. that at least one of $C(R^{1a})$ or $C(R^{1b})$ is present. Both $C(R^{1a})$ and $C(R^b)$ may also be present, and, preferably at least one of $R^{1a}$ and $R^{1b}$ is present that represents either $C_{1-12}$ alkyl (optionally substituted as defined herein, e.g. by one or more substituents selected from $Q^{1a}$, or, selected from $=O$, $=S$, $=N(R^{10a})$ and $Q^2$) or a fragment of formula IA as defined herein (or, in the case of $R^{1a}$, may also represent hydrogen).

Compounds of the invention include those as hereinbefore defined, but provided that when $A_4$, $A_{4a}$ and $A_5$ respectively represent $C(R^{1a})$, $C(R^{1b})$ and $C(R^2)$, then $A_1$ does not represent N, i.e. the requisite bicycle (containing $A_1$, $A_4$, $A_{4a}$ and $A_5$) of formula I may not be the following:

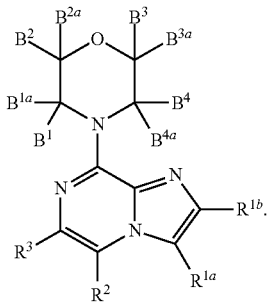

Compounds of the invention that may be mentioned include those in which, for example when $A_1$ and $A_{4a}$ both represent N, and $A_4$ and $A_5$ respectively represent $C(R^{1a})$ and $C(R^2)$ (and hence, the requisite bicyclic core of the compound of formula I is a [1,2,4]-triazolo[4,3-a]pyrazine), preferably, $R^3$ does not represent phenyl (e.g. optionally substituted, preferably unsubstituted, phenyl).

Preferred compounds of the invention that may be mentioned include those in which:

only one of $R^{1a}$ and $R^{1b}$ (e.g. if both are present) may represent a fragment of formula IA;

$R^{1b}$ represents $C_{1-12}$ alkyl (optionally substituted by one or more substituents selected from $Q^{1a}$), heterocycloalkyl (optionally substituted by one or more substituents selected from $=O$ and $Q^{1b}$) or a fragment of formula IA, and $R^{1a}$ represents hydrogen or $Q^1$;

when $R^{1a}$ represents $Q^1$, then it is preferably not $C_{1-12}$ alkyl, heterocycloalkyl, aryl or heteroaryl (optionally substituted as hereinbefore defined), but rather, in this instance $Q^1$ preferably represents halo, $-CN$, $-NO_2$, $-N(R^{10a})R^{11a}$, $-OR^{10a}$, $-C(=Y)-R^{10a}$, $-C(=Y)-OR^{10a}$, $-C(=Y)N(R^{10a})R^{11a}$, $-OC(=Y)-R^{10a}$, $-OC(=Y)-OR^{10a}$, $-OC(=Y)N(R^{10a})R^{11a}$, $-OS(O)_2OR^{10a}$, $-OP(=Y)(OR^{10a})(OR^{11a})$, $-OP(OR^{10a})(OR^{11a})$, $-N(R^{12a})C(=Y)R^{11a}$, $-N(R^{12a})C(=Y)OR^{11a}$, $-N(R^{12a})C(=Y)N(R^{10a})R^{11a}$, $-NR^{12a}S(O)_2R^{10a}$, $-NR^{12a}S(O)_2N(R^{10a})R^{11a}$, $-S(O)_2N(Ra)R^{11a}$, $-SC(=Y)R^{10a}$, $-S(O)_2R^{10a}$, $-SR^{10}$ or $-S(O)R^{10a}$ (in which $R^{10a}$, $R^{11a}$ and $R^{12a}$ preferably, and independently, represent hydrogen or $C_{1-6}$ (e.g. $C_{1-3}$) alkyl optionally substituted by one or more fluoro atoms); preferably, when $R^{1a}$ represents $Q^1$, then it is halo, $-CN$, $-NO_2$, $-N(R^{10a})R^{11a}$, $-OR^{10a}$, $-C(=Y)-R^{10a}$, $-C(=Y)(=Y)-OR^{10a}$, $-C(=Y)N(R^{10a})R^{11a}$, $-N(R^{12a})C(=Y)R^{11a}$, $-N(R^{12a})C(=Y)OR^{11a}$, $-N(R^{12a})C(=Y)N(Ra)R^{11a}$, $-NR^{12a}S(O)_2R^{10a}$, $-NR^{12a}S(O)_2N(R^{10a})R^{11a}$ or $-S(O)_2N(R^{10a})R^{11a}$ (in which $R^{10a}$, $R^{11a}$ and $R^{12a}$ preferably, and independently, represent hydrogen or $C_{1-6}$ (e.g. $C_{1-3}$) alkyl optionally substituted by one or more fluoro atoms);

more preferably, when $R^{11a}$ represents $Q^1$, then it is halo, $-CN$, $-NO_2$, $-N(R^{11a})R^{11a}$, $-OR^{10a}$, $-N(R^{12a})C(=Y)R^{11a}$, $-N(R^{12a})C(=Y)OR^{11a}$, $-N(R^{12a})C(=Y)N(R^{10a})R^{11a}$, $-NR^{12a}S(O)_2R^{10a}$, $-NR^{12a}S(O)_2N(R^{10a})R^{11a}$ or $-S(O)_2N(R^{10a})R^{11a}$ (in which $R^{10a}$, $R^{11a}$ and $R^{12a}$ preferably, and independently, represent hydrogen or $C_{1-6}$ (e.g. $C_{1-3}$) alkyl optionally substituted by one or more fluoro atoms.

More preferred compounds of the invention that may be mentioned include those in which:

$R^{1b}$ (if/when present) represents:

(i) $C_{1-12}$ alkyl optionally substituted by one or more substituents selected from $Q^{1a}$;

(ii) heterocycloalkyl (linked via a carbon atom) optionally substituted by one or more substituents selected from $=O$ and $Q^{1b}$; or (iii) a fragment of formula IA, and $R^{1a}$ (if/when present) represents:

(iii) $C_{1-12}$ alkyl optionally substituted as defined herein; or, more preferably (i) hydrogen; or (ii) $Q^1$, in which $Q^1$ is preferably as defined herein (e.g. above).

Other more preferred compounds of the invention that may be mentioned include those in which:

(A) $R^{1b}$ represents (i) $C_{1-12}$ alkyl optionally substituted by one or more substituents selected from $Q^{1a}$; (ii) heterocycloalkyl optionally substituted by one or more substituents selected from $=O$ and $Q^{1b}$; or (iii) a fragment of formula IA, and $R^{1a}$ is either not present (i.e. $A_4$ represents N) or $R^{1a}$ represents (iii) $C_{1-12}$ alkyl optionally substituted as defined herein; or, more preferably (i) hydrogen; or (ii) $Q^1$, in which $Q^1$ is preferably as defined herein (e.g. above);

(B) $R^{1b}$ represents either (i) $C_{1-12}$ alkyl optionally substituted by one or more substituents selected from $Q^{1a}$; or (ii) heterocycloalkyl optionally substituted by one or more substituents selected from $=O$ and $Q^{1b}$, and $R^{1a}$ is either not present (i.e. $A_4$ represents N) or $R^{1a}$ represents $Q^1$ (in which $Q^1$ is preferably as defined herein) or $R^{1a}$ more preferably represents hydrogen;

(C) $R^{1a}$ represents (i) hydrogen; (ii) $C_{1-12}$ alkyl optionally substituted by one or more substituents selected from $=O$, $=S$, $=N(R^{10a})$ and $Q^2$; or (iii) a fragment of formula IA, and $R^{1b}$ is either not present (i.e. $A_{4a}$ represents N; this is preferably the case) or $R^{1b}$ represents (i) $C_{1-12}$ alkyl optionally substituted as defined herein (i.e. by one or more $Q^{1a}$ substituents); or (ii) heterocycloalkyl optionally substituted as defined herein (i.e. by one or more $=O$ and/or $Q^{1b}$ substituents); and/or (D) $R^{1a}$ represents either (i) hydrogen; or (ii) $C_{1-12}$ alkyl optionally substituted by one or more substituents selected from $=O$, $=S$, $=N(R^{10a})$ and $Q^2$, and $R^{1b}$ is either not present (i.e. $A_{4a}$ represents N; this is preferably the case) or $R^{1b}$ represents hydrogen.

Further preferred compounds of the invention that may be mentioned include those in which:

when $R^{1a}$ (if present) represents optionally substituted $C_{1-12}$ alkyl, then it represents $C_{1-12}$ alkyl optionally substituted by one or more substituents selected from $Q^2$;

$Q^2$ represents halo, $-CN$, $-NO_2$, $-N(R^{1a})R^{11a}$, $-OR^{10a}$, $-C(=Y)-R^{10a}$, $-C(=Y)-OR^{10a}$, $-C(=Y)$ $N(R^{10a})R^{11a}$, —OC(=Y)—$R^{10a}$, —OC(=Y)—$OR^{10a}$, —OC(=Y)N(ROa)$R^{11a}$, —OS(O)$_2$$OR^{10a}$, —OP(=Y)($OR^{10a}$)($OR^{11a}$), —OP($OR^{10a}$)($OR^{11a}$), —N($R^{12a}$)C(=Y)$R^{11a}$, —N($R^{12a}$)C(=Y)$OR^{11a}$, —N($R^{12a}$)C(=Y)N($R^{10a}$)$R^{11a}$, —$NR^{12a}$S(O)$_2$$R^{10a}$, —$NR^{12a}$S(O)$_2$N($R^{11a}$)$R^{11a}$, —S(O)$_2$N($R^{10a}$)$R^{11a}$, —SC(=Y)$R^{10a}$, —S(O)$_2$$R^{10a}$, —$SR^{10a}$ or —S(O)$R^{10a}$ (in which $R^{10a}$, $R^{11a}$ and $R^{12a}$ preferably, and independently, represent hydrogen or $C_{1-6}$ (e.g. $C_{1-3}$) alkyl optionally substituted by one or more fluoro atoms);

preferably, $Q^2$ represents halo, —CN, —NO$_2$, —N($R^{10a}$)$R^{11a}$, —$OR^{10a}$, —C(=Y)—$R^{10a}$, —C(=Y)—$OR^{10a}$, —C(=Y)N(ROa)$R^{11a}$, —N($R^{12a}$)C(=Y)$R^{11}$, —N($R^{12a}$)C(=Y)$OR^{11a}$, —N($R^{12a}$)C(=Y)N($R^{10a}$)$R^{11a}$, —$NR^{12a}$S(O)$_2$$R^{10a}$, —$NR^{12a}$S(O)$_2$N($R^{10a}$)$R^{11a}$ or —S(O)$_2$N($R^{10a}$)$R^{11a}$ (in which $R^{10a}$, $R^{11}$ and $R^{12a}$ preferably, and independently, represent hydrogen or $C_{1-6}$ (e.g. $C_{1-3}$) alkyl optionally substituted by one or more fluoro atoms);

more preferably, $Q^2$ represents halo, —CN, —NO$_2$, —N($R^{10a}$)$R^{11a}$, —$OR^{10a}$, —N($R^{12a}$)C(=Y)$R^{11a}$, —N($R^{12a}$)C(=Y)$OR^{11a}$, —N($R^{12a}$)C(=Y)N($R^{10a}$)$R^{11a}$, —$NR^{12a}$S(O)$_2$$R^{10a}$, —$NR^{12a}$S(O)$_2$N($R^{10a}$)$R^{11a}$ or —S(O)$_2$N($R^{10a}$)$R^{11a}$ (in which $R^{10a}$, $R^{11a}$ and $R^{12a}$ preferably, and independently, represent hydrogen or $C_{1-6}$ (e.g. $C_{1-3}$) alkyl optionally substituted by one or more fluoro atoms.

Compounds of the invention that may be mentioned include those in which: each $Q^1$ independently represents, on each occasion when used herein, halo, —CN, —NO$_2$, —$OR^{10a}$, —OC(=Y)—$R^{10a}$, —OC(=Y)—$OR^{10a}$, —OC(=Y)N(ROa)$R^{11a}$, —OS(O)$_2$$OR^{10a}$, —OP(=Y)($OR^{10a}$)($OR^{11a}$), OP($OR^{10a}$)($OR^{11a}$), —N($R^{12a}$)C(=Y)$R^{11a}$, —SC(=Y)$R^{10a}$, —$SR^{10a}$, —S(O)ROa, $C_{1-12}$ alkyl, heterocycloalkyl (which latter two groups are optionally substituted by one or more substituents selected from $E^8$), aryl or heteroaryl (which latter two groups are optionally substituted by one or more substituents selected from $E^9$);

more preferably, each $Q^1$ independently represents, on each occasion when used herein, halo, —CN, —NO$_2$, $C_{1-12}$ alkyl or heterocycloalkyl (which latter two groups are optionally substituted by one or more substituents selected from $E^8$).

Compounds of the invention that may be mentioned include those in which, for example when $A_1$ and $A_{4a}$ represent N, $A_5$ represents $C(R^2)$ and $A_4$ represents $C(R^{1a})$ then, $R^{1a}$ preferably does not represent —$OR^{10a}$ in which $R^{10a}$ represents H.

Further compounds of the invention that may be mentioned include those in which, for example when $A_1$ represents N, $A_4$ represents $C(R^{1a})$, $A_{4a}$ represents N and $A_5$ represents $C(R^2)$, then $R^3$ does not represent aryl (e.g. phenyl), especially unsubstituted aryl/phenyl.

For the avoidance of doubt, the requisite bicycle of formula I refers to the aromatic bicycle containing the integers $A^1$, $A^4$, $A^{4a}$ and $A^5$ (as well as the further two nitrogen atoms and three carbon atoms). The following requisite bicycles of formula I are particularly preferred:

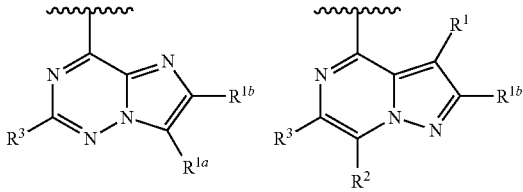

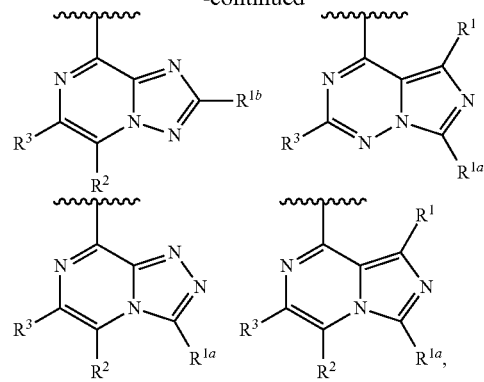

in which $R^1$, $R^{1a}$, $R^{1b}$, $R^2$ and $R^3$ are as hereinbefore defined, and the squiggly lines represent the point of attachment of the bicyclic heteroaryl group (of formula I) to the requisite (optionally substituted) morpholinyl group of the compound of formula I. The preferred heterobicyclic cores depicted above represent an embodiment of the invention in which $A^{4a}$ represents $C(R^{1a})$ and an embodiment of the invention in which $A^{4a}$ represents N. In further, more specific embodiments of the invention, the compounds of the invention may represent any one (or more) of the specific bicyclic heteroaryl groups (in which $A^{4a}$ represents either $C(R^{1a})$ or N) depicted above. It is preferred that at least one of $A_1$, $A_4$ and $A_{4a}$ represents N and hence, it is also preferred that a total of one or two of $A_1$, $A_4$ and $A_{4a}$ represents N (and preferably a total of one or two of $A_1$, $A_4$, $A_{4a}$ and $A_5$ represents N). Hence, the following bicycles are possible:

(a) $A_1$ represents N, $A_4$ represents N, $A_{4a}$ represents $C(R^{1b})$ and $A_5$ represents $C(R^2)$;

(b) $A_1$ represents N, $A_4$ represents $C(R^{1a})$, $A_{4a}$ represents $C(R^{1b})$ and $A_5$ represents N;

(c) $A_1$ represents $C(R^1)$, $A_4$ represents N, $A_{4a}$ represents $C(R^{1b})$ and $A_5$ represents $C(R^2)$;

(d) $A_1$ represents N, $A_4$ represents $C(R^{1a})$, $A_{4a}$ represents N and $A_5$ represents $C(R^2)$;

(e) $A_1$ represents $C(R^1)$, $A_4$ represents $C(R^{1a})$, $A_{4a}$ represents N and As represents N;

(f) $A_1$ represents $C(R^1)$, $A_4$ represents $C(R^{1a})$, $A_{4a}$ represents N and $A_5$ represents $C(R^2)$.

The most preferred of the above bicycles are (a), (b), (c), (e) and (f).

The most preferred requisite bicycles of formula I are:

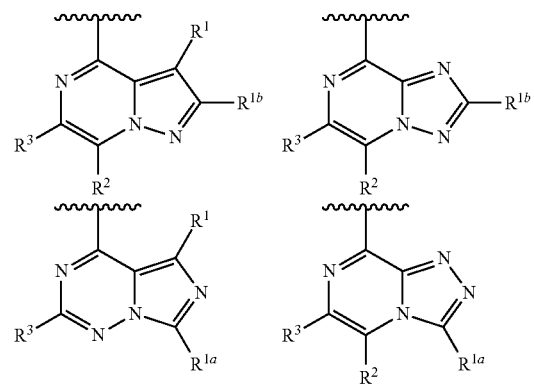

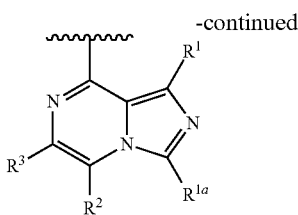

wherein the integers are as defined herein.

The preferred bicycles depicted above may exist in different forms, for example as the following alternative aromatic bicycle:

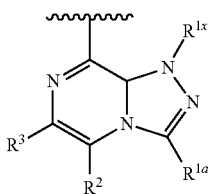

wherein $R^{1a}$, $R^2$ and $R^3$ are as hereinbefore defined, and $R^{1x}$ may represent hydrogen or a substituent such as one hereinbefore defined in respect of $R^1$ and $R^2$.

In certain embodiments, the present invention provides compounds of the invention in which:

$R^{1b}$ is —$(CR^6R^7)_m NR^{10}R^{11}$ where m is 1, 2 or 3, and $R^{10}$ and $R^{11}$ together with the nitrogen to which they are attached form a $C_3$-$C_{20}$ heterocyclic ring; and $R^{1a}$, if present, is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{76}$ or $NR^{16}R^{17}$;

$R^{1b}$ is —$(CR^6R^7)_n NR^{12}S(O)_2R^{10}$ where n is 1 or 2; $R^{12}$, $R^6$, and $R^7$ are independently selected from H and $C_{1-12}$ alkyl; and $R^{10}$ is $C_1$-$C_{12}$ alkyl or $C_6$-$C_{20}$ aryl; and $R^{1a}$, if present, is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^{1b}$ is —$(CR^6R^7)_n OR^{10}$ where n is 1 or 2, and $R^{10}$, $R^6$ and $R^7$ are independently selected from H and $C_{1-12}$ alkyl; and $R^{1a}$, if present, is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^{1b}$ is —$(CR^6R^7)_n S(O)_2R^{10}$ where n is 1 or 2; and $R^6$ and $R^7$ are H, $R^{10}$ may be $C_{1-12}$ alkyl or $C_6$-$C_{20}$ aryl; and $R^{1a}$, if present, is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^{1b}$ is —$(CR^6R^7)_n S(O)_2 NR^{10}R^{11}$ where n is 1 or 2; and $R^6$ and $R^7$ are H; and $R^{1a}$, if present, is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{11}R^{17}$;

$R^{1b}$ is $C_3$-$C_{12}$ alkyl, and $R^{1a}$, if present, is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$; $R^{1b}$ is $C_2$-$C_8$ alkenyl, and $R^{1a}$, if present, is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^{1b}$ is $C_2$-$C_8$ alkynyl (the $C_2$-$C_8$ alkynyl may be substituted with $C_2$-$C_{20}$ heterocyclyl, which includes, but is not limited to, morpholinyl, piperidinyl, piperazinyl, and pyrrolidinyl); and $R^{1a}$, if present, is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^{1b}$ is $C_3$-$C_{12}$ carbocyclyl; and $R^{1a}$, if present, is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^{1b}$ is $C_2$-$C_{20}$ heterocyclyl (attached via a carbon atom); and $R^{1a}$, if present, is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$ or $NR^{16}R^{17}$;

$R^{1b}$ may be methyl ($CH_3$), cyclopropyl or $CF_3$.

In certain embodiments of the invention:

$R^{1a}$ is —$(CR^6R^7)_m NR^{10}R^{11}$ where m is 1, 2 or 3, and $R^{10}$ and $R^{11}$ together with the nitrogen to which they are attached form a $C_3$-$C_{20}$ heterocyclic ring; and $R^{1b}$, if present, is $C_{1-6}$ alkyl, $C_3$-$C_6$ cycloalkyl or $C_2$-$C_6$ heterocycloalkyl (linked via a carbon atom);

$R^{1a}$ is —$(CR^6R^7)_n NR^{12}S(O)_2R^{10}$ where n is 1 or 2; $R^{12}$, $R^6$, and $R^7$ are independently selected from H and $C_{1-12}$ alkyl; and $R^{10}$ is $C_1$-$C_{12}$ alkyl or $C_6$-$C_{20}$ aryl; and $R^{1b}$, if present, is $C_{1-6}$ alkyl, $C_3$-$C_6$ cycloalkyl or $C_2$-$C_6$ heterocycloalkyl (linked via a carbon atom);

$R^{1a}$ is —$(CR^6R^7)_n OR^1$ where n is 1 or 2, and $R^{10}$, $R^6$ and $R^7$ are independently selected from H and $C_{1-12}$ alkyl; and $R^{1b}$, if present, is $C_{1-6}$ alkyl, $C_3$-$C_6$ cycloalkyl or $C_2$-$C_6$ heterocycloalkyl (linked via a carbon atom);

$R^{1a}$ is —$(CR^6R^7)_n S(O)_2R^{10}$ where n is 1 or 2; and $R^6$ and $R^7$ are H, $R^{10}$ may be $C_{1-12}$ alkyl or $C_6$-$C_{20}$ aryl; and $R^{1b}$, if present, is $C_{1-6}$ alkyl, $C_3$-$C_6$ cycloalkyl or $C_2$-$C_6$ heterocycloalkyl (linked via a carbon atom);

$R^{1a}$ is —$(CR^6R^7)_n S(O)_2 NR^{10}R^{11}$ where n is 1 or 2; and $R^6$ and $R^7$ are H; and $R^{1b}$, if present, is $C_{1-6}$ alkyl, $C_3$-$C_6$ cycloalkyl or $C_2$-$C_6$ heterocycloalkyl (linked via a carbon atom);

$R^{1a}$ is —$C(=Y)NR^{10}R^{11}$ where Y is O, and $R^{10}$ and $R^{11}$ together with the nitrogen to which they are attached form the $C_2$-$C_{20}$ heterocyclic ring; $R^{10}$ and $R^{11}$ together with the nitrogen to which they are attached may form a $C_2$-$C_{20}$ heterocyclic ring selected from morpholinyl, piperidinyl, piperazinyl, and pyrrolidinyl; and $R^{1b}$ is preferably not present, but, if present, is $C_{1-6}$ alkyl, $C_3$-$C_6$ cycloalkyl or $C_2$-$C_6$ heterocycloalkyl (linked via a carbon atom);

$R^{1a}$ is —$C(=Y)NR^{10}R^{11}$ where Y is O, and $Ro^1$ and $R^{11}$ are independently selected from H and $C_1$-$C_{12}$ alkyl; and $R^{1b}$ is preferably not present, but, if present, is $C_{1-6}$ alkyl, $C_3$-$C_6$ cycloalkyl or $C_2$-$C_6$ heterocycloalkyl (linked via a carbon atom);

$R^{1a}$ is —$C(=Y)NR^{10}R^{11}$ where Y is O, and $R^{10}$ and $R^{11}$ are independently selected from H and $C_3$-$C_{12}$ carbocyclyl, $C_2$-$C_{20}$ heterocyclyl, $C_6$-$C_{20}$ aryl, and $C_1$-$C_{20}$ heteroaryl; and $R^{1b}$ is preferably not present, but, if present, is $C_{1-6}$ alkyl, $C_3$-$C_6$ cycloalkyl or $C_2$-$C_6$ heterocycloalkyl (linked via a carbon atom);

$R^{1a}$ is —$NHR^{12}$ where $R^{12}$ is $C_3$-$C_{12}$ carbocyclyl, $C_2$-$C_{20}$ heterocyclyl, $C_6$-$C_{20}$ aryl or $C_1$-$C_{20}$ heteroaryl, or, $R^{12}$ may be phenyl or 4-pyridyl; and $R^{1b}$ is preferably not present, but, if present, is $C_{1-6}$ alkyl, $C_3$-$C_6$ cycloalkyl or $C_2$-$C_6$ heterocycloalkyl (linked via a carbon atom);

$R^{1a}$ is —$NR^{12}C(=Y)R^{11}$ where Y is O, $R^{12}$ is H or $C_1$-$C_{12}$ alkyl, and $R^{11}$ is $C_1$-$C_{12}$ alkyl, $C_3$-$C_{12}$ carbocyclyl, $C_2$-$C_{20}$ heterocyclyl, $C_6$-$C_{20}$ aryl, or $C_1$-$C_{20}$ heteroaryl; and $R^{1b}$ is preferably not present, but, if present, is $C_{1-6}$ alkyl, $C_3$-$C_6$ cycloalkyl or $C_2$-$C_6$ heterocycloalkyl (linked via a carbon atom);

$R^{1a}$ is —$NR^{12}S(O)_2R^{10}$ where $R^{12}$ is H or $C_1$-$C_{12}$ alkyl, and $R^{10}$ is $C_1$-$C_{12}$ alkyl, $C_3$-$C_{12}$ carbocyclyl, $C_2$-$C_{20}$ heterocyclyl, $C_6$-$C_{20}$ aryl, or $C_1$-$C_{20}$ heteroaryl; and $R^{1b}$ is preferably not present, but, if present, is $C_{1-6}$ alkyl, $C_3$-$C_6$ cycloalkyl or $C_2$-$C_6$ heterocycloalkyl (linked via a carbon atom);

$R^{1a}$ is —$S(O)_2 NR^{10}R^{11}$ where $R^{10}$ and $R^{11}$ together with the nitrogen to which they are attached form a $C_2$-$C_{20}$ heterocyclyl ring selected from morpholinyl, piperidinyl, piperazinyl, and pyrrolidinyl; and $R^{1b}$ is preferably not present, but, if present, is $C_{1-6}$ alkyl, $C_3$-$C_6$ cycloalkyl or $C_2$-$C_6$ heterocycloalkyl (linked via a carbon atom);

$R^{1a}$ is —$S(O)_2NR^{10}R^{11}$ where $R^{10}$ and $R^{11}$ are independently selected from H and $C_1$-$C_{12}$ alkyl, $R^{10}$ and $R^{11}$ may be independently selected from H, substituted ethyl, and substituted propyl; and $R^{1b}$ is preferably not present, but, if present, is $C_{1-6}$ alkyl, $C_3$-$C_6$ cycloalkyl or $C_2$-$C_6$ heterocycloalkyl (linked via a carbon atom);

$R^{1a}$ is $C_1$-$C_{12}$ alkyl, and $R^{1b}$, if present, is $C_{1-6}$ alkyl, $C_3$-$C_6$ cycloalkyl or $C_2$-$C_6$ heterocycloalkyl (linked via a carbon atom);

$R^{1a}$ is $C_2$-$C_8$ alkenyl, and $R^{1b}$, if present, is $C_{1-6}$ alkyl, $C_3$-$C_6$ cycloalkyl or $C_2$-$C_6$ heterocycloalkyl (linked via a carbon atom);

$R^{1a}$ is $C_2$-$C_8$ alkynyl (the $C_2$-$C_8$ alkynyl may be substituted with $C_2$-$C_{20}$ heterocyclyl, which includes, but is not limited to, morpholinyl, piperidinyl, piperazinyl, and pyrrolidinyl); and $R^{1b}$, if present, is $C_{1-6}$ alkyl, $C_3$-$C_6$ cycloalkyl or $C_2$-$C_6$ heterocycloalkyl (linked via a carbon atom);

$R^{1a}$ is $C_3$-$C_{12}$ carbocyclyl; and $R^{1b}$, if present, is $C_{1-6}$ alkyl, $C_3$-$C_6$ cycloalkyl or $C_2$-$C_6$ heterocycloalkyl (linked via a carbon atom);

$R^{1a}$ is $C_2$-$C_{20}$ heterocyclyl; and $R^{1b}$, if present, is $C_{1-6}$ alkyl, $C_3$-$C_6$ cycloalkyl or $C_2$-$C_6$ heterocycloalkyl (linked via a carbon atom).

In the above two paragraphs (and in certain other paragraphs herein), any relevant alkyl, cycloalkyl, heterocycloalkyl, aryl or heteroaryl groups may be optionally substituted by relevant substituents defined herein (for example, by a substituent defined by $Q^{1a}$, $Q^{1b}$, $Q^1$, $Q^2$, $E^8$, $E^9$, $Q^4$, $Q^5$, $J^2$ or $J^3$ (e.g. by $Q^1$, $E^8$ and/or $E^9$; and/or, if applicable by =O)). Further, unless otherwise specified in the above two paragraphs:

(i) each $R^{16}$ and $R^{17}$ respectively represents substituents $R^{20}$ and $R^{21}$ as defined herein (and more preferably, they respectively represent substituents $R^{50}$ and $R^{51}$ as defined herein);
(ii) each $R^6$ and $R^7$ may independently represent a substituent as defined by $R^{15}$ herein (i.e. each may independently represent hydrogen, a substituent as defined herein, or, $R^6$ and $R^7$ may be linked together in the same manner as two $R^{15}$ groups attached to the same carbon atom may be);
(iii) each $R^{10}$, $R^{11}$ and $R^{12}$ respectively represents a substituent as defined by the substituents $R^{10a}$, $R^{11a}$ and $R^{12a}$ (and any relevant pair may be linked together).

In certain embodiments, $R^{1a}$ or $R^{1b}$ represent a fragment of formula IA, as hereinbefore depicted, wherein:

$R^a$ and $R^b$ form, together with the N atom to which they are attached, a group of the following formula:

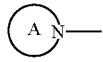

in which:
(a) ring A is a first 3- to 7-membered saturated N-containing heterocyclic ring which is fused to a second ring as hereinbefore defined to form a heteropolycyclic ring system in which the first ring is selected from, but not limited to, azetidine, pyrrolidine, piperidine, piperazine, morpholine, thiomorpholine and homopiperazine, said group being fused to a second ring as hereinbefore defined. The second ring is typically a 3- to 7-membered saturated N-containing heterocyclic ring as defined above in respect of the first ring, or the second ring is a 5- to 12-membered unsaturated heterocyclic group. More typically the second ring is a 5-, 6- or 7-membered saturated N-containing heterocyclic ring or a 5- to 7-membered unsaturated heterocyclic ring. Typical examples of the second ring include azetidine, pyrrolidine, piperidine, piperazine, morpholine, thiomorpholine, homopiperazine, pyrrole, imidazole, pyridine, pyridazine, pyrimidine, pyrazine, tetrahydrofuran and tetrahydropyran. Examples of the resulting heteropolycyclic system include octahydropyrrolo[1,2-a]pyrazine and octahydropyrrolo[3,4-c]pyrrole. Specific examples of the heteropolycyclic system include the following structures:

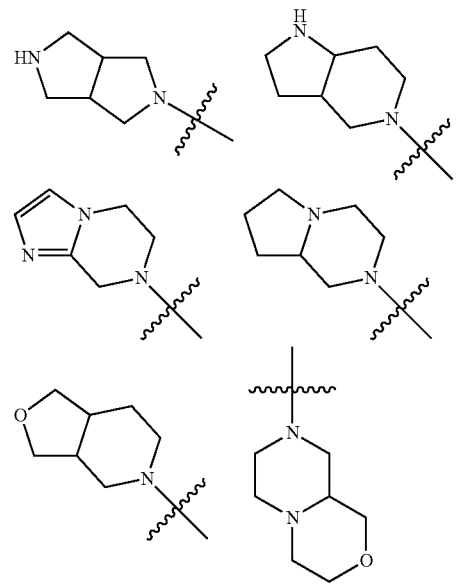

(b) ring A is a first 3- to 7-membered saturated containing heterocyclic group as hereinbefore defined, which includes, but is not limited to, a bridgehead group (i.e. a linker group linking any two non-adjacent atoms of the first ring), thereby forming, for example 3,8-diaza-bicyclo[3.2.1]octane, 2,5-diaza-bicyclo[2.2.1]heptane, 8-aza-bicyclo[3.2.1]octane, 2-aza-bicyclo[2.2.1]heptane, 3,6-diaza-bicyclo[3.1.1]heptane, 6-aza-bicyclo[3.1.1]heptane, 3,9-diaza-bicyclo[4.2.1]nonane and/or 2-oxa-7,9-diazabicyclo[3.3.1]nonane. Specific examples of this group include the following structures:

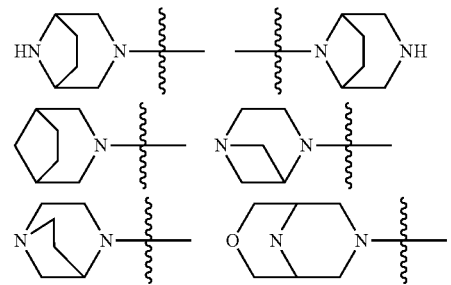

(c) ring A is a first 3- to 7-membered saturated N-containing heterocyclic group as hereinbefore defined, which is spiro-fused at any available ring carbon atom to a second 3- to 12-membered saturated carbocyclic ring, typically to a 3- to 6-membered saturated carbocyclic ring, or to a 4- to 7-membered saturated N-containing heterocyclic group. Examples include a group in which the first ring is selected from azetidine, pyrrolidine, piperidine and piperazine which is spiro-fused at a ring carbon atom to a second ring selected from cyclopropane, cyclobutane, cyclopentane, cyclohexane, azetidine, pyrrolidine, piperidine, piperazine and tetrahydropyran. The ring so formed may, for instance, be a group derived from 3,9-diazaspiro[5.5]undecane, 2,7-diazaspiro[3.5]nonane, 2,8-diazaspiro[4.5]decane or 2,7-diazaspiro[4.4]nonane. Specific examples of such groups include the following structures:

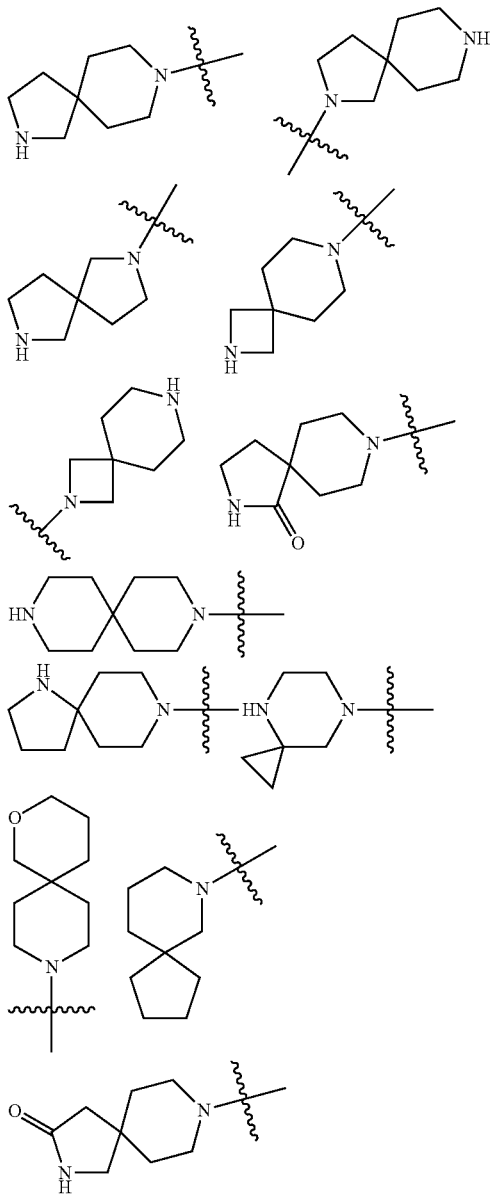

In certain embodiments, $R^{1b}$ represent a fragment of formula IA as depicted hereinbefore, in which $R^a$, $R^b$ is as described above; and $R^{1a}$ is H, halo, CN, $C_{1-6}$ alkyl, $C_3$-$C_6$ cycloalkyl, $C_2$-$C_6$ heterocycloalkyl, $C(O)N(R^{16}R^{17})$, $OR^{16}$, $NR^{16}R^{17}$. The integers $R^{16}$ and $R^{17}$ are as defined herein.

In certain embodiments, $R^{1a}$ represent a fragment of formula IA as depicted hereinbefore, in which $R^a$, $R^b$ is as described above; and $R^{1b}$ is $C_{1-6}$ alkyl, $C_3$-$C_6$ cycloalkyl or $C_2$-$C_6$ heterocycloalkyl (linked via a carbon atom). The integers $R^{16}$ and $R^{17}$ are as defined herein.

Exemplary embodiments of $R^3$ include, but are not limited to: pyrrole, pyrazole, triazole, tetrazole, thiazole, isothiazole, oxazole, isoxazole, isoindole, 1,3-dihydro-indol-2-one, pyridine-2-one, pyridine, pyridine-3-ol, imidazole, 1H-indazole, 1H-indole, indolin-2-one, 1-(indolin-1-yl)ethanone, pyrimidine, pyridazine, pyrazine and isatin groups. 1H-benzo[d][1,2,3]triazole, 1H-pyrazolo[3,4-b]pyridine, 1H-pyrazolo[3,4-d]pyrimidine, 1H-benzo[d]imidazole, 1H-benzo[d]imidazol-2(3H)-one, 1H-pyrazolo[3,4-c]pyridine, 1H-pyrazolo[4,3-d]pyrimidine, 5H-pyrrolo[3,2-d]pyrimidine, 2-amino-1H-purin-6(9H)-one, quinoline, quinazoline, quinoxaline, isoquinoline, isoquinolin-1(2H)-one, 3,4-dihydroisoquinolin-1(2H)-one, 3,4-dihydroquinolin-2(1H)-one, quinazolin-2(1H)-one, quinoxalin-2(1H)-one, 1,8-napthyridine, pyrido[3,4-d]pyrimidine, and pyrido[3,2-b]pyrazine, 1,3-dihydro benzimidazolone, benzimidazole, benzothiazole and benzothiadiazole, groups. These groups may be unsubstituted or substituted.

The attachment site of the $R^3$ group to the relevant carbon atom of the requisite bicyclic $A_1$, $A_4$, $A_{4a}$ and $A_5$-containing ring of formula I may preferably be via any carbon of the $R^3$ group (carbon-linked).

More exemplary embodiments of $R^3$ include, but are not limited to, the following groups, where the wavy line indicates the site of attachment to the requisite bicyclic core of formula I:

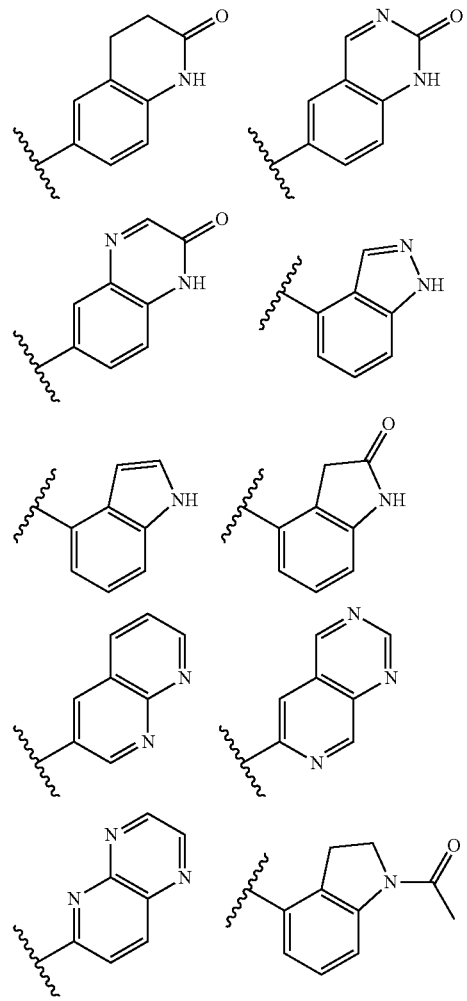

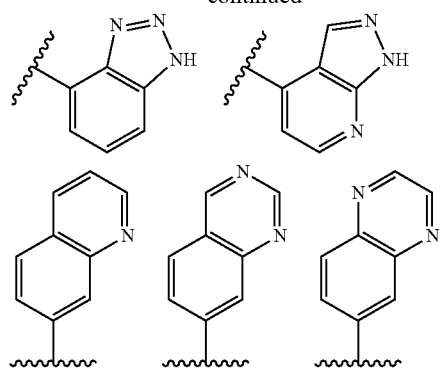
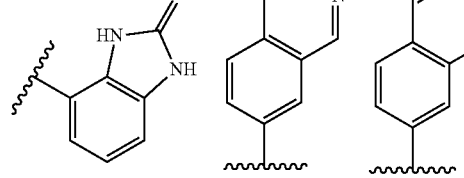
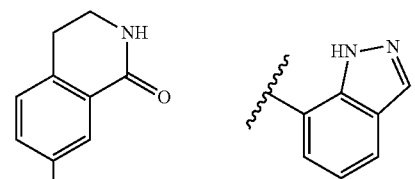
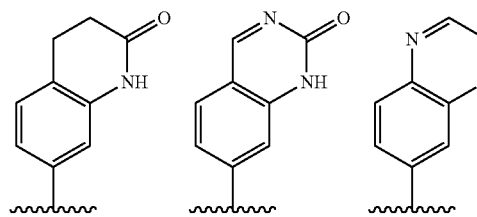
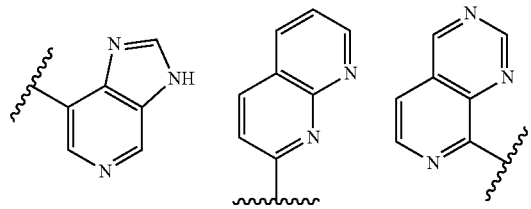
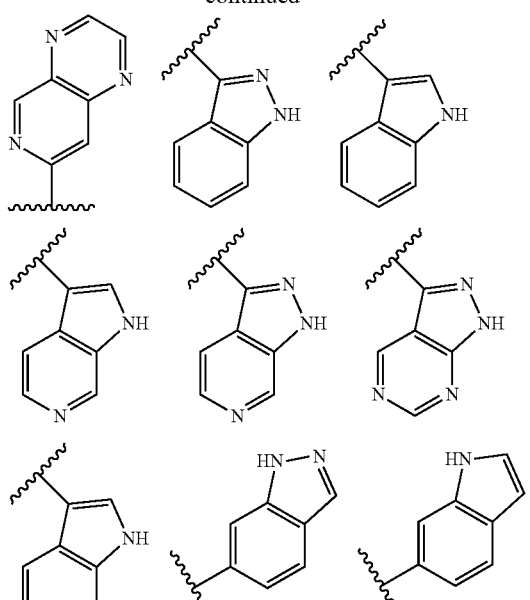
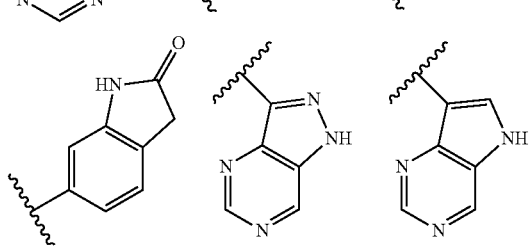
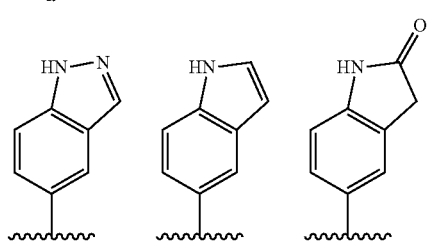
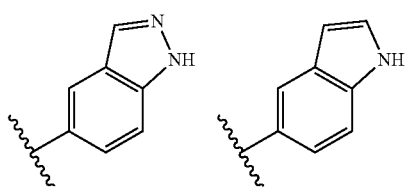
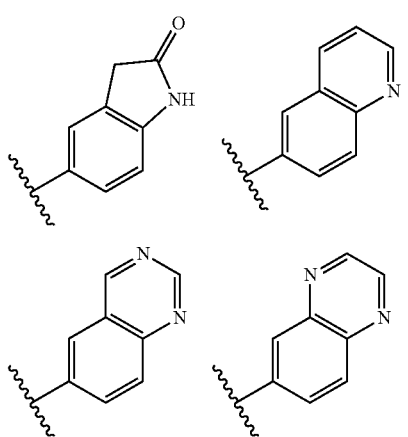

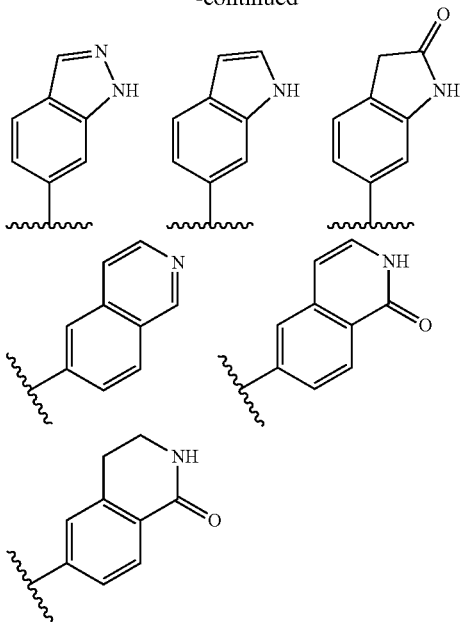

Preferred compounds of the invention include those in which:

when $R^3$ represents aryl (e.g. phenyl), then that group may be unsubstituted but is preferably substituted by at least one (e.g. two or, preferably, one) substituent(s) selected from $E^7$;

when $R^3$ represents monocyclic heteroaryl (e.g. a 5- or 6-membered heteroaryl group), then that group preferably contains 1, 2, 3 or 4 nitrogen atoms and, optionally 1 or 2 additional heteroatoms selected from oxygen and sulfur, and which heteroaryl group is optionally substituted by one or more substituents selected from $E^7$ (preferably, such monocyclic heteroaryl groups preferably contain a maximum of four heteroatoms);

when $R^3$ represents bicyclic heteroaryl (e.g. a 8-, 9- or 10-membered heteroaryl group), then that group preferably consists of a 5- or 6-membered ring fused to another 5- or 6-membered ring (in which either one of those rings may contain one or more (e.g. four, or, preferably one to three) heteroatoms), in which the total number of heteroatoms is preferably one to four, and which ring is optionally substituted by one or more (e.g. two or, preferably, one) substituent(s) selected from $E^7$ (and, if there is a non-aromatic ring present in the bicyclic heteroaryl group, then such a group may also be substituted by one or more (e.g. one) =O groups);

optional substituents (e.g. the first optional substituent) on the $R^3$ group (e.g. when it represents aryl, such as phenyl) are preferably selected from —OR, —SR, —CH$_2$OR, CO$_2$R, CF$_2$OH, CH(CF$_3$)OH, C(CF$_3$)$_2$OH, —(CH$_2$)$_w$OR, —(CH$_2$)$_w$NR$_2$, —C(O)N(R)$_2$, —NR$_2$, —NRC(O)R, —NRC(O)NHR, —NRC(O)N(R)$_2$, —S(O)$_y$N(R)$_2$, —OC(O)R, OC(O)N(R)$_2$, —NRS(O)$_y$R, —NRC(O)N(R)$_2$, CN, halogen and —NO$_2$ (in which each R is independently selected from H, C$_1$-C$_6$ alkyl, C$_3$-C$_{10}$ cycloalkyl and a 5- to 12-membered aryl or heteroaryl group, the groups being unsubstituted or substituted (for example by one or more substituents as defined herein, e.g. substituents on $E^7$ moieties, e.g. =O, $J^2$, $J^3$, $J^4$ and/or $J^5$), w is 0, 1 or 2 and y is 1 or 2);

when $R^3$ represents aryl (e.g. phenyl), then that group is substituted by one or two substituents (e.g. by a first substituent as defined above, and, optionally a further substituent (or a further two substituents) preferably selected from halo, C$_{1-12}$ alkyl, CN, NO$_2$, OR$^d$, SR$^d$, NR$^d$2, C(O)R$^d$, SOR$^d$, SO$_2$R$^d$, SO$_2$N(R)$^d$$_2$, NC(O)R$^d$ and CO$_2$R$^d$ (wherein each R$^d$ is independently H or C$_1$-C$_6$ alkyl);

when $R^3$ represents substituted aryl (e.g. phenyl), then the substituent may be situated at the 2-, 3-, 4-, 5- or 6-position of the phenyl ring (typically it is situated at position 3 or 4; particularly preferred are phenyl groups substituted by —OR$^d$ (in which R$^d$ is independently H or C$_1$-C$_6$ alkyl, e.g. methyl), e.g. —OH; in this embodiment the —OR$^d$ group, or —OH group, is typically situated at the 3- or 4-position of the phenyl ring, so forming a 3-hydroxyphenyl or 4-hydroxyphenyl group or an isostere thereof, which is unsubstituted or substituted; an isostere as used herein is a functional group which possesses binding properties which are the same as, or similar to, the 3-hydroxyphenyl or 4-hydroxyphenyl group in the context of the compounds of the invention; isosteres of 3-hydroxyphenyl and 4-hydroxyphenyl groups are encompassed within definitions (b) above for $R^5$);

when $R^3$ represents heteroaryl, it is unsubstituted or substituted (when substituted, it may be substituted by one or more substitutents selected from those listed in respect of substituents on $R^3$, when $R^3$ is a phenyl group; typically, the substituents are selected from —OC$_1$— alkyl and, preferably, OH and NH$_2$).

Preferred compounds of the invention include those in which:

$B^1$, $B^{1a}$, $B^2$, $B^{2a}$, $B^3$, $B^{3a}$, $B^4$ and $B^{4a}$ independently represent hydrogen, C$_{1-6}$ (e.g. C$_{1-3}$) alkyl optionally substituted by one or more substituents selected from =O and $E^1$, or any two of these together form a =O substituent on the morpholinyl ring, or, any two $B^1$, $B^{1a}$, $B^2$, $B^{2a}$, $B^3$, $B^{3a}$, $B^4$ and $B^{4a}$ substituents when linked together, may form a linkage, for example between a $B^2$ or $B^{2a}$ substituent and a $B^3$ or $B^{3a}$ substituent for a further ring, e.g. a five membered ring such as the one depicted below:

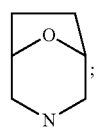

for instance, the $B^1$ to $B^4$ substituted morpholinyl group may represent N-morpholinyl which is unsubstituted or substituted, for instance by one or more $B^1$ to $B^4$ and/or =O substituents;

when it represents substituted morpholinyl, it is preferably selected from the following structures:

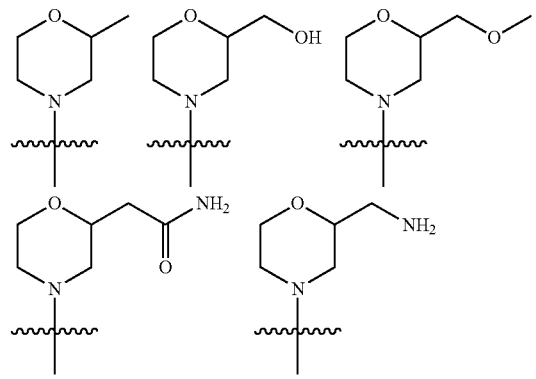

-continued

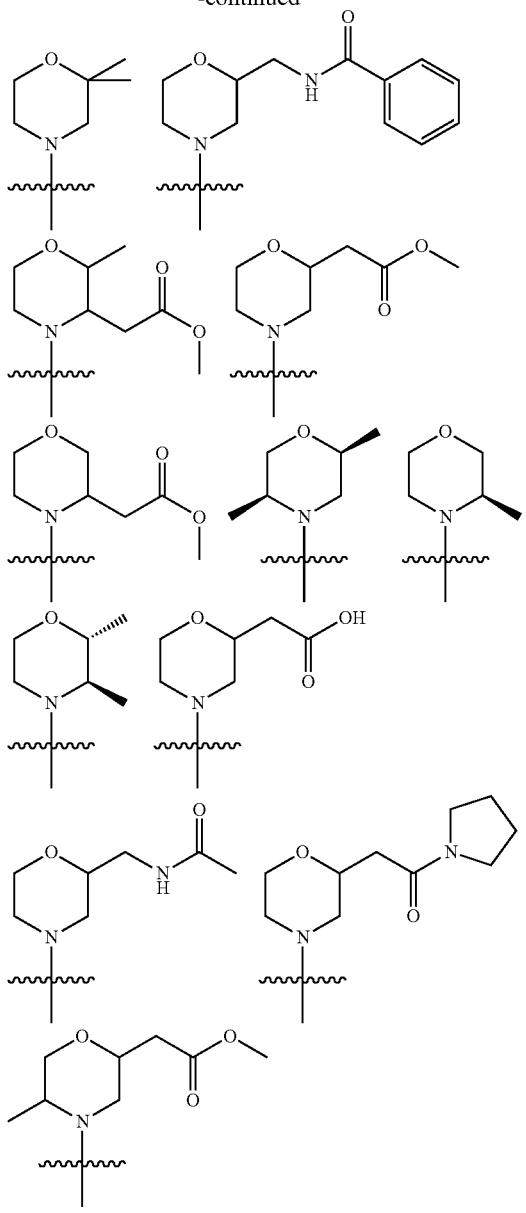

Further preferred compounds of the invention include those in which:

each $R^{10a}$, $R^{11a}$, $R^{10b}$, $R^{11b}$ and $R^{12a}$ independently represent, on each occasion when used herein, hydrogen or $C_{1-12}$ (e.g. $C_{1-6}$) alkyl (which latter group is optionally substituted by one or more substituents selected from =O and $E^{10}$); or any relevant pair of $R^{10a}$ and $R^{11a}$ and/or $R^{10b}$ and $R^{11b}$ may, when attached to the same nitrogen atom, be linked together to form (along with the requisite nitrogen atom to which they are attached) a 3- to 12- (e.g. 4- to 12-) membered ring, optionally containing one or more (e.g. one to three) double bonds, and which ring is optionally substituted by one or more substituents selected from $E^{12}$ and =O;

each $R^{11c}$ independently represents $C_{1-12}$ (e.g. $C_{1-6}$) alkyl (which latter group is optionally substituted by one or more substituents selected from =O and $E^{10}$);

each of $E^1$, $E^2$, $E^3$, $E^4$, $E^5$, $E^6$, $E^7$, $E^8$, $E^{10}$, $E^{11}$ and $E^{12}$ independently represents, on each occasion when used herein, $Q^4$ or $C_{1-6}$ alkyl (e.g. $C_{1-3}$) alkyl optionally substituted by one or more substituents selected from =O and $Q^5$;

each $Q^4$ and $Q^5$ independently represent halo, —CN, —$NO_2$, —$N(R^{20})R^{21}$, —$OR^{20}$, —C(=Y)—$R^{20}$, —C(=Y)—$OR^{20}$, —C(=Y)N($R^{20}$)$R^{21}$, —$N(R^{22})C(=Y)R^{21}$, —$N(R^{22})C$(=Y)$OR^{21}$, —$N(R^{22})C(=Y)N(R^{20})R^{21}$, —$NR^{22}S(O)_2R^{20}$, —$NR^{22}S(O)_2N(R^{20})R^{21}$, —$S(O)_2N(R^{20})R^{21}$, —$S(O)_2R^{20}$, —$SR^{20}$, —$S(O)R^{20}$ or $C_{1-6}$ alkyl optionally substituted by one or more fluoro atoms (and each $Q^5$ more preferably represents halo, such as fluoro); any two $E^1$, $E^2$, $E^3$, $E^4$, $E^5$, $E^6$, $E^7$, $E^8$, $E^{10}$, $E^{11}$ or $E^{12}$ groups may be linked together, but are preferably not linked together;

each $R^{20}$, $R^{21}$, $R^{22}$ and $R^{23}$ independently represent, on each occasion when used herein, aryl (e.g. phenyl; preferably unsubstituted, but which may be substituted by one to three $J^5$ groups) or, more preferably, hydrogen or $C_{1-6}$ (e.g. $C_{1-3}$) alkyl optionally substituted by one or more substituents selected from =O and $J^4$; or any pair of $R^{20}$ and $R^{21}$, may, when attached to the same nitrogen atom, be linked together to form a 4- to 8-membered (e.g. 5- or 6-membered) ring, optionally containing one further heteroatom selected from nitrogen and oxygen, optionally containing one double bond, and which ring is optionally substituted by one or more substituents selected from $J^6$ and =O;

each $R^{21a}$ independently represents $C_{1-6}$ (e.g. $C_{1-3}$) alkyl optionally substituted by one or more substituents selected from =O and $J^4$;

each $J^1$, $J^2$, $J^3$, $J^4$, $J^5$ and $J^6$ independently represent $C_{1-6}$ alkyl (e.g. acyclic $C_{1-3}$ alkyl or, e.g. in the case of $J^4$, $C_{3-5}$ cycloalkyl) optionally substituted by one or more substituents selected from =O and $Q^8$, or, more preferably, such groups independently represent a substituent selected from $Q^7$;

each $Q^7$ and $Q^8$ independently represents a substituent selected from fluoro, —$N(R^{50})R^{51}$, —$OR^{50}$, —C(=$Y^a$)—$R^{55}$, —C(=$Y^a$)—$OR^{50}$, —C(=$Y^a$)N($R^{50}$)$R^{51}$, —$NR^{52}S(O)_2R^{50}$, —$S(O)_2R^{50}$ or $C_{1-6}$ alkyl optionally substituted by one or more fluoro atoms;

each $R^{50}$, $R^{51}$, $R^{52}$ and $R^{53}$ substituent independently represents, on each occasion when used herein, hydrogen or $C_{1-6}$ (e.g. $C_{1-3}$) alkyl optionally substituted by one or more substituents selected from fluoro;

when any relevant pair of $R^{50}$, $R^{51}$ and $R^{52}$ are linked together, then those pairs that are attached to the same nitrogen atom may be linked together (i.e. any pair of $R^{50}$ and $R^{51}$), and the ring so formed is preferably a 5- or 6-membered ring, optionally containing one further nitrogen or oxygen heteroatom, and which ring is optionally substituted by one or more substituents selected from =O and $C_{1-3}$ alkyl (e.g. methyl);

$R^{60}$, $R^{61}$ and $R^{62}$ independently represent hydrogen or $Cl_3$ (e.g. $C_{1-2}$) alkyl optionally substituted by one or more fluoro atoms.

Preferred optional substituents on $R^3$ (and, possibly when they represent a substituent other than hydrogen on $R^1$, $R^{1a}$, $R^{1b}$ and $R^2$ groups) include:
—$N(R^{z9})$—$S(O)_2$—$R^{z10}$;
—$N(R^{z9})$—$S(O)_2$—$N(R^{z10})$; preferably
=O (e.g. in the case of alkyl, cycloalkyl or heterocycloalkyl groups);
—CN;
halo (e.g. fluoro, chloro or bromo);
$C_{1-6}$ alkyl, such as $C_{3-6}$ cycloalkyl or acyclic $C_{1-4}$ alkyl, which alkyl group may be cyclic, part-cyclic, unsaturated or, preferably, linear or branched (e.g. $C_{1-4}$ alkyl (such as ethyl, n-propyl, isopropyl, t-butyl or, preferably, n-butyl or methyl), all of which are optionally substituted with one or more halo (e.g. fluoro) groups (so forming, for example, fluoromethyl, difluoromethyl or, preferably, trifluoromethyl) or substituted with an aryl, heteroaryl or heterocycloalkyl group (which themselves may be substituted with one or more —$OR^{z1}$, —$C(O)R^{z2}$, —$C(O)OR^{z3}$, —$N(R^{z4})R^{z5}$, —$S(O)_2R^{z6}$, —$S(O)_2N(R^{z7})R^{z8}$; —$N(R^{z9})$—$C(O)$—$R^{z10}$, —$C(O)$—$N(R^{z11})Rz^{12}$ and/or —$N(R^{z9})$—$C(O)$—$N(R^{z10})$ substituents);

a 5- or 6-membered heterocycloalkyl group (optionally substituted with one or more —$OR^{z1}$, —$C(O)R^{z2}$, —$C(O)OR^{z3}$, —$N(R^{z4})R^{z5}$, —$S(O)_2R^{z6}$, —$S(O)_2N(R^{z7})R^{z8}$; —$N(R^{z9})$—$C(O)$—$R^{z10}$, —$C(O)$—$N(R^{z11})R^{z12}$ and/or —$N(R^{z11})$—$C(O)$—$N(R^{z10})$ substituents) (such heterocycloalkyl groups are preferably present on alkyl groups);

aryl (e.g. phenyl), if appropriate (e.g. when the substitutent is on an alkyl group, thereby forming e.g. a benzyl group);

—$OR^{z1}$;
—$C(O)R^{z2}$;
—$C(O)OR^{z3}$;
—$N(R^{z4})R^{z5}$;
—$S(O)_2R^{z6}$;
—$S(O)_2N(R^{z7})R^{z8}$;
—$N(R^{z9})$—$C(O)$—$R^{z10}$;
—$C(O)$—$N(R^{z11})R^{z12}$;
—$N(R^{z9})$—$C(O)$—$N(R^{z10})$;

wherein each $R^{z1}$ to $R^{z12}$ independently represents, on each occasion when used herein, H or $C_{1-4}$ alkyl (e.g. ethyl, n-propyl, t-butyl or, preferably, n-butyl, methyl, isopropyl or cyclopropylmethyl (i.e. a part cyclic alkyl group)) optionally substituted by one or more halo (e.g. fluoro) groups (so forming e.g. a trifluoromethyl group) or, may also be substituted by one aryl (e.g. phenyl) group (so forming e.g. a benzyl group). Further, any two $R^z$ groups (e.g. $R^{z4}$ and $R^{z5}$), when attached to the same nitrogen heteroatom may also be linked together to form a ring such as one hereinbefore defined in respect of corresponding linkage of $R^{10}$ and $R^{11}$ or $R^{10a}$ and $R^{11a}$ groups.

Preferred compounds of the invention include those in which:

$R^2$ represents hydrogen or a substituent selected from —$N(R^{10b})R^{11b}$ and, preferably, halo (e.g. chloro, bromo or iodo) and —CN;

$Q^1$ and $Q^{1b}$ independently represent halo, —CN, —$NO_2$, —$N(R^{10a})R^{11a}$, —$OR^{11a}$, —$C(=Y)N(R^{10a})R^{10b}$, —$C(=Y)$—$R^{10a}$, —$C(=Y)$—$OR^{10a}$, —$N(R^{12a})C(=Y)R^{11a}$, —$NR^{12a}C(=Y)OR^{11a}$, —$N(R^{12a})C(=Y)N(R^{10a})R^{11a}$, —$NR^{12a}S(O)_2R^{10a}$, —$NR^{12a}S(O)_2N(R^{10a})R^{11a}$ or —$S(O)_2N(R^{10a})R^{11a}$;

$Q^{1a}$ and $Q^2$ independently represent halo, —CN, —$NO_2$, —$N(R^{10a})R^{11a}$, —$OR^{10a}$, —$C(=Y)N(R^{10a})R^{10b}$, —$C(=Y)$—$R^{10a}$, —$C(=Y)$—$OR^{10a}$, —$N(R^{12a})C(=Y)R^{11a}$, —$N(R^{12a})C(=Y)OR^{11a}$, —$N(R^{12a})C(=Y)N(R^{10a})R^{11a}$, —$NR^{12a}S(O)_2R^{10a}$, —$NR^{12a}S(O)_2N(R^{10a})R^{11a}$, —$S(O)_2N(R^{10a})R^{11a}$ or heterocycloalkyl (optionally substituted by one or more (e.g. one) substituent selected from $E^8$);

$R^{10a}$, $R^{11a}$ and $R^{12a}$ independently represent hydrogen or $C_{1-6}$ (e.g. $C_{1-3}$) alkyl optionally substituted by one or more fluoro atoms;

$R^{11c}$ represents $C_{1-6}$ (e.g. $C_{1-3}$) alkyl optionally substituted by one or more fluoro atoms;

each $E^1$, $E^2$, $E^3$, $E^4$, $E^5$, $E^6$, $E^7$, $E^8$, $E^{10}$, $E^{11}$ and $E^{12}$ independently represents $C_{1-12}$ alkyl optionally substituted by one or more substituents selected from =O and $Q^5$, or, preferably (each $E^1$ to $E^{12}$ independently represent) $Q^4$;

each $R^{20}$, $R^{21}$, $R^{22}$ and $R^{23}$ (e.g. each $R^{20}$ and $R^{21}$) independently represents heteroaryl, preferably, aryl (e.g. phenyl) (which latter two groups are optionally substituted by one or more substituents selected from $J^5$), or, more preferably, hydrogen or $C_{1-6}$ (e.g. $C_{1-4}$) alkyl optionally substituted by one or more substituents selected from =O and $J^4$; or any relevant pair of $R^{20}$, $R^{21}$ and $R^{22}$ (e.g. $R^{20}$ and $R^{21}$) may (e.g. when both are attached to the same nitrogen atom) may be linked together to form a 3- to 8- (e.g. 4- to 8-) membered ring, optionally containing a further heteroatom, and optionally substituted by one or more substituents selected from =O and $J^6$;

$R^{21a}$ represents $C_{1-6}$ (e.g. $C_{1-4}$) alkyl optionally substituted by one or more substituents selected from =O and $J^4$;

each $J^1$, $J^2$, $J^3$, $J^4$, $J^5$ and $J^6$ independently represent $C_{1-6}$ alkyl (e.g. $C_{1-3}$ acyclic alkyl or $C_{3-5}$ cycloalkyl) optionally substituted by one or more substituents selected from $Q^8$, or, $J^1$ to $J^6$ more preferably represent a substituent selected from $Q^7$;

each $Q^7$ and $Q^8$ independently represent halo, —$N(R^{50})R^{51}$, —$OR^{50}$, —$C(=Y^a)$—$ORS^5$, —$C(=Y^a)$—$RO$, —$S(O)_2R^{50}$ or $C_{1-3}$ alkyl optionally substituted by one or more fluoro atoms;

each $R^{50}$, $R^{51}$, $R^{52}$ and $R^{53}$ independently represents hydrogen or $C_{1-6}$ (e.g. $C_{1-4}$) alkyl optionally substituted by one or more fluoro atoms;

each $R^{60}$, $R^{61}$ and $R^{62}$ independently represents hydrogen or $C_{1-2}$ alkyl (e.g. methyl).

More preferred compounds of the invention include those in which:

$Q^1$ and $Q^{1b}$ independently represent halo, —CN, —$NO_2$, —$N(R^{10a})R^{11a}$, —$OROa$, —$C(=Y)N(R^{10a})R^{10b}$, —$C(=Y)$—$R^{10a}$, —$C(=Y)$—$OR^{10a}$ or —$N(R^{12a})C(=Y)R^{11a}$.

$Q^{1a}$ and $Q^2$ independently represent halo, —CN, —$NO_2$, —$N(R^{10a})R^{11a}$, —$OR^{10a}$, —$C(=Y)N(R^{10a})R^{10b}$, —$C(=Y)$—$R^{10a}$, —$C(=Y)$—$OR^{10a}$, —$N(R^{12a})C(=Y)R^{11a}$ or heterocycloalkyl (optionally substituted by one or more (e.g. one) substituent selected from $E^8$);

$R^2$ represents hydrogen, chloro, bromo, iodo or —CN;

each $R^{10a}$, $R^{1a}$, $R^{1b}$, $R^{11b}$ and $R^{12a}$ independently represents hydrogen or $C_{1-4}$ (e.g. $C_{1-3}$) alkyl, which alkyl group may by substituted by one or more substituents selected from =O and $E^{10}$ (but which alkyl group is more preferably unsubstituted); or any relevant pair of $R^{10a}$ and $R^{11a}$ and/or $R^{10b}$ and $R^{11b}$, may be linked together to form a 5- or, preferably, a 6-membered ring, optionally containing a further heteroatom (preferably selected from nitrogen and oxygen), which ring is preferably saturated (so forming, for example, a piperazinyl or morpholinyl group), and optionally substituted by one or more substituents selected from =O and $E^{12}$ (which $E^{12}$ substituent may be situated on a nitrogen heteroatom; and/or $E^{12}$ is preferably halo (e.g. fluoro) or $C_{1-3}$ alkyl optionally substituted by one or more fluoro atoms);

each $E^1$, $E^2$, $E^3$, $E^4$, $E^5$, $E^6$, $E^7$, $E^8$, $E^{10}$, $E^{11}$ and $E^{12}$ independently represent $C_{1-4}$ alkyl optionally substituted by one or more $Q^5$ substituents, or, each of these preferably represent a substituent selected from $Q^4$;

$Q^4$ and $Q^5$ independently represent halo (e.g. fluoro), —$OR^{20}$, —$N(R^{20})R^{21}$, —$C(=Y)OR^{20}$, —$C(=Y)N(R^{20})R^{21}$, —$NR^{22}S(O)_2R^{20}$, heterocycloalkyl, aryl, heteroaryl (which latter three groups are optionally substituted with one or more substitutents selected from $J^2$ or $J^3$, as appropriate) and/or $C_{1-6}$alkyl (e.g. $C_{1-3}$ alkyl) optionally substituted by one or more fluoro atoms;

each Y represents, on each occasion when used herein, =S, or preferably =O;

each $R^{20}$, $R^{21}$, $R^{22}$ and $R^{23}$ (e.g. each $R^{20}$ and $R^{21}$) independently represents hydrogen or $C_{1-4}$(e.g. $C_{1-3}$) alkyl (e.g. tert-butyl, ethyl, methyl or a part cyclic group such as cyclopropylmethyl) optionally substituted (but preferably unsubstituted) by one or more (e.g. one) $J^4$ substituent(s); or any relevant pair of $R^{20}$, $R^{21}$ and $R^{22}$ (e.g. $R^{20}$ and $R^{21}$) may (e.g. when both are attached to the same nitrogen atom) may be linked together to form a 5- or, preferably, a 6-membered ring, optionally containing a further heteroatom (preferably selected from nitrogen and oxygen), which ring is preferably saturated (so forming, for example, a piperazinyl or morpholinyl group), and optionally substituted by one or more substituents selected from =O and $J^6$ (which $J^6$ substituent may be situated on a nitrogen heteroatom);

$R^{22}$ represents $C_{1-3}$ alkyl or, preferably, hydrogen;

each $J^1$, $J^2$, $J^3$, $J^4$, $J^5$ and $J^6$ independently represent a substituent selected from $Q^7$, or $J^1$ to $J^6$ (e.g. $J^4$) represents $C_{1-6}$ alkyl (e.g. $C_{3-5}$ cycloalkyl);

each $Q^7$ and $Q^8$ independently represent —C(=$Y^a$)—$OR^{50}$, —C(=$Y^a$)—$R^{50}$, —S(O)$_2R^{50}$ or $C_{1-3}$alkyl optionally substituted by one or more fluoro atoms;

each $Y^a$ independently represents =S or, preferably, =O;

each $R^{50}$ independently represents $C_{1-4}$ alkyl (e.g. tert-butyl or methyl).

Preferred $R^3$ groups of the compounds of the compounds of the invention include optionally substituted phenyl, indazolyl (e.g. 4-indazolyl), pyrimidinyl (e.g. 5-pyrimidinyl), azaindolyl (e.g. azaindol-5-yl), indolyl (e.g. 5-indolyl or 4-indolyl) and pyridyl (e.g. 3-pyridyl). Particularly preferred $R^3$ groups of the compounds of the compounds of the invention include optionally substituted pyridyl (e.g. 3-pyridyl) and, preferably, phenyl, indazolyl (e.g. 4-indazolyl) and pyrimidinyl (e.g. 5-pyrimidinyl).

Preferred compounds of the invention include those in which:

$R^2$ represents hydrogen or halo (e.g. chloro);

$R^3$ represents aryl (e.g. phenyl) or heteroaryl (e.g. a 5- or 6-membered monocyclic heteroaryl group or a 9- or 10-membered bicyclic heteroaryl group;

which groups may contain one to four, e.g. 3 or, preferably, 1 or 2, heteroatoms preferably selected from nitrogen, oxygen and sulfur) both of which are optionally substituted by one or more (e.g. two, or, preferably, one) substituent(s) selected from $E^7$ (e.g. —CF$_3$, preferably, —OH, —OC$_{1-6}$ alkyl (e.g. —OCH$_3$) and/or —N($R^{20}$)$R^{21}$ (e.g. —NH$_2$));

$E^1$ to $E^{12}$ independently represent $C_{1-6}$ (e.g. $C_{1-3}$, such as methyl) alkyl optionally substituted by one or more $Q^5$ substituents, or, preferably, $Q^4$;

$Q^4$ represents $C_{1-3}$ alkyl or, preferably, $Q^4$ represents —$OR^{20}$, —N($R^{20}$)$R^{21}$, —S(O)$_2R^{20}$, heterocycloalkyl (e.g. a 4- to 6-membered ring, containing preferably one or two heteroatoms selected from nitrogen and oxygen), aryl (e.g. phenyl; optionally substituted with two or, preferably, one substituent selected from $J^3$) or heteroaryl (e.g. a 5- or 6-membered monocyclic heteroaryl group preferably containing one or two heteroatoms preferably selected from nitrogen, oxygen and sulfur; which group may be substituted, but is preferably unsubstituted);

when $E^7$ represents $Q^4$, then $Q^4$ preferably represents —$OR^{20}$ or —N($R^2$)$R^{21}$;

when $E^8$ represents $Q^4$, then $Q^4$ preferably represents $C_{1-3}$ alkyl or, more preferably, —S(O)$_2R^{20}$;

when $E^{10}$ represents $Q^4$, then $Q^4$ preferably represents —$OR^{20}$, —S(O)$_2R^{20}$ or aryl (e.g. phenyl; which is preferably unsubstituted);

$Q^5$ represents halo (e.g. fluoro);

Y represents =O;

$R^{20}$ and $R^{21}$ independently represent hydrogen, $C_{1-3}$ alkyl (e.g. isopropyl or, preferably, methyl or ethyl), which latter group is optionally substituted by one or more (e.g. one) substituent(s) selected from $J^4$;

when there is a —N($R^{20}$)$R^{21}$ moiety present, then one of $R^{20}$ and $R^{21}$ represents hydrogen, and the other represents hydrogen or $C_{1-3}$ alkyl (e.g. methyl or ethyl), which latter group is optionally substituted by one or more (e.g. one) substituent(s) selected from $J^4$;

$J^3$ represents $Q^7$;

$J^4$ represents $Q^7$ or $C_{1-6}$ alkyl (such as $C_{3-6}$ alkyl, e.g. $C_{3-6}$ cycloalkyl);

$J^4$ more preferably represents $C_{1-6}$ alkyl, such as $C_{3-6}$ alkyl (especially $C_{3-6}$ cycloalkyl, such as cyclopropyl);

$Q^7$ represents —S(O)$_2R^{50}$ or aryl (e.g. phenyl) optionally substituted by one or more (e.g. one) substituents (e.g. at the 4-position) by —$OR^{60}$;

$Q^7$ more preferably represents —S(O)$_2R^{50}$;

when $J^3$ represents $Q^7$, then $Q^7$ preferably represents —S(O)$_2R^{50}$;

when $J^4$ represents $Q^7$, then $Q^7$ preferably represents aryl (e.g. phenyl) optionally substituted by one or more (e.g. one) substituents (e.g. at the 4-position) by —$OR^{60}$;

$R^{50}$ represents $C_{1-3}$ alkyl (e.g. methyl);

$R^{60}$ represents $C_{1-3}$ alkyl (e.g. methyl);

$B^1$, $B^{1a}$, $B^2$, $B^{2a}$, $B^3$, $B^{3a}$, $B^4$ and $B^{4a}$ independently represent $C_{1-6}$ (e.g. $C_{1-3}$) alkyl optionally substituted by halo, or, these groups preferably represent hydrogen.

Particularly preferred compounds of the invention include those in which:

$R^{1b}$ (when present) represents: a fragment of formula IA or, preferably, (i) $C_{1-12}$ (e.g. $C_{1-6}$) alkyl optionally substituted by one or more substituents selected from $Q^{1a}$; or (ii) heterocycloalkyl (linked to the requisite bicycle of formula I via a carbon atom) optionally substituted by one or more substituents selected from =O and $Q^{1b}$ (but preferably unsubstituted; the heterocycloalkyl group is preferably a 5- or, more preferably, 6-membered ring containing one or two (e.g. one) heteroatom(s) preferably selected from oxygen and nitrogen, for instance 4-piperidinyl or 4-tetrahydropyranyl);

$R^{1a}$ represents hydrogen, $C_{1-12}$ (e.g. $C_{1-6}$) alkyl optionally substituted by one or more substituents selected from =S, =N($R^{10a}$), preferably, =O and, more preferably, $Q^2$;

$Q^1$ (when present, although it is preferably not present) represents —C(=Y)N($R^{10a}$)$R^{10b}$ (and $Q^1$ preferably does not represent alkyl, heterocycloalkyl, aryl or heteroaryl);

$Q^{1a}$ and $Q^2$ independently represent —$OR^{10a}$, —N($R^{10a}$)$R^{11a}$ or heterocycloalkyl (e.g. a 7-, preferably, 5- or, more preferably, a 6-membered heterocycloalkyl group containing one or two heteroatoms preferably selected from nitrogen and oxygen, e.g. diazepanyl and, preferably, piperazinyl, piperidinyl, morpholinyl and tetrahydropyranyl), which is optionally substituted by one or more (e.g. one) substituent selected from $E^8$ (more preferably, $Q^2$ represents heterocycloalkyl as defined herein);

$Q^{1b}$ represents halo, —CN, —$OR^{10a}$ or —N(ROa)Ra (although $Q^{1b}$ is preferably not present);

$R^2$ represents hydrogen or halo (e.g. chloro);

m represents 1;

each $R^{15}$ independently represents H;

$R^a$ and $R^b$ are linked together to form a 5- or 6-membered ring (e.g. a 5-membered ring; preferably containing no further heteroatoms, e.g. a pyrrolidinyl group), which is fused to a second 5- or 6-membered (e.g. 5-membered) saturated heterocycloalkyl group (e.g. containing one heteroatom; e.g. a pyrrolidinyl group);

$R^3$ represents hydroxyphenyl (e.g. 3-hydroxyphenyl), methoxyphenyl (e.g. 3-methoxyphenyl), indazolyl (e.g. 4-indazolyl), pyrimidinyl (e.g. 5-pyrimidinyl, such as 2-amino-5-pyrimidinyl (i.e. 2-[-N($R^{20}$)($R^{21}$)]-pyrimidin-5-yl such as 2-NH$_2$-pyrimidin-5-yl or 2-[N(H)(CH$_2$-cyclopropyl)-pyrimidin-5-yl] or 2-methoxy-5-pyrimidinyl), azaindolyl (e.g. 7-azaindol-5-yl), indolyl (e.g. 5-indolyl or 4-indolyl, such as 5-fluoro-4-indolyl), pyridyl (e.g. 3-pyridyl, such as 6-NH$_2$-pyrid-3-yl, 5-OCH$_3$-pyrid-3-yl or 5-CF$_3$,6-NH$_2$-pyrid-3-yl) (other R$^3$ groups that may be mentioned include 2-[-N(H)—CH$_2$-(4-methoxyphenyl)]-pyrimidin-5-yl and 6-[-N(H)—CH$_2$-(4-methoxyphenyl)]-pyridin-3-yl);

Y represents =O;

Y$^a$ represents =O;

B$^1$, B$^{1a}$, B$^2$, B$^{2a}$, B$^3$, B$^{3a}$, B$^4$ and B$^{4a}$ independently represent hydrogen.

More preferred compounds of the invention (in particular those in which A$_1$ represents N, A$_4$ represents N, A$_{4a}$ represents C(R$^{1b}$) and A$_5$ represents C(R$^2$), but also other bicycles defined herein) include those in which:

R$^{1b}$ represents (i) C$_{1-4}$ (e.g. C$_{1-3}$) alkyl (e.g. cyclopropyl, isopropyl, ethyl or —CH$_3$) optionally substituted by one or more (e.g. one) substituent selected from Q$^{1a}$ (wherein the substituent may be at the terminal position of the alkyl group or otherwise, e.g. R$^{1b}$ may be ethyl substituted at the α-positon, i.e. —C(H)(Q$^{1a}$)—CH$_3$) or (ii) R$^{1b}$ represents a 5- or 6- (e.g. 6-) membered heterocycloalkyl group (preferably containing one heteroatom selected from nitrogen and oxygen, which is preferably at the para-position, so forming e.g. a 4-piperidinyl or 4-tetrahydropyranyl group), which group is preferably unsubstituted;

R$^2$ represents H or halo (e.g. chloro);

R$^3$ represents heteroaryl (e.g. a monocyclic 5- or preferably 6-membered heteroaryl group or a bicyclic 10- or, preferably, 9-membered heteroaryl group, in which there is one or two (e.g. two) heteroatoms present selected from sulfur, oxygen or, preferably, nitrogen, so forming for example a pyrimidinyl or indazolyl group), which is optionally substituted by one or more (e.g. one) substituent selected from E$^7$;

Q$^{1a}$ represents —OR$^{10a}$, —N(R$^{10a}$)R$^{11a}$ or heterocycloalkyl (e.g. a 5- or, preferably, a 6-membered heterocycloalkyl group containing one or two heteroatoms preferably selected from nitrogen and oxygen, e.g. piperazinyl, piperidinyl, morpholinyl and tetrahydropyranyl), which is optionally substituted by one or more (e.g. one) substituent selected from E$^8$;

Q$^{1b}$ represents halo, —CN, —OR$^{10a}$ or —N(R$^{10a}$)R$^{11a}$;

R$^{10a}$ represents H or C$_{1-3}$ alkyl (e.g. methyl) optionally substituted by one or more (e.g. one) E$^{10}$ group;

R$^{11a}$ represents H or, preferably, C$_{1-3}$ alkyl (e.g. ethyl) optionally substituted by one or more (e.g. one) E$^{10}$ group (e.g. —OR$^{20}$);

R$^{10a}$ and R$^{11}$ may be linked together to form a 5- or, preferably 6-membered ring (optionally containing one further heteroatom; in addition to the nitrogen heteroatom that is necessarily present), but preferably, R$^{10a}$ and R$^{11a}$ a are not linked together;

E$^7$ represents Q$^4$;

E$^8$ represents Q$^4$;

E$^{10}$ represents Q$^4$;

Q$^4$ represents —N(R$^{20}$)R$^{21}$ (e.g. —NH$_2$), —OR$^{20}$, —S(O)$_2$R$^{20}$ or aryl (e.g. phenyl, which is preferably unsubstituted);

R$^{20}$ represents H or C$_{1-3}$ alkyl (e.g. methyl);

R$^{21}$ represents H.

More preferred compounds of the invention (in particular those in which A$_1$ represents C(R$^1$), A$_4$ represents N, A$_{4a}$ represents C(R$^{1b}$) and A$_5$ represents C(R$^2$)) include those in which:

R$^1$ represents H;

R$^{1b}$ represents a fragment of formula IA or, more preferably, C$_{1-3}$ alkyl (e.g. —CH$_3$) optionally substituted by one or more (e.g. one) substituent selected from Q$^{1a}$;

R$^2$ represents halo (e.g. chloro) or, preferably, H;

m represents 1;

each R$^{15}$ independently represents H;

R$^a$ and R$^b$ are linked together to form a 5- or 6-membered ring (e.g. a 5-membered ring; preferably containing no further heteroatoms, e.g. a pyrrolidinyl group), which is fused to a second 5- or 6-membered (e.g. 5-membered) saturated heterocycloalkyl group (e.g. containing one heteroatom; e.g. a pyrrolidinyl group) so forming e.g. a hexahydro-pyrrolo-pyrrolyl group such as hexahydro-pyrrolo[3,4-c]pyrrol-2-yl;

R$^3$ represents aryl (e.g. phenyl) optionally substituted by one or more (e.g. one) substituents selected from E$^7$, or, R$^3$ may represent heteroaryl (e.g. a monocyclic 5- or preferably 6-membered heteroaryl group, in which there is one or two (e.g. two) heteroatoms present selected from sulfur, oxygen or, preferably, nitrogen, so forming for example a pyridyl or, preferablyl, a pyrimidinyl group such as 5-pyrimidinyl) optionally substituted by one or more (e.g. one) substituents selected from E$^7$ (which may be located at the 2-position of the pyrimidinyl group);

Q$^{1a}$ represents —N(R$^{10a}$)R$^{11a}$ or, preferably, —OR$^{10a}$ or heterocycloalkyl (e.g. a 7-, preferably, 5- or, more preferably, a 6-membered heterocycloalkyl group containing one or two heteroatoms preferably selected from nitrogen and oxygen, e.g. diazepanyl, morpholinyl or, preferably, piperazinyl), which is optionally substituted by one or more (e.g. one) substituent selected from E$^8$ (which E$^8$ substituent may be located on a nitrogen heteroatom);

Y represents =O;

E$^7$ represents Q$^4$;

E$^8$ represents C$_{1-3}$alkyl or, preferably, Q$^4$;

R$^{10a}$ represents H, C$_{1-3}$alkyl or heterocycloalkyl (e.g. a 7- or, preferably, 5- or more preferably 6-membered heterocycloalkyl group, e.g. containing one or two (e.g. one) heteroatoms in which one is preferably nitrogen, e.g. a diazepanyl group (e.g. [1,4]diazepany-1-yl), morpholinyl (e.g. 4-morpholinyl), piperazinyl (e.g. 1-piperazinyl), or, preferably, a piperidinyl group, such as 4-piperidinyl), which latter two groups are optionally substituted with one or more (e.g. one) substituent(s) selected from E$^{10}$ (which may be located on a nitrogen heteroatom of a heterocycloalkyl group);

R$^{10b}$ represents H or C$_{1-3}$ alkyl (e.g. methyl);

R$^{10a}$ more preferably represents H or C$_{1-3}$ alkyl (e.g. ethyl);

E$^{10}$ represents Q$^4$;

Q$^4$ represents C$_{1-3}$ alkyl or, preferably, —OR$^{20}$, —N(R$^{20}$)R$^{21}$ or —S(O)$_2$R$^{20}$;

when E$^7$ represents Q$^4$, Q$^4$ is preferably —N(R$^{20}$)R$^{21}$;

when E$^8$ represents Q$^4$, Q$^4$ is C$_{1-3}$ alkyl or, preferably, —S(O)$_2$R$^{20}$;

when E$^{10}$ represents Q$^4$, Q$^4$ is preferably —OR$^{20}$ or —S(O)$_2$R$^{20}$;

R$^{20}$ represents H or C$_{1-3}$ alkyl (e.g. isopropyl or, preferably, methyl) optionally substituted by one or more (e.g. one) substituents selected from J$^4$ (for instance, when Q$^4$ represents —N(R$^{20}$)R$^{21}$, then R$^{20}$ may represent substituted alkyl);

R$^{20}$ more preferably represents H or C$_{1-3}$ alkyl (e.g. isopropyl or, preferably, methyl);

R$^{21}$ represents H;

J$^4$ represents Q$^7$;

Q$^7$ represents aryl (e.g. phenyl) optionally substituted by one or more (e.g. one) substitutents (e.g. at the 4-position) by —OR$^{60}$;

R$^{60}$ represents C$_{1-3}$ alkyl (e.g. methyl).

More preferred compounds of the invention (in particular those in which $A_1$ represents N, $A_4$ represents $C(R^{1a})$, $A_{4a}$ represents N and $A_5$ represents $C(R^2)$) include those in which:
$R^{1x}$, if present, represent $C_{1-3}$ alkyl (e.g. methyl);
$R^{1a}$ represents $C_{1-3}$ alkyl (e.g. —CH$_3$) optionally substituted by one or more (e.g. one) substituent selected from $Q^2$ (but preferably unsubstituted);
$R^2$ represents H;
$R^3$ represents aryl (e.g. phenyl) or heteroaryl (e.g. a monocyclic 5- or preferably 6-membered heteroaryl group or a bicyclic 10- or, preferably, 9-membered heteroaryl group, in which there is one or two (e.g. two) heteroatoms present selected from sulfur, oxygen or, preferably, nitrogen, so forming for example a pyrimidinyl or indazolyl group), both of which are optionally substituted by one or more (e.g. one) substituent selected from $E^7$;
$Q^2$ represents heterocycloalkyl (e.g. a 5- or preferably 6-membered heterocycloalkyl group, containing one or two heteroatoms) optionally substituted by one or more (e.g. one) substituents selected from $E^8$ (which may be located on a heteroatom);
$E^7$ represents $Q^4$;
$E^8$ represents $Q^4$, in which $Q^4$ is preferably —S(O)$_2$R$^{20}$;
$Q^4$ represents —S(O)$_2$R$^{20}$ or, preferably, —N(R$^{20}$)R$^{21}$ or —OR$^{20}$;
$R^{20}$ represents H or $C_{1-3}$ alkyl (e.g. methyl);
$R^{21}$ represents H.

More preferred compounds of the invention (in particular those in which $A_1$ represents $C(R^1)$, $A_4$ represents $C(R^{1a})$, $A_{4a}$ represents N and $A_5$ represents N) include those in which:
$R^1$ represents hydrogen;
$R^{1a}$ represents $C_{1-3}$ alkyl (e.g. —CH$_3$) optionally substituted by one or more (e.g. one) substituent selected from $Q^2$ (but preferably unsubstituted) or $R^{1a}$ more preferably represents hydrogen;
$R^3$ represents aryl (e.g. phenyl) optionally substituted by one or more (e.g. one) substituent selected from $E^7$;
$E^7$ represents $Q^4$;
$Q^4$ represents —OR$^{20}$;
$R^{20}$ represents $C_{1-3}$ alkyl (e.g. methyl) or, preferably, H;
$R^{21}$ represents H.

More preferred compounds of the invention (in particular those in which $A_1$ represents N, $A_4$ represents $C(R^{1a})$, $A^{4a}$ represents $C(R^{1b})$ and $A_5$ represents N) include those in which:
when neither $R^{1a}$ nor $R^{1b}$ represent N, then $R^{1a}$ represents H;
$R^{1a}$ represents H;
$R^{1b}$ represents $C_{1-3}$ alkyl (e.g. —CH$_3$) optionally substituted by one or more (e.g. one) substituent selected from $Q^{1a}$;
$R^3$ represents aryl (e.g. phenyl) or heteroaryl (e.g. a monocyclic 5- or preferably 6-membered heteroaryl group, in which there is one or two (e.g. two) heteroatoms present selected from sulfur, oxygen or, preferably, nitrogen, so forming for example a pyrimidinyl group), both of which are optionally substituted by one or more (e.g. one) substituent selected from $E^7$ (and $R^3$ preferably represents optionally substituted monocyclic heteroaryl, such as pyrimidinyl);
$Q^{1a}$ represents heterocycloalkyl (e.g. a 5- or, preferably, a 6-membered heterocycloalkyl group containing one or two heteroatoms preferably selected from nitrogen and oxygen, e.g. piperazinyl), which is optionally substituted by one or more (e.g. one) substituent selected from $E^8$;
$E^7$ represents $Q^4$;
$E^8$ represents $Q^4$;
$Q^4$ represents —OR$^{20}$, —N(R$^{20}$)R$^{21}$ or —S(O)$_2$R$^{20}$;
$R^{20}$ represents H or, preferably, $C_{1-3}$ alkyl (e.g. methyl);
$R^{21}$ represents H.

More preferred compounds of the invention (in particular those in which $A_1$ represents N, $A_4$ represents $C(R^{1a})$, $A_{4a}$ represents N and $A_5$ represents $C(R^2)$) include those in which:
$R^{1a}$ represents $C_{1-3}$ alkyl (e.g. —CH$_3$) optionally substituted by one or more (e.g. one) substituent selected from $Q^2$;
$R^3$ represents aryl (e.g. phenyl) or heteroaryl (e.g. a monocyclic 5- or preferably 6-membered heteroaryl group, in which there is one or two (e.g. two) heteroatoms present selected from sulfur, oxygen or, preferably, nitrogen, so forming for example a pyrimidinyl group), both of which are optionally substituted by one or more (e.g. one) substituent selected from $E^7$ (and $R^3$ preferably represents optionally substituted aryl, such as phenyl);
$Q^2$ represents heterocycloalkyl (e.g. a 5- or, preferably, a 6-membered heterocycloalkyl group containing one or two heteroatoms preferably selected from nitrogen and oxygen, e.g. piperazinyl), which is optionally substituted by one or more (e.g. one) substituent selected from $E^8$;
$E^7$ represents $Q^4$;
$E^8$ represents $Q^4$;
$Q^4$ represents —OR$^{20}$, —N(R$^{20}$)R$^{21}$ or —S(O)$_2$R$^{20}$;
$R^{20}$ represents H or, preferably, $C_{1-3}$ alkyl (e.g. methyl);
$R^{21}$ represents H.

More preferred compounds of the invention (in particular those in which $A_1$ represents $C(R^1)$, $A_4$ represents $C(R^{1a})$, $A_{4a}$ represents N and $A_5$ represents $C(R^2)$) include those in which:
$R^1$ represents hydrogen;
$R^{1a}$ represents $C_{1-3}$ alkyl (e.g. —CH$_3$) optionally substituted by one or more (e.g. one) substituent selected from $Q^2$ (but preferably unsubstituted) or $R^{1a}$ more preferably represents hydrogen;
$R^2$ represents hydrogen;
$R^3$ represents aryl (e.g. phenyl) optionally substituted by one or more (e.g. one) substituent selected from $E^7$;
$E^7$ represents $Q^4$;
$Q^4$ represents —OR$^{20}$;
$R^{20}$ represents H or $C_{1-3}$ alkyl (e.g. methyl);
$R^{21}$ represents H.

Particularly preferred compounds of the invention include those of the examples described hereinafter.

Compounds of the invention may be made in accordance with techniques that are well known to those skilled in the art, for example as described hereinafter.

According to a further aspect of the invention there is provided a process for the preparation of a compound of formula I which process comprises:
(i) reaction of a compound of formula II,

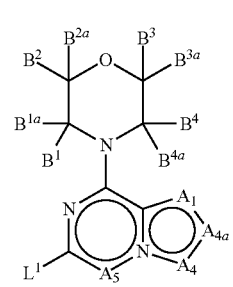

II wherein $L^1$ represents a suitable leaving group, such as iodo, bromo, chloro, a sulfonate group (e.g. —OS(O)$_2$CF$_3$, —OS(O)$_2$CH$_3$ or —OS(O)$_2$PhMe), or a sulfide group (e.g. —S—C$_{1-6}$ alkyl, such as —SCH$_3$) and $A_1$, $A_4$, $A_{4a}$, $A_5$, $B^1$, B1a, B², B²ᵃ, B³, B³ᵃ, B⁴ and B⁴ᵃ are as hereinbefore defined, with a compound of formula III, $$R^3\text{-}L^2 \qquad \text{III}$$

wherein L² represents a suitable group such as —B(OH)₂, —B(OR^{wx})₂ or —Sn(R^{wx})₃, in which each R^{wx} independently represents a C₁₋₆ alkyl group, or, in the case of —B(OR^{wx})₂, the respective R^{wx} groups may be linked together to form a 4- to 6-membered cyclic group (such as a 4,4,5,5-tetramethyl-1,3,2-dioxaborolan-2-yl group), thereby forming e.g. a pinacolato boronate ester group, (or L² may represent iodo, bromo or chloro, provided that L¹ and L² are mutually compatible) and R³ is as hereinbefore defined. The reaction may be performed, for example in the presence of a suitable catalyst system, e.g. a metal (or a salt or complex thereof) such as Pd, CuI, Pd/C, PdC₂, Pd(OAc)₂, Pd(Ph₃P)₂Cl₂, Pd(Ph₃P)₄ (i.e. palladium tetrakistriphenylphosphine), Pd₂(dba)₃ and/or NiCl₂ (preferred catalysts include palladium) and a ligand such as PdCl₂ (dppf).DCM, t-Bu₃P, (C₆H₁₁)₃P, Ph₃P, AsPh₃, P(o-Tol)₃, 1,2-bis(diphenylphosphino)ethane, 2,2'-bis(di-tert-butyl-phosphino)-1,1'-biphenyl, 2,2'-bis(diphenylphosphino)-1,1'-bi-naphthyl, 1,1'-bis(diphenyl-phosphino-ferrocene), 1,3-bis(diphenylphosphino)propane, xantphos, or a mixture thereof (preferred ligands include PdCl₂ (dppf).DCM), together with a suitable base such as, Na₂CO₃, K₃PO₄, Cs₂CO₃, NaOH, KOH, K₂CO₃, CsF, Et₃N, (i-Pr)₂NEt, t-BuONa or t-BuOK (or mixtures thereof; preferred bases include Na₂CO₃ and K₂CO₃) in a suitable solvent such as dioxane, toluene, ethanol, dimethylformamide, dimethoxyethane, ethylene glycol dimethyl ether, water, dimethylsulfoxide, acetonitrile, dimethylacetamide, N-methylpyrrolidinone, tetrahydrofuran or mixtures thereof (preferred solvents include dimethylformamide and dimethoxyethane). When L¹ represents a sulfide (e.g. —SCH₃), then an additive such as CuMeSal (copper(I) 3-methylsalicylate) or CuTC (copper(I)thiophene-2-carboxylate) may also be employed. The reaction may be carried out for example at room temperature or above (e.g. at a high temperature such as at about the reflux temperature of the solvent system). Alternative reaction conditions include microwave irradiation conditions, for example at elevated temperature, e.g. of about 130° C.;
(ii) reaction of a compound of formula IV,

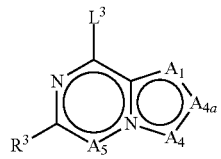

IV wherein L³ represents a suitable leaving group, such as one hereinbefore defined in respect of L¹ or a sulfone (e.g. —S(O)₂C₁₋₆alkyl moiety, such as —S(O)₂CH₃) or sulfide (e.g.—S—C₁₋₆ alkyl moiety, such as —SCH₃) and A₁, A₄, A₄ₐ, A₅ and R³ as hereinbefore defined, with a compound of formula V,

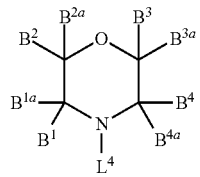

V wherein L⁴ may represent hydrogen (so forming an amine group), and B¹, B¹ᵃ, B², B²ᵃ, B³, B³ᵃ, B⁴ and B⁴ᵃ are as hereinbefore defined, and the reaction may optionally be performed in the presence of an appropriate metal catalyst (or a salt or complex thereof) such as Cu, Cu(OAc)₂, CuI (or CuI/diamine complex), copper tris(triphenylphosphine)bromide, Pd(OAc)₂, tris(dibenzylideneacetone)-dipalladium(0) (Pd₂(dba)₃) or NiCl₂ and an optional additive such as Ph₃P, 2,2'-bis(diphenylphosphino)-1,1'-binaphthyl, xantphos, NaI or an appropriate crown ether such as 18-crown-6-benzene, in the presence of an appropriate base such as NaH, Et₃N, pyridine, N,N'-dimethylethylenediamine, Na₂CO₃, K₂CO₃, K₃PO₄, Cs₂CO₃, t-BuONa or t-BuOK (or a mixture thereof, optionally in the presence of 4 Å molecular sieves), in a suitable solvent (e.g. dichloromethane, dioxane, toluene, ethanol, isopropanol, dimethylformamide, ethylene glycol, ethylene glycol dimethyl ether, water, dimethylsulfoxide, acetonitrile, dimethylacetamide, N-methylpyrrolidinone, tetrahydrofuran or a mixture thereof). This reaction may be performed at elevated temperature or under microwave irradiation reaction conditions, for example as described in process step (i). The compound of formula IV (e.g. in which L³ is chloro) may be prepared in situ, for example from a compound corresponding to a compound of formula IV, but in which L³ represents —OC₁₋₃ alkyl (e.g. methoxy) by reaction in the presence of e.g. a chlorinating agent (such as POCl₃);
(iii) for compounds of formula I in which (A⁵ represents C(R²) and) R² represents halo (e.g. bromo, iodo or chloro), reaction of a corresponding compound of formula I, in which R² represents hydrogen, with a reagent that is a source of halide ions (a halogenating reagent). For instance, an electrophile that provides a source of iodide ions includes iodine, diiodoethane, diiodotetrachloroethane or, preferably, N-iodosuccinimide, a source of bromide ions includes N-bromosuccinimide and bromine, and a source of chloride ions includes N-chlorosuccinimide, chlorine and iodine monochloride, for instance in the presence of a suitable solvent, such as CHCl₃ or an alcohol (e.g. methanol), optionally in the presence of a suitable base, such as a weak inorganic base, e.g. sodium bicarbonate. Typically, the reaction maybe performed by heating at a convenient temperature, either by conventional heating under reflux or under microwave irradiation;
(iv) for compounds of formula I in which R² (if present; i.e. if A⁵ represents C(R²)) represents a substituent other that hydrogen, or halo (e.g. bromo, iodo or chloro), reaction of a corresponding compound of formula I, in which R² represents halo (e.g. bromo, chloro or iodo), with a compound of formula VI, $$R^{2a}\text{-}L^7 \qquad \text{VI}$$

wherein R²ᵃ represents R² as hereinbefore described provided that it does not represent hydrogen or halo, and L⁷ represents a suitable leaving group such as one hereinbefore described in respect of L¹ or L² (see e.g. process step (i); reaction conditions such as those mentioned above may also be employed). Alternatively, the skilled person will appreciate that different reagents and reaction steps may be employed, depending on the particular R²ᵃ substituent required;
(v) for compounds of formula I in which A⁴ᵃ represents C(R¹ᵇ) and R¹ᵇ represents C₁₋₁₂ alkyl or heterocycloalkyl (which latter two groups are optionally substituted as hereinbefore defined) or R¹ᵃ is present, which represents —C(O)OR¹⁰ᵃ, halo, C₁₋₁₂ alkyl or heterocycloalkyl (which latter two groups are optionally substituted as hereinbefore defined; and hence a —C(O)H group is possible) may be prepared from corresponding compounds of formula I in which R¹ᵃ or R¹ᵇ (as appropriate) represents hydrogen, which may be reacted in the presence of a suitable base, such as an organometallic base (e.g. an organolithium base, such as t-, s- or n-butyllithium or, preferably a lithium amide base such as diisopropylamide; which deprotonates and/or lithiates at the relevant position), followed by reaction in the presence of an electrophile that is a source of halide ions (e.g. as described in respect of process step (iii)), or a compound of formula VII, $$L^8-R^{1b1} \qquad \text{VII}$$

wherein $L^8$ represents a suitable leaving group, such as one hereinbefore defined in respect of $L^1$ (or another suitable leaving group, such as $-N(CH_3)_2$), and $R^{1b1}$ represents $-C(O)OR^{10a}$ (and $R^{10a}$ is preferably not hydrogen), $C_{1-12}$ alkyl or heterocycloalkyl (which latter two groups are optionally substituted by one or more substituents as hereinbefore defined in respect of substituents on such alkyl or heterocycloalkyl groups; i.e. $R^{1b1}$ may represent $-C(O)H$, and hence the compound of formula VII may be dimethylformamide, which is employed to introduce the $-C(O)H$ group), under standard reaction conditions, for example the deprotonation/lithiation may be performed in an inert atmosphere (e.g. under $N_2$) in the presence of an anhydrous polar aprotic solvent (such as THF, dimethoxyethane, ethyl ether and the like), which may be performed at below room temperature (e.g. at below 0° C., at temperatures down to −78° C., depending on the strength of the base to be employed), and the subsequent 'quench', i.e. reaction with the electrophile (e.g. halide source or compound of formula VII) may also be performed at low temperatures (e.g. at the temperature of the deprotonation/lithiation), which temperature may be raised up to 0° C. (or to rt) to ensure the complete reaction, before the mixture is worked up;

(vi) for compounds of formula I which contain a $-C(OH)(H)-C_{1-11}$ alkyl group (which alkyl group may be substituted by one or more substituents selected from $E^3$ and $=O$; $Q^{1a}$; or $Q^2$, $=O$, $=S$ and $=N(R^{10a})$ as appropriate, but is preferably unsubstituted), for example when there is a $R^1$, $R^{1a}$, $R^{1b}$ and/or $R^2$ group present which represent such a $-C(OH)(H)-C_{1-11}$ alkyl group, reaction of a corresponding compound of formula I in which there is a $-C(O)H$ group present (i.e. $R^1$, $R^{1a}$, $R^{1b}$ and/or $R^2$ represents $-C(O)H$), with a compound of formula VIII, $$R^{xx}MgX^1 \qquad \text{VIII}$$

wherein $R^{xx}$ represents $C_{1-11}$ alkyl optionally substituted by one or more substituents selected from $E^3$ and $=O$ (but is preferably unsubstituted) and $X^1$ represents halo (e.g. iodo, bromo or, preferably, chloro), under standard Grignard reaction conditions, e.g. in the presence of an inert atmosphere and, optionally, an anhydrous solvent;

(vii) compounds of formula I in which $A_1$ and $A_4$ both represent N, $A_5$ represents $C(R^2)$ and $A_{4a}$ represents $C(R^{1b})$ may be prepared by reaction of a compound of formula IX,

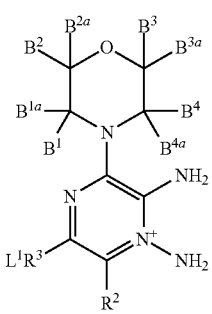

wherein $L^1R^3$ represents either $L^1$ as hereinbefore defined or $R^3$ as hereinbefore defined, and $R^2$, $B^1$, $B^{1a}$, $B^2$, $B^{2a}$, $B^3$, $B^{3a}$, $B^4$ and $B^{4a}$ are as hereinbefore defined, with a compound of formula X, $$H-C(O)-R^{1b} \qquad \text{X}$$

wherein $R^{1b}$ is as hereinbefore defined (and preferably represents hydrogen or $C_{1-12}$ alkyl optionally substituted as hereinbefore defined; hence the compound of formula X may be paraformaldehyde or another aldehyde), optionally in the presence of a suitable base (for instance a sterically hindered base, such as an amidine base, e.g. DBU) and a suitable solvent (e.g. dichloromethane) at an appropriate temperature (e.g. room temperature) for an appropriate period of time. When $L^1R^3$ in the compound of formula IX represents $L^1$, then this process step may be proceeded by process step (i) as defined above. Corresponding reactions may also take place in which $A_5$ represents N (instead of $C(R^2)$);

(viii) compounds of formula I in which $A_1$ represents N, $A_4$ represents $C(R^{1a})$, $A_{4a}$ represents N and $A_5$ represents $C(R^2)$ may be prepared by reaction of a compound of formula XI,

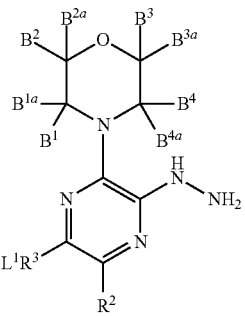

wherein $L^1R^3$, $R^2$, $B^1$, $B^{1a}$, $B^2$, $B^{2a}$, $B^3$, $B^{3a}$, $B^4$ and $B^{4a}$ are as hereinbefore defined, with a compound of formula XII, $$R^{1a}-C(OC_{1-6}alkyl)_3 \qquad \text{XII}$$

or, a compound of formula XIII, $$R^{1a}-C(O)OH \qquad \text{XIII}$$

or, derivatives of either, wherein $R^{1a}$ is as hereinbefore defined (and is preferably hydrogen or optionally substituted $C_{1-12}$ alkyl; so forming e.g. triethyl orthoformate, triethyl orthoacetate, formic acid, and the like), under standard reaction conditions. When $L^1R^3$ in the compound of formula XI represents $L^1$, then this process step may be proceeded by process step (i) as defined above. Corresponding reactions may also take place in which $A_5$ represents N (instead of $C(R^2)$).

Compounds of formula II may be prepared by reaction of a compound of formula XIV,

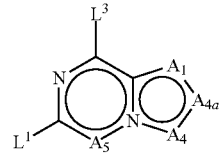

wherein $L^1$, $L^3$, $A_1$, $A_4$, $A_{4a}$, $A_5$ and $R^3$ are as hereinbefore defined, with a compound of formula V, as hereinbefore defined, for example under reaction conditions such as those hereinbefore described in respect of preparation of compounds of formula I (process step (ii) above).

Compounds of formula IV (for example, in which $A_1$ represents $C(R^1)$, $A_4$ represents $C(R^{1a})$, $A_{4a}$ represents $C(R^{1b})$ and $A_5$ represents $C(R^2)$) in which $L^3$ represents e.g. chloro, bromo or iodo, may be prepared by reaction of a compound of formula XV,

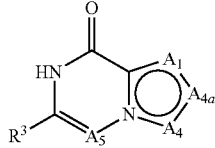

XV wherein $A_1$, $A_4$, $A_{4a}$, $A_5$ and $R^3$ as hereinbefore defined (or its tautomer), in the presence of a suitable reagent that provides the source of the chloro, bromo or iodo (e.g. $POCl_3$ may be employed, or, a reagent such as p-toluenesulfonyl chloride or the like) under reaction conditions known to the skilled person, for example at reflux (e.g. in the case of reaction with $POCl_3$) or, in the case of reaction with p-toluenesulfonyl chloride, in the presence of a base, such as an organic amine e.g. triethylamine, N,N-dimethylaniline (or the like), and optionally a catalyst such as DMAP (and optionally in the presence of a suitable solvent, such as acetonitrile). In the case of the latter, the compound of formula I may be prepared directly form the intermediate compound IV that may be formed by reaction in the presence of a compound of formula V (which latter reaction need not follow the reaction conditions set out above in respect of process step (ii); for instance, the reaction mixture may simply be heated in the same pot, e.g. at elevated temperature such as at about 65° C.

Compounds of formula IV in which $L^3$ represents a sulfonate, such as $-S(O)_2C_{1-6}$ alkyl (e.g. $-S(O)_2CH_3$) may be prepared by oxidation of a compound of formula XVI,

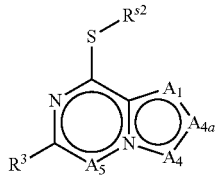

XVI wherein $R^{s2}$ represents $C_{1-6}$ alkyl (e.g. methyl), and $A^1$, $A_4$, $A_{4a}$, $A_5$ and $R^3$ are as hereinbefore defined, in the presence of an oxidising agent such as m-chloroperbenzoic acid and, if necessary, a suitable solvent (e.g. dichloromethane).

Compounds of formula IX (e.g. in which $L^1R^3$ represents $L^1$) may be prepared by reaction of a compound of formula XVII,

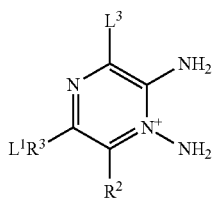

XVII wherein $L^1R^3$, $R^2$ and $L^3$ are as hereinbefore defined, with a compound of formula V as hereinbefore defined, for example under reaction conditions such as those hereinbefore defined in respect of preparation of compounds of formula I (process step (ii) above).

Compounds of formula IX and XVII may be prepared by reaction of a compound of formula XVIII,

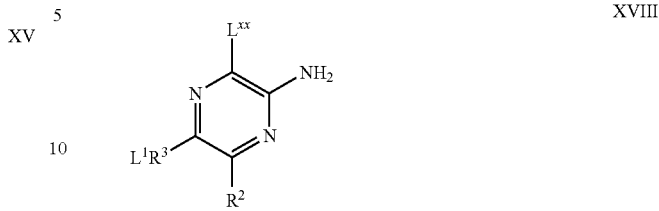

XVIII wherein $L^{xx}$ represents $L^3$ (in the case of preparation of compounds of formula XVII) or represents the following moiety:

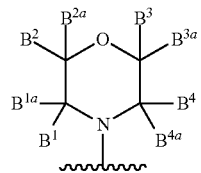

(in the case of preparation of compounds of formula IX), and $R^2$, $L^1R^3$, $B^1$, $B^{1a}$, $B^2$, $B^{2a}$, $B^3$, $B^{3a}$, $B^4$ and $B^{4a}$ are as hereinbefore defined, with o-(mesitylsulfonyl)hydroxylamine (or the like; i.e. another suitable source of $-NH_2$), under standard reaction conditions known to those skilled in the art, e.g. in the presence of a suitable solvent (e.g. dichloromethane).

Compounds of formula XI may be prepared by reaction of a compound of formula XIX,

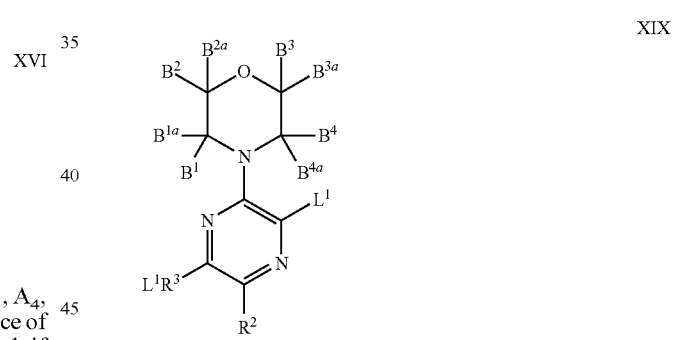

XIX wherein $L^1$, $R^2$, $L^1R^3$, $B^1$, $B^{1a}$, $B^2$, $B^{2a}$, $B^3$, $B^{3a}$, $B^4$ and $B^{4a}$ are as hereinbefore defined, with hydrazine (or a derivative thereof, e.g. hydrazine hydrate), under standard conditions.

Compounds of formula XIV in which $L^1$ represents a sulfide such as $-SCH_3$, $L^3$ represents a sulfide such as $-SCH_3$, and $A_1$ and $A_5$ both represent N, $A_4$ represents $C(R^{1a})$ and $A_{4a}$ represents $C(R^{1b})$ may be prepared by reaction of a compound of formula XX,

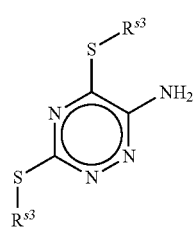

XX wherein $R^{s3}$ represents $C_{1-6}$ alkyl (preferably methyl), with a compound of formula XXI, $$L^{15}\text{-C(H)}(R^{1a})\text{—C(O)—}R^{1b} \qquad \text{XXI}$$

wherein $L^{15}$ represents a suitable leaving group, such as one hereinbefore defiend by $L^1$ (e.g. halo, such as bromo) and $R^{1a}$ and $R^{1b}$ are as hereinbefore defined, and $R^{1a}$ preferably represents hydrogen (or a protected derivative thereof; e.g. the compound of formula XXI may be bromoacetaldehyde diethyl acetal, or, when $R^{1b}$ represents —C(O)Oethyl, the compound of formula XXI may be ethyl bromopyruvate), for example in the presence of an acid catalyst (e.g. p-toluenesulfonic acid or the like), which reaction may be performed at room temperature or preferably at elevated temperature e.g. at about 65° C. Corresponding reactions may also take place in which $A_5$ represents $C(R^2)$.

Compounds of formula XIV in which $L^3$ represents halo (e.g. chloro) and $L^1$ represents a sulfide (e.g. —$SCH_3$) (and, preferably, $A_5$ represents N, $A_4$ represents $C(R^{1a})$, $A_{4a}$ represents $C(R^{1b})$ and $A_1$ represents N), may also be prepared by reaction of a compound of formula XXII,

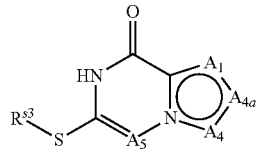

XXII wherein $A_1$, $A_4$, $A_{4a}$, $A_5$ and $R^5$ are as hereinbefore defined (and $R^{s3}$ represents a group defined by $R^{s2}$ and is preferably methyl), under halogenation reaction conditions such as those described herein, e.g. in the presence $POCl_3$.

Compounds of formula XIV in which $L^3$ represents halo (especially chloro) may be prepared by reaction of a compound of formula XXIII,

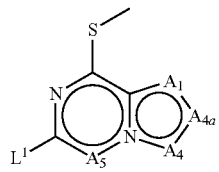

XXIII wherein $L^1$, $A_1$, $A_4$, $A_{4a}$ and $A_5$ are as hereinbefore defined, for example, in the presence of a base such as a metal hydroxide (e.g. KOH), in the presence of solvent (e.g. an alcohol such as methanol), followed by isolation of any intermediate product and then reaction under conditions such as those hereinbefore described in respect of preparation of compounds of formula IV (e.g. the conditions deployed in the reaction of a compound of formula XV in the presence of $POCl_3$, which reaction mixture may be heated at reflux for an appropriate period of time).

Compounds of formula XV may be prepared by reaction of a corresponding compound of formula XXIV,

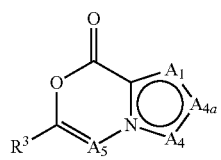

XXIV wherein $A_1$, $A_4$, $A_{4a}$, $A_5$ and $R^3$ as hereinbefore defined, in the presence of a suitable reagent for the replacement of the —O— moiety with a —N(H)— moiety, for example ammonia or a source thereof (e.g. ammonium acetate), under standard reaction conditions, for instance optionally in the presence of a suitable solvent (e.g. acetic acid), at elevated temperature (e.g. at about 160° C. under microwave irradiation reaction conditions).

Compounds of formula XV in which $A_5$ represents $C(R^2)$ (and preferably, $A_1$ represents $C(R^1)$, $A_4$ represents N, $A^{4a}$ represents $C(R^{1b})$ and $A_5$ represents C(H); further, $R^{1b}$ may represent —$C(O)OR^{10a}$) may also be prepared by reaction of a compound of formula XXV,

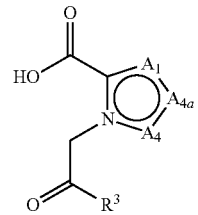

XXV or a derivative thereof (e.g. a carboxylic acid ester such as a —C(O)O-ethyl, for instance $A_{4a}$ may represent —$C(R^{1b})$, in which $R^{1b}$ represents —$C(O)OR^{10a}$ and $R^{10a}$ is preferably ethyl), wherein $A_1$, $A_4$, $A_{4a}$ and $R^3$ are as hereinbefore defined (but, preferably, $A_1$ represents $C(R^1)$, $A_4$ represents N and $A_{4a}$ represents $C(R^{1b})$, in which $R^{1b}$ may represent —C(O)$ORO^{10a}$), with a source of ammonia, such as ammonium acetate, for example under reaction conditions such as those described herein (e.g. above). The skilled person will appreciate that $R^2$ may represent hydrogen or an $R^2$ substituent may be pending on the —$CH_2$— moiety bridging the $R^3$—C(O)— moiety and the N of the 5-membered heterocycle.

Compounds of formula XV, or protected derivatives thereof (which includes salts, e.g. a bromide salt), in which $A_5$ represents $C(R^2)$ (and, preferably, $A_{4a}$ represents N and/or, preferably, $A_1$ represents $C(R^1)$ and $A_4$ represents $C(R^{1a})$) may be prepared by reaction of a compound of formula XXVI,

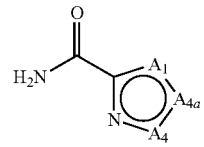

XXVI or a protected derivative thereof, e.g. a methyl protected derivative thereof, for instance, when the $A_1$ to $A_{4a}$-containing ring represents an imidazole ring (i.e. $A_{4a}$ represents N, and the other ring members are C, then the N at $A_{4a}$ may be protected, e.g. by a methyl group, so forming for example 1-methyl-1H-imidazole-4-carboxamide) and wherein $A_1$, $A_4$ and $A_{4a}$ are as hereinbefore defined, with a compound of formula XXVII, $$L^{12}\text{-C(H)}(R^2)\text{—C(O)—}R^3 \qquad \text{XXVII}$$

wherein $L^{12}$ represents a suitable leaving group, such as one hereinbefore defined in respect of $L^1$ (e.g. halo, preferably, bromo), and $R^2$ and $R^3$ are as hereinbefore defined (and $R^2$ is preferably hydrogen), for example at elevated temperature (e.g. at reflux) in the presence of an appropriate solvent (e.g. acetonitrile, dimethylformamide, and the like, or mixtures thereof).

Compounds of formula XV, in which $A_5$ represents N (e.g. $A_1$, $A_4$ and $A_{4a}$ respectively represent $C(R^1)$, $C(R^{1a})$ and $C(R^{1b})$ and $A_5$ represents N, or, $A_1$ represents $N(R^{1x})$, $A_4$ represents $C(R^{1a})$ and $A_{4a}$ and $A_5$ both represent N) may also be prepared by intramolecular cyclisation of a compound of formula XXVIII,

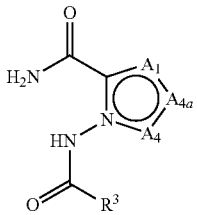

XXVIII wherein $R^3$, $A_1$, $A_4$ and $A_{4a}$ are as hereinbefore defined, by reaction in the presence of a base, for instance an aqueous basic solution such as ammonium hydroxide, or a metal alkyl-oxide (e.g. potassium tert-butoxide) in an alcoholic solution (e.g. butanol), for instance at elevated temperature e.g. at about 120° C. under microwave irradiation reaction conditions.

Compounds of formula XV, in which $R^3$ is replaced with a —OH group and $A_5$ represents N (e.g. $A_1$, $A_4$ and $A_{4a}$ respectively represent $C(R^1)$, $C(R^{1a})$ and $C(R^{1b})$ and $A_5$ represents N, or, $A_1$ represents $N(R^{1x})$, $A_4$ represents $C(R^{1a})$ and $A_{4a}$ and $A_5$ both represent N) may also be prepared by reaction of a compound of formula XXIX,

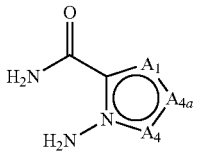

XXIX wherein $A_1$, $A_4$ and $A_{4a}$ are as hereinbefore defined, with phosgene, triphosgene, carbonyl diimidazole, or the like, i.e. another suitable reagent that acts as a similar source of a carbonyl group, under reaction conditions such as those described hereinafter. Such amido-compounds may be prepared by coupling of the corresponding carboxylic acid with ammonia (or a suitable source thereof, e.g. $NH_4Cl$ in $NH_3$/MeOH).

Compounds of formula XVI may be prepared by reaction of a compound of formula XXX,

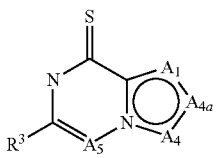

XXX wherein $A_1$, $A_4$, $A_{4a}$, $A_5$ and $R^3$ are as hereinbefore defined, with a compound of formula XXXI, $$R^{s2}\text{-}L^{13}$$

XXXI wherein $L^{13}$ represents a suitable leaving group (such as halo, e.g. iodo) and $R^{s2}$ is as hereinbefore defined (e.g. methyl iodide), for example in the presence of aqueous NaOH solution and an alcoholic solvent (e.g. methanol).

Compounds of formula XVI may also be prepared by intramolecular reaction of a compound of formula XXXII,

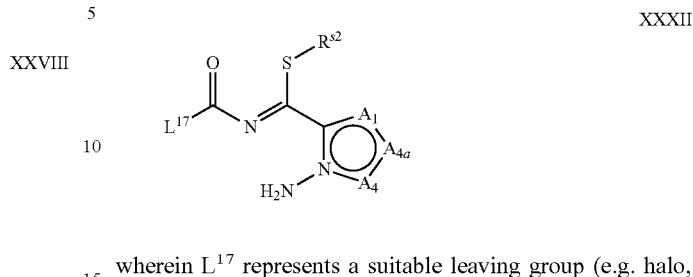

XXXII wherein $L^{17}$ represents a suitable leaving group (e.g. halo, such as chloro) (or $L^{17}$ may represent $R^3$), $A_1$ is preferably N, $A_4$ is $C(R^{1a})$ and $A_5$ is $C(R^{1b})$, for example in the presence of base at elevated temperature.

Compounds of formula XVII may be prepared by reaction of a compound of formula XXXIII,

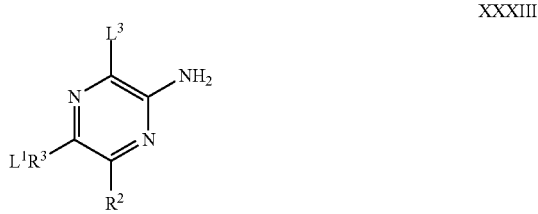

XXXIII wherein $R^2$, $L^1R^3$ and $L^3$ are as hereinbefore defined, with a suitable aminating agent, for instance a hydroxylamine compound (e.g. a sulfonyl-hydroxylamine, such as o-(meistylsulfonyl)hydroxylamine), under standard reaction conditions.

Compounds of formula XIX in which $L^1$ represents chloro (or halo) may be prepared by reaction of a compound of formula XXXIV,

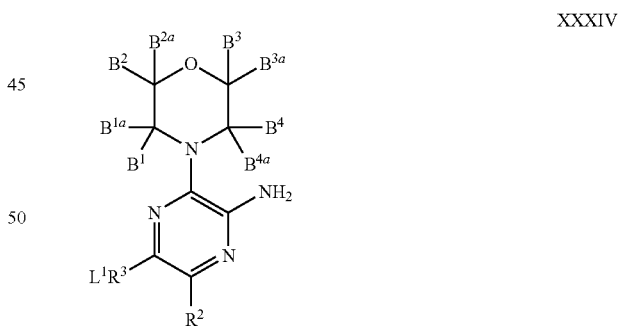

XXXIV wherein $L^1R^3$, $R^2$, $B^1$, $B1a$, $B^2$, $B^{2a}$, $B^3$, $B^{3a}$, $B^4$ and $B^{4a}$ are as hereinbefore defined, with a reagent, or mixture of reagents, that are suitable for converting the amino moiety to a chloro (or other halo) moiety, for example, $TiCl_4$ and tert-butyl nitrite, nuder conditions such as those described hereinafter.

Compounds of formula XXII in which $A_5$ represents N (and preferably in which $A_5$ represents N, $A_4$ represents $C(R^{1a})$, $A_{4a}$ represents $C(R^{1b})$ and $A_1$ represents N) may be prepared by reaction of a compound of formula XXXV,

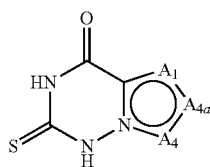

XXXV wherein $A_1$, $A_4$ and $A_{4a}$ are as hereinbefore defined (but, preferably, $A_4$ represents $C(R^{1a})$, $A_{4a}$ represents $C(R^{1b})$ and $A_1$ represents N), in the presence of a compound of formula XXXI as hereinbefore defined but in which $R^{s2}$ represents $R^3$.

Compounds of formula XXIV in which in which $A_5$ represents $C(R^2)$ (and, preferably, $A_1$ represents $C(R^1)$, $A_4$ represents $C(R^{1a})$, $A_{4a}$ represents $C(R^{1b})$ and $A_5$ represents $C(H)$), may be prepared by reaction of a compound of formula XXXVI,

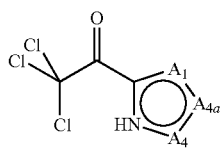

XXXVI wherein $A_1$, $A_4$ and $A_{4a}$ are as hereinbefore defined, with a compound of formula XXXVII

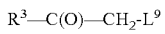 XXXVII wherein $L^9$ represents a suitable leaving group, for example one hereinbefore defined in respect of $L^1$ (e.g. halo, and preferably, bromo), under standard reaction conditions, for example, optionally in the presence of a suitable base (preferably an inorganic base, such as NaH, $K_3PO_4$, $Cs_2CO_3$, t-BuONa, t-BuOK, and, more preferably an inorganic carbonate such as $Na_2CO_3$ and, preferably, $K_2CO_3$) and a suitable solvent (e.g. an aprotic solvent such as dichloromethane or, preferably, acetone). The reaction may be performed at elevated temperature, for example, at above 100° C. (e.g. at about 120° C.) under microwave irradiation conditions.

Compounds of formula XXV may be prepared by reaction of a compound of formula XXXVIII,

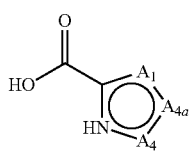

XXXVIII or a derivative thereof (e.g. ester such as ethyl ester), wherein $A_1$, $A_4$ and $A_{4a}$ are as hereinbefore defined, with a compound of formula XXXIX,

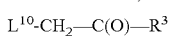 XXXIX wherein $L^{10}$ represents a suitable leaving group, such as one hereinbefore defined in respect of $L^1$ (e.g. halo, such as bromo), and $R^3$ is as hereinbefore defined, under standard reaction conditions, for example optionally in the presence of a suitable base and solvent (such as those hereinbefore described in respect of preparation of compounds of formula XXIV (by reaction of a compound of formula XXXVI and XXXVII), e.g. $K_2CO_3$ in acetone).

Compounds of formula XXVI may be prepared by reaction of a compound of formula XXXVIII as hereinbefore defined, or a derivative thereof (e.g. an ester, such as an ethyl ester), with ammonia or a suitable source thereof (e.g. $NH_4Cl$ in a solution of $NH_3$ in an alcohol such as methanol).

Compounds of formula XXVIII may be prepared by reaction of a compound of formula XXIX as hereinbefore defined with a compound of formula XL, $R^3$—C(O)-$L^{11}$  XL wherein $L^{11}$ represents a suitable leaving group such as one hereinbefore defined by $L^1$ (e.g. halo, such as chloro) or —OH (or an ester, thereof) under standard acylation or amide coupling reaction conditions, e.g. in the case of acylation, the presence of an appropriate base (e.g. an organic amine base such as triethylamine) and an appropriate solvent (e.g. pyridine, dichloromethane, dioxane, etc, or mixtures thereof), or, in the case of amide couplings, under conditions described hereinafter (or e.g. in the presence of polyphosphoric acid, which advantageously may form a compound of formula XXVIII in situ, which may undergo subsequent reaction to provide the compound of formula XV isoquinolinone directly).

Compounds of formula XXIX may be prepared by (partial) hydrolysis of a compound of formula XLI,

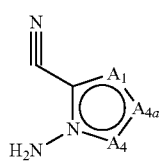

XLI wherein $A_1$, $A_4$ and $A_{4a}$ are as hereinbefore defined, under standard hydrolysis reaction conditions, e.g. in the presence of an aqueous hydroxide base (e.g. potassium hydroxide) in a suitable solvent such as tetrahydrofuran.

Compounds of formula XXIX (or the corresponding carboxylic acid or ester) may also be prepared by amination of a compound of formula XXVI as hereinbefore defined, or compounds of formula XLI may also be prepared by amination of a compound of formula XLII,

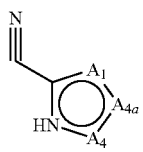

XLII wherein $A_1$, $A_4$ and $A_{4a}$ are as hereinbefore defined, under reaction conditions such as those described hereinafter, e.g. in the presence of sodium hydride, followed by o-(diphenylphosphinyl)hydroxylamine.

Compounds of formula XXXIX in which $L^{10}$ represents halo (e.g. chloro or, preferably, bromo) may be prepared by reaction of a compound corresponding to a compound of formula XXXIX but in which $L^{10}$ represents hydrogen, with a source of halide ions (e.g. such as one hereinbefore described in respect of preparation of compounds of formula I; process step (iii) above), such as N-chlorosuccinimide or N-bromosuccinimide, under standard reaction conditions e.g.

in the presence of a suitable base (such as an organic base e.g. triethylamine or the like) and trimethylsilylfluoromethanesulfonate, or the like.

Compounds corresponding to compounds of formula XXXIX but in which $L^{10}$ represents hydrogen may themselves be prepared from compounds of formula XLIII, $$R^3-L^{11} \qquad \text{XLIII}$$

in which $L^{11}$ represents a suitable leaving group, such as one hereinbefore defined in respect of $L^1$ (e.g. halo, such as chloro or, preferably bromo), with a compound that allows the introduction of the —C(O)CH$_3$ moiety, such as tributyl(1-ethoxyvinyl)tin in the presence of a precious metal catalyst/ligand (e.g. dichlorobis(triphenyl-phosphine)palladium (II)) and a suitable solvent (e.g. dimethylformamide, or the like).

Compounds of formula XLI may be prepared by reaction of a compound of formula XLII as hereinbefore defined, for example by reaction in the presence of base (e.g. a metal hydride, such as sodium hydride) and an appropriate reagent for the introduction of the amino group, e.g. o-(diphenylphosphinyl)-hydroxylamine, or another reagent suitable for electrophilic aminations, under reaction conditions such as those described hereinafter.

Compounds of formula XLII may be prepared by reaction of a compound of formula XLIV,

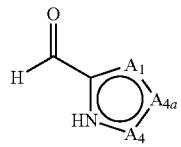

XLIV wherein $A_1$, $A_4$ and $A_{4a}$ are as hereinbefore defined, in the presence of hydroxylamine (e.g. the hydrochloride thereof), followed by dehydration (in the presence of a suitable dehydrating agent, such as phthalic anhydride).

Other specific transformation steps (including those that may be employed in order to form compounds of formula I) that may be mentioned include:

(i) reductions, for example of a carboxylic acid (or ester) to either an aldehyde or an alcohol, using appropriate reducing conditions (e.g. —C(O)OH (or an ester thereof), may be converted to a —C(O)H or —CH$_2$—OH group, using DIBAL and LiAlH$_4$, respectively (or similar chemoselective reducing agents));

(ii) reductions of an aldehyde (—C(O)H) group to an alcohol group (—CH$_2$OH), using appropriate reduction conditions such as those mentioned at point (i) above;

(iii) oxidations, for example of a moiety containing an alcohol group (e.g. —CH$_2$OH) to an aldehyde (e.g. —C(O)H), for example in the presence of a suitable oxidising agent, e.g. MnO$_2$ or the like;

(iv) reductive amination of an aldehyde and an amine, under appropriate reaction conditions, for example in "one-pot" procedure in the presence of an appropriate reducing agent, such as a chemoselective reducing agent such as sodium cyanoborohydride or, preferably, sodium triacetoxyborohydride, or the like.

Alternatively, such reactions may be performed in two steps, for example a condensation step (in the presence of e.g. a dehydrating agent such as trimethyl orthoformate or MgSO$_4$ or molecular sieves, etc) followed by a reduction step (e.g. by reaction in the presence of a reducing agent such as a chemoselective one mentioned above or NaBH$_4$, AlH$_4$, or the like);

(v) amide coupling reactions, i.e. the formation of an amide from a carboxylic acid (or ester thereof), for example when $R^2$ represents —C(O)OH (or an ester thereof), it may be converted to a —C(O)N($R^{10b}$)$R^{11b}$ group (in which $R^{10b}$ and $R^{11b}$ are as hereinbefore defined, and may be linked together, e.g. as defined above), and which reaction may (e.g. when $R^2$ represents —C(O)OH) be performed in the presence of a suitable coupling reagent (e.g. 1,1'-carbonyldiimidazole, N,N'-dicyclohexylcarbodiimide, or the like) or, in the case when $R^2$ represents an ester (e.g. —C(O)OCH$_3$ or —C(O)OCH$_2$CH$_3$), in the presence of e.g. trimethylaluminium, or, alternatively the —C(O)OH group may first be activated to the corresponding acyl halide (e.g. —C(O)Cl, by treatment with oxalyl chloride, thionyl chloride, phosphorous pentachloride, phosphorous oxychloride, or the like), and, in all cases, the relevant compound is reacted with a compound of formula HN($R^{10a}$)$R^{11a}$ (in which $R^{10a}$ and $R^{11a}$ are as hereinbefore defined), under standard conditions known to those skilled in the art (e.g. optionally in the presence of a suitable solvent, suitable base and/or in an inert atmosphere);

(vi) conversion of a primary amide to a nitrile functional group, for example under dehydration reaction conditions, e.g. in the presence of POCl$_3$, or the like;

(vii) nucleophilic substitution reactions, where any nucleophile replaces a leaving group, e.g. methylsulfonylpiperazine may replace a chloro leaving group, or, aromatic nucleophilic substitution reactions such as the substitution of ammonia (or a protected derivative thereof, e.g. a dibenzyl derivative) onto an aromatic group bearing a leaving group (e.g. onto a 2-chloropyrimidinyl moiety);

(viii) transformation of a methoxy group to a hydroxy group, by reaction in the presence of an appropriate reagent, such as boron fluoride-dimethyl sulfide complex or BBr$_3$ (e.g. in the presence of a suitable solvent such as dichloromethane);

(ix) specific deprotection steps, for example a hydroxy group protected as a silyl ether (e.g. a tert-butyl-dimethylsilyl protecting group) may be deprotected by reaction with a source of fluoride ions, e.g. by employing the reagent tetrabutylammonium fluoride (TBAF).

Intermediate compounds described herein are either commercially available, are known in the literature, or may be obtained either by analogy with the processes described herein, or by conventional synthetic procedures, in accordance with standard techniques, from available starting materials using appropriate reagents and reaction conditions. Further, processes to prepare compounds of formula I may be described in the literature, for example in:

Werber, G. et al.; *J. Heterocycl. Chem.; EN;* 14; 1977; 823-827;

Andanappa K. Gadad et al. *Bioorg. Med. Chem.* 2004, 12, 5651-5659;

Paul Heinz et al. *Monatshefte für Chemie,* 1977, 108, 665-680;

M. A. El-Sherbeny et al. *Boll. Chim. Farm.* 1997, 136, 253-256;

Nicolaou, K. C.; Bulger, P. G.; Sarlah, D. *Angew. Chem. Int. Ed.* 2005, 44, 2-49;

Bretonnet et al. *J. Med. Chem.* 2007, 50, 1872;

Asunción Marin et al. *Farmaco* 1992, 47 (1), 63-75;

Severinsen, R. et al. *Tetrahedron* 2005, 61, 5565-5575;

Nicolaou, K. C.; Bulger, P. G.; Sarlah, D. *Angew. Chem. Int. Ed.* 2005, 44, 2-49;

M. Kuwahara et al., *Chem. Pharm Bull.,* 1996, 44, 122;

Wipf, P.; Jung, J.-K. *J. Org. Chem.* 2000, 65(20), 6319-6337;

Shintani, R.; Okamoto, K. *Org. Lett.* 2005, 7 (21), 4757-4759;
Nicolaou, K. C.; Bulger, P. G.; Sarlah, D. *Angew. Chem. Int. Ed.* 2005, 44, 2-49;
J. Kobe et al., *Tetrahedron,* 1968, 24, 239;
P. F. Fabio, A. F. Lanzilotti and S. A. Lang, *Journal of Labelled Compounds and Pharmaceuticals,* 1978, 15, 407;
F. D. Bellamy and K. Ou, *Tetrahedron Lett.,* 1985, 25, 839;
M. Kuwahara et al., *Chem. Pharm Bull.,* 1996, 44, 122;
A. F. Abdel-Magid and C. A Maryanoff. *Synthesis,* 1990, 537;
M. Schlosser et al. *Organometallics in Synthesis. A Manual,* (M. Schlosser, Ed.),
Wiley &Sons Ltd: Chichester, UK, 2002, and references cited therein;
L. Wengwei et al., *Tetrahedron Lett.,* 2006, 47, 1941;
M. Plotkin et al. *Tetrahedron Lett.,* 2000, 41, 2269;
Seyden-Penne, *J. Reductions by the Alumino and Borohydrides*, VCH, NY, 1991;
O. C. Dermer, *Chem. Rev.,* 1934, 14, 385;
N. Defacqz, et al., *Tetrahedron Lett.,* 2003, 44, 9111;
S. J. Gregson et al., *J. Med. Chem.,* 2004, 47, 1161;
A. M. Abdel Magib, et al., *J. Org. Chem.,* 1996, 61, 3849;
A. F. Abdel-Magid and C. A Maryanoff. *Synthesis,* 1990, 537;
T. Ikemoto and M. Wakimasu, *Heterocycles,* 2001, 55, 99;
E. Abignente et al., *II Farmaco,* 1990, 45, 1075;
T. Ikemoto et al., *Tetrahedron,* 2000, 56, 7915;
T. W. Greene and P. G. M. Wuts, *Protective Groups in Organic Synthesis*, Wiley, NY, 1999;
S. Y. Han and Y.-A. Kim. *Tetrahedron,* 2004, 60, 2447;
J. A. H. Lainton et al., *J. Comb. Chem.,* 2003, 5, 400; or
Wiggins, J. M. *Synth. Commun.,* 1988, 18, 741.

The substituents $R^3$, $B^1$, $B^{1a}$, $B^2$, $B^{2a}$, $B^3$, $B^{3a}$, $B^4$, $B^{4a}$, $A_1$, $A_4$, $A_{4a}$ and $A_5$ in final compounds of the invention or relevant intermediates may be modified one or more times, after or during the processes described above by way of methods that are well known to those skilled in the art. Examples of such methods include substitutions, reductions, oxidations, alkylations, acylations, hydrolyses, esterifications, etherifications, halogenations or nitrations. Such reactions may result in the formation of a symmetric or asymmetric final compound of the invention or intermediate. The precursor groups can be changed to a different such group, or to the groups defined in formula I, at any time during the reaction sequence.

For example, when substituents in the compounds of the invention (e.g. represented by $R^3$, $B^1$, $B^{1a}$, $B^2$, $B^{2a}$, $B^{3a}$, $B^4$, $B^{4a}$, $A_1$, $A_4$, $A_{4a}$ and $A_5$) such as $CO_2Et$, CHO, CN and/or $CH_2Cl$, are present, these groups can be further derivatized to other fragments described (e.g. by those integers mentioned above) in compounds of the invention, following synthetic protocols very well know to the person skilled in the art and/or according to the experimental part described in the patent. Other specific transformation steps that may be mentioned include: the reduction of a nitro or azido group to an amino group; the hydrolysis of a nitrile group to a carboxylic acid group; and standard nucleophilic aromatic substitution reactions, for example in which an iodo-, preferably, fluoro- or bromo-phenyl group is converted into a cyanophenyl group by employing a source of cyanide ions (e.g. by reaction with a compound which is a source of cyano anions, e.g. sodium, copper (I), zinc or potassium cyanide, optionally in the presence of a palladium catalyst) as a reagent (alternatively, in this case, palladium catalysed cyanation reaction conditions may also be employed).

Other transformations that may be mentioned include: the conversion of a halo group (preferably iodo or bromo) to a 1-alkynyl group (e.g. by reaction with a 1-alkyne), which latter reaction may be performed in the presence of a suitable coupling catalyst (e.g. a palladium and/or a copper based catalyst) and a suitable base (e.g. a tri-($C_{1-S}$ alkyl)amine such as triethylamine, tributylamine or ethyldiisopropylamine); the introduction of amino groups and hydroxy groups in accordance with standard conditions using reagents known to those skilled in the art; the conversion of an amino group to a halo, azido or a cyano group, for example via diazotisation (e.g. generated in situ by reaction with $NaNO_2$ and a strong acid, such as HCl or $H_2SO_4$, at low temperature such as at 00° C. or below, e.g. at about –5° C.) followed by reaction with the appropriate nucleophile e.g. a source of the relevant anions, for example by reaction in the presence of a halogen gas (e.g. bromine, iodine or chlorine), or a reagent that is a source of azido or cyanide anions, such as $NaN_3$ or NaCN; the conversion of —C(O)OH to a —$NH_2$ group, under Schmidt reaction conditions, or variants thereof, for example in the presence of $HN_3$ (which may be formed in by contacting $NaN_3$ with a strong acid such as $H_2SO_4$), or, for variants, by reaction with diphenyl phosphoryl azide (($PhO)_2P(O)N_3$) in the presence of an alcohol, such as tert-butanol, which may result in the formation of a carbamate intermediate; the conversion of —$C(O)NH_2$ to —$NH_2$, for example under Hofmann rearrangement reaction conditions, for example in the presence of NaOBr (which may be formed by contacting NaOH and $Br_2$) which may result in the formation of a carbamate intermediate; the conversion of —$C(O)N_3$ (which compound itself may be prepared from the corresponding acyl hydrazide under standard diazotisation reaction conditions, e.g. in the presence of $NaNO_2$ and a strong acid such as $H_2SO_4$ or HCl) to —$NH_2$, for example under Curtius rearrangement reaction conditions, which may result in the formation of an intermediate isocyanate (or a carbamate if treated with an alcohol); the conversion of an alkyl carbamate to —$NH_2$, by hydrolysis, for example in the presence of water and base or under acidic conditions, or, when a benzyl carbamate intermediate is formed, under hydrogenation reaction conditions (e.g. catalytic hydrogenation reaction conditions in the presence of a precious metal catalyst such as Pd); halogenation of an aromatic ring, for example by an electrophilic aromatic substitution reaction in the presence of halogen atoms (e.g. chlorine, bromine, etc, or an equivalent source thereof) and, if necessary an appropriate catalyst/Lewis acid (e.g. $AlCl_3$ or $FeCl_3$).

Compounds of the invention bearing a carboxyester functional group may be converted into a variety of derivatives according to methods well known in the art to convert carboxyester groups into carboxamides, N-substituted carboxamides, N,N-disubstituted carboxamides, carboxylic acids, and the like. The operative conditions are those widely known in the art and may comprise, for instance in the conversion of a carboxyester group into a carboxamide group, the reaction with ammonia or ammonium hydroxide in the presence of a suitable solvent such as a lower alcohol, dimethylformamide or a mixture thereof; preferably the reaction is carried out with ammonium hydroxide in a methanol/dimethylformamide mixture, at a temperature ranging from about 50° C. to about 100° C. Analogous operative conditions apply in the preparation of N-substituted or N,N-disubstituted carboxamides wherein a suitable primary or secondary amine is used in place of ammonia or ammonium hydroxide. Likewise, carboxyester groups may be converted into carboxylic acid derivatives through basic or acidic hydrolysis conditions, widely known in the art. Further, amino derivatives of compounds of the invention may easily be converted into the corresponding carbamate, carboxamido or ureido derivatives.

Compounds of the invention may be isolated from their reaction mixtures using conventional techniques (e.g. recrystallisations).

It will be appreciated by those skilled in the art that, in the processes described above and hereinafter, the functional groups of intermediate compounds may need to be protected by protecting groups.

The need for such protection will vary depending on the nature of the remote functionality and the conditions of the preparation methods (and the need can be readily determined by one skilled in the art). Suitable amino-protecting groups include acetyl, trifluoroacetyl, t-butoxycarbonyl (BOC), benzyloxycarbonyl (CBz), 9-fluorenylmethyleneoxycarbonyl (Fmoc) and 2,4,4-trimethylpentan-2-yl (which may be deprotected by reaction in the presence of an acid, e.g. HCl in water/alcohol (e.g. MeOH)) or the like. The need for such protection is readily determined by one skilled in the art.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Synthesis*", 3rd edition, T. W. Greene & P. G. M. Wutz, Wiley-Interscience (1999).

Medical and Pharmaceutical Uses

Compounds of the invention are indicated as pharmaceuticals. According to a further aspect of the invention there is provided a compound of the invention, as hereinbefore defined, for use as a pharmaceutical.

Compounds of the invention may inhibit protein or lipid kinases, such as a PI3 kinase (especially a class I PI3K), for example as may be shown in the tests described below (for example, the test for PI3K (inhibition described below) and/or in tests known to the skilled person. The compounds of the invention may also inhibit mTOR. Thus, the compounds of the invention may be useful in the treatment of those disorders in an individual in which the inhibition of such protein or lipid kinases (e.g. PI3K, particularly class I PI3K, and/or mTOR) is desired and/or required (for instance compounds of the invention may inhibit PI3K, particularly class I PI3K and, optionally, may also inhibit mTOR).

The term "inhibit" may refer to any measurable reduction and/or prevention of catalytic kinase (e.g. PI3K, particularly class I PI3K, and/or mTOR) activity. The reduction and/or prevention of kinase activity may be measured by comparing the kinase activity in a sample containing a compound of the invention and an equivalent sample of kinase (e.g. PI3K, particularly class I PI3K, and/or mTOR) in the absence of a compound of the invention, as would be apparent to those skilled in the art. The measurable change may be objective (e.g. measurable by some test or marker, for example in an in vitro or in vivo assay or test, such as one described hereinafter, or otherwise another suitable assay or test known to those skilled in the art) or subjective (e.g. the subject gives an indication of or feels an effect).

Compounds of the invention may be found to exhibit 50% inhibition of a protein or lipid kinase (e.g. PI3K, such as class I PI3K, and/or mTOR) at a concentration of 100 μM or below (for example at a concentration of below 50 μM, or even below 10 μM, such as below 1 μM), when tested in an assay (or other test), for example as described hereinafter, or otherwise another suitable assay or test known to the skilled person.

Compounds of the invention are thus expected to be useful in the treatment of a disorder in which a protein or lipid kinase (e.g. PI3K, such as class I PI3K, and/or mTOR) is known to play a role and which are characterised by or associated with an overall elevated activity of that kinase (due to, for example, increased amount of the kinase or increased catalytic activity of the kinase). Hence, compounds of the invention are expected to be useful in the treatment of a disease/disorder arising from abnormal cell growth, function or behaviour associated with the protein or lipid kinase (e.g. PI3K, such as class I PI3K, and/or mTOR). Such conditions/disorders include cancer, immune disorders, cardiovascular diseases, viral infections, inflammation, metabolism/endocrine function disorders and neurological disorders.

The disorders/conditions that the compounds of the invention may be useful in treating hence includes cancer (such as lymphomas, solid tumours or a cancer as described hereinafter), obstructive airways diseases, allergic diseases, inflammatory diseases (such as asthma, allergy and Chrohn's disease), immunosuppression (such as transplantation rejection and autoimmune diseases), disorders commonly connected with organ transplantation, AIDS-related diseases and other associated diseases. Other associated diseases that may be mentioned (particularly due to the key role of kinases in the regulation of cellular proliferation) include other cell proliferative disorders and/or non-malignant diseases, such as benign prostate hyperplasia, familial adenomatosis, polyposis, neuro-fibromatosis, psoriasis, bone disorders, atherosclerosis, vascular smooth cell proliferation associated with atherosclerosis, pulmonary fibrosis, arthritis glomerulonephritis and post-surgical stenosis and restenosis. Other disease states that may be mentioned include cardiovascular disease, stroke, diabetes, hepatomegaly, Alzheimer's disease, cystic fibrosis, hormone-related diseases, immunodeficiency disorders, destructive bone disorders, infectious diseases, conditions associated with cell death, thrombin-induced platelet aggregation, chronic myelogenous leukaemia, liver disease, pathologic immune conditions involving T cell activation and CNS disorders.

As stated above, the compounds of the invention may be useful in the treatment of cancer. More, specifically, the compounds of the invention may therefore be useful in the treatment of a variety of cancer including, but not limited to: carcinoma such as cancer of the bladder, breast, colon, kidney, liver, lung (including non-small cell cancer and small cell lung cancer), esophagus, gall-bladder, ovary, pancreas, stomach, cervix, thyroid, prostate, skin, squamous cell carcinoma, testis, genitourinary tract, larynx, glioblastoma, neuroblastoma, keratoacanthoma, epidermoid carcinoma, large cell carcinoma, non-small cell lung carcinoma, small cell lung carcinoma, lung adenocarcinoma, bone, adenoma, adenocarcinoma, follicular carcinoma, undifferentiated carcinoma, papilliary carcinoma, seminona, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukaemia; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xeroderma pigmentosum, keratoxanthoma, thyroid follicular cancer and Kaposi's sarcoma.

Further, the protein or lipid kinases (e.g. PI3K, such as class I PI3K, and/or mTOR) may also be implicated in the multiplication of viruses and parasites. They may also play a major role in the pathogenesis and development of neurodegenerative disorders. Hence, compounds of the invention may also be useful in the treatment of viral conditions, parasitic conditions, as well as neurodegenerative disorders.

Compounds of the invention are indicated both in the therapeutic and/or prophylactic treatment of the above-mentioned conditions.

According to a further aspect of the present invention, there is provided a method of treatment of a disease (e.g. cancer or another disease as mentioned herein) which is associated with the inhibition of protein or lipid kinase (e.g. PI3K, such as class I PI3K, and/or mTOR), i.e. where such inhibition is desired and/or required (for example, a method of treatment of a disease/disorder arising from abnormal cell growth, function or behaviour associated with protein or lipid kinases, e.g. PI3K, such as class I PI3K, and/or mTOR), which method comprises administration of a therapeutically effective amount of a compound of the invention, as hereinbefore defined, to a patient suffering from, or susceptible to, such a condition.

"Patients" include mammalian (including human) patients. Hence, the method of treatment discussed above may include the treatment of a human or animal body.

The term "effective amount" refers to an amount of a compound, which confers a therapeutic effect on the treated patient. The effect may be objective (e.g. measurable by some test or marker) or subjective (e.g. the subject gives an indication of or feels an effect).

Compounds of the invention may be administered orally, intravenously, subcutaneously, buccally, rectally, dermally, nasally, tracheally, bronchially, sublingually, by any other parenteral route or via inhalation, in a pharmaceutically acceptable dosage form.

Compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like. The type of pharmaceutical formulation may be selected with due regard to the intended route of administration and standard pharmaceutical practice. Such pharmaceutically acceptable carriers may be chemically inert to the active compounds and may have no detrimental side effects or toxicity under the conditions of use.

Such formulations may be prepared in accordance with standard and/or accepted pharmaceutical practice. Otherwise, the preparation of suitable formulations may be achieved non-inventively by the skilled person using routine techniques and/or in accordance with standard and/or accepted pharmaceutical practice.

According to a further aspect of the invention there is thus provided a pharmaceutical formulation including a compound of the invention, as hereinbefore defined, in admixture with a pharmaceutically acceptable adjuvant, diluent and/or carrier.

Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The amount of compound of the invention in the formulation will depend on the severity of the condition, and on the patient, to be treated, as well as the compound(s) which is/are employed, but may be determined non-inventively by the skilled person.

The invention further provides a process for the preparation of a pharmaceutical formulation, as hereinbefore defined, which process comprises bringing into association a compound of the invention, as hereinbefore defined, or a pharmaceutically acceptable ester, amide, solvate or salt thereof with a pharmaceutically-acceptable adjuvant, diluent or carrier.

Compounds of the invention may also be combined with other therapeutic agents that are inhibitors of protein or lipid kinases (e.g. PI3K, such as class I PI3K, a PIM family kinase (e.g. PIM-1, PIM-2- and/or PIM-3) and/or mTOR) and/or useful in the treatment of a cancer and/or a proliferative disease. Compounds of the invention may also be combined with other therapies (e.g. radiation).

For instance, compounds of the invention may be combined with one or more treatments independently selected from surgery, one or more anti-cancer/anti-neoplastic/anti-tumoral agent, one or more hormone therapies, one or more antibodies, one or more immunotherapies, radioactive iodine therapy, and radiation.

More specifically, compounds of the invention may be combined with an agent that modulates the Ras/Raf/Mek pathway (e.g. an inhibitor of MEK), the Jak/Stat pathway (e.g. an inhibitor of Jak), the PI3K/Akt pathway (e.g. an inhibitor of Akt), the DNA damage response mechanism (e.g. an inhibitor of ATM or ATR) or the stress signaling pathway (an inhibitor of p38 or NF-KB).

For instance, compounds of the invention may be combined with:
(i) a targeted kinase inhibitor;
(ii) a receptor tyrosine kinase (RTK) inhibitor;
(iii) a PIM family kinase inhibitor, such as SGI-1776;
(iv) an Flt-3 inhibitor;
(v) an EGFR or HER2 inhibitor, such as lapatanib;
(vi) a therapeutic monoclonal antibody, such as the HER2 inhibitor trastuzumab;
(vii) a MEK inhibitor, such as PD-0325901;
(vii) a BRaf inhibitor, such as GDC-0879;
(viii) an anthracyclin, such as doxorubicin;
(ix) a taxane, such as paclitaxel or, particularly, docetaxel;
(x) a platin, such as carboplatin or, particularly, cisplatin;
(xi) a nucleotide analog, such as 5-fluorouracil (5-FU) or gemcitabine);
(xii) an alkylating agent, such as temozolomide;
(xiii) a hormone therapeutic agent, such as an estrogen receptor antagonist e.g. tamoxifen;
(xiv) an anti-tumour compound that has potential radiosensitising and/or chemosensitising effects, such as chloroquine;
(xv) an mTOR inhibitor, such as rapamycin;
(xvi) an Akt or PI3-K inhibitor, such as GDC-0941;
(xvii) a JAK inhibitor; and/or (xviii) an agent that modulates the DNA damage response mechanism and/or the stress signaling pathway, e.g. an inhibitor of ATM or ATR, an inhibitor of p38 and/or NF-KB.

According to a further aspect of the invention, there is provided a combination product comprising:
(A) a compound of the invention, as hereinbefore defined; and
(B) another therapeutic agent that is useful in the treatment of cancer and/or a proliferative disease,
wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined, another therapeutic agent that is useful in the treatment of cancer and/or a proliferative disease, and a pharmaceutically-acceptable adjuvant, diluent or carrier; and
(2) a kit of parts comprising components:
(a) a pharmaceutical formulation including a compound of the invention, as hereinbefore defined, in admixture with a pharmaceutically-acceptable adjuvant, diluent or carrier; and
(b) a pharmaceutical formulation including another therapeutic agent that is useful in the treatment of cancer and/or a proliferative disease in admixture with a pharmaceutically-acceptable adjuvant, diluent or carrier,
which components (a) and (b) are each provided in a form that is suitable for administration in conjunction with the other.

In a particularly preferred aspect of the invention, compounds of the invention may be combined with other therapeutic agents (e.g. chemotherapeutic agents) for use as medicaments (e.g. for use in the treatment of a disease or condition as mentioned herein, such as one in which the inhibition of growth of cancer cells are required and/or desired e.g. for treating hyperproliferative disorders such as cancer (e.g. specific cancers that may be mentioned herein, e.g. in the examples) in mammals, especially humans). Such active ingredients in combinations may act in synergy.

In particular, compounds of the invention may be combined with known chemotherapeutic agents (as may be demonstrated by the examples, for instance where a compound of the examples is employed in combination and inhibits cellular proliferation in vitro; in particular such combinations may be useful in treating lung and/or ovarian cancer), for instance:
(i) a MEK inhibitor, such as PD-0325901;
(ii) an EGFR inhibitor, such as Lapatinib; and/or
(iii) docetaxel (Taxotere®, Sanofi-Aventis).

The MEK inhibitor PD-0325901 (CAS RN 391210-10-9, Pfizer) is a second-generation, non-ATP competitive, allosteric MEK inhibitor for the potential oral tablet treatment of cancer (U.S. Pat. No. 6,960,614; U.S. Pat. No. 6,972,298; US 2004/1147478; US 2005/085550). Phase II clinical trials have been conducted for the potential treatment of breast tumors, colon tumors, and melanoma. PD-0325901 is named (R)—N-(2,3-dihydroxypropoxy)-3,4-difluoro-2-(2-fluoro-4-iodophenylamino)benz-amide, and has the structure:

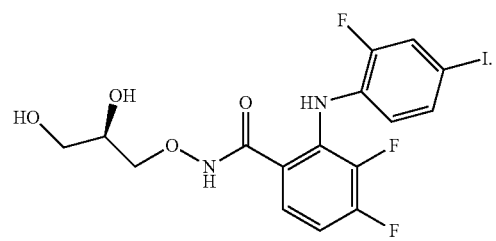 [SMILES: O=C(NOC[C@H](O)CO)c1ccc(F)c(F)c1Nc1ccc(I)cc1F]

Docetaxel (TAXOTERE®, Sanofi-Aventis) is used to treat breast, ovarian, and NSCLC cancers (U.S. Pat. No. 4,814,470; U.S. Pat. No. 5,438,072; U.S. Pat. No. 5,698,582; U.S. Pat. No. 5,714,512; U.S. Pat. No. 5,750,561; Mangatal et al (1989) Tetrahedron 45:4177; Ringel et al (1991) J. Natl. Cancer Inst. 83:288; Bissery et al (1991) Cancer Res. 51:4845; Herbst et al (2003) Cancer Treat. Rev. 29:407-415; Davies et al (2003) Expert. Opin. Pharmacother. 4:553-565). Docetaxel is named as (2R,3S)—N-carboxy-3-phenylisoserine, N-tert-butyl ester, 13-ester with 5,20-epoxy-1,2,4,7,10, 13-hexahydroxytax-11-en-9-one 4-acetate 2-benzoate, trihydrate (U.S. Pat. No. 4,814,470; EP 253738; CAS Reg. No. 114977-28-5) (or named as 1,7β,10β-trihydroxy-9-oxo-5β, 20-epoxytax-11-ene-2α,4,13α-triyl 4-acetate 2-benzoate 13-{(2R,3S)-3-[(tert-butoxycarbonyl)amino]-2-hydroxy-3-phenylpropanoate}) and has the structure:

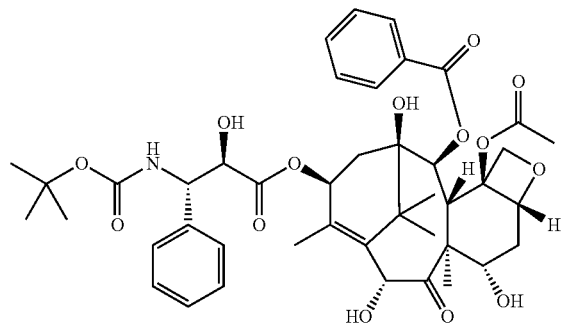 [SMILES: CC(=O)O[C@@]12CO[C@@H]1C[C@H](O)[C@@]1(C)C(=O)[C@H](O)C3=C(C)[C@@H](OC(=O)[C@H](O)[C@@H](NC(=O)OC(C)(C)C)c4ccccc4)C[C@](O)([C@@H](OC(=O)c4ccccc4)[C@H]21)C3(C)C]

Lapatinib (TYKERB®, GW572016, Glaxo SmithKline) has been approved for use in combination with capecitabine (XELODA®, Roche) for the treatment of patients with advanced or metastatic breast cancer whose tumors overexpress HER2 (ErbB2) and who have received prior therapy including an anthracycline, a taxane and trastuzumab. Lapatinib is an ATP-competitive epidermal growth factor (EGFR) and HER2/neu (ErbB-2) dual tyrosine kinase inhibitor (U.S. Pat. No. 6,727,256; U.S. Pat. No. 6,713,485; U.S. Pat. No. 7,109,333; U.S. Pat. No. 6,933,299; U.S. Pat. No. 7,084,147; U.S. Pat. No. 7,157,466; U.S. Pat. No. 7,141,576) which inhibits receptor autophosphorylation and activation by binding to the ATPbinding pocket of the EGFRIHER2 protein kinase domain. Lapatinib is named as N-(3-chloro-4-(3-fluorobenzyloxy)phenyl)-6-(5-((2-(methylsulfonyl)ethylamino)-methyl)furan-2-yl)quinazolin-4-amine (or alternatively named as N-[3-chloro-4-[(3-fluorophenyl)methoxy]phenyl]-6-[5-[(2-methylsulfonylethylamino)methyl]-2-furyl]quinazolin-4-amine), and has the structure:

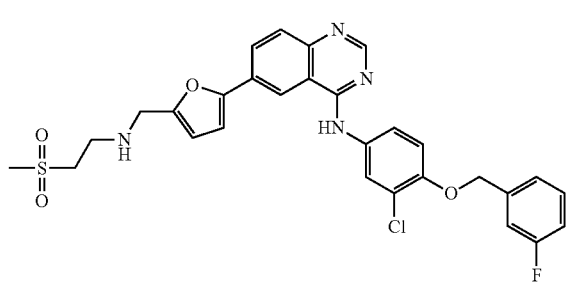 [SMILES: CS(=O)(=O)CCNCc1ccc(-c2ccc3ncnc(Nc4ccc(OCc5cccc(F)c5)c(Cl)c4)c3c2)o1]

The invention further provides a process for the preparation of a combination product as hereinbefore defined, which process comprises bringing into association a compound of the invention, as hereinbefore defined, or a pharmaceutically acceptable ester, amide, solvate or salt thereof with the other therapeutic agent that is useful in the treatment of cancer and/or a proliferative disease, and at least one pharmaceutically-acceptable adjuvant, diluent or carrier.

For instance, compounds of the invention may be combined with a chemotherapeutic agent. A "chemotherapeutic agent" is a biological (large molecule) or chemical (small molecule) compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, proteins, antibodies, photosensitizers, and kinase inhibitors. Chemotherapeutic agents include compounds used in "targeted therapy" and non-targeted, conventional chemotherapy.

Examples of chemotherapeutic agents include those mentioned in e.g. WO 2010/105008, for instance: dexamethasone, thioTEPA, doxorubicin, vincristine, rituximab, cyclophosphamide, prednisone, melphalan, lenalidomide, bortezomib, rapamycin, and cytarabine.

Examples of chemotherapeutic agents also include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanamine, NOLVADEX®, ISTUBAL®, VALODEX®), doxorubicin (ADRIAMYCIN®), Akti-1/2, HPPD, rapamycin, and lapatinib (TYKERB®, Glaxo SmithKline).

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (MEK inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), ABT-869 (multi-targeted inhibitor of VEGF and PDGF family receptor tyrosine kinases, Abbott Laboratories and Genentech), ABT-263 (Bcl-2/Bcl-xL inhibitor, Abbott Laboratories and Genentech), PTK787/ZK 222584 (Novartis), fulvestrant (FASLODEX®, AstraZeneca), leucovorin (folinic acid), lonafamib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), capecitabine (XELODA®, Roche), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thioTepa and cyclophosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma II, calicheamicin omega II, dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; antiadrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; tiaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thioTepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) antihormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTN®, Genentech); cetuximab (ERBITUX®, Imclone); panitumumab (VECTIBIX®, Amgen), rituximab (RITUXAN®, Genentech/Biogen Idec), pertuzumab (OMNITARG™, rhuMab 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanised monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, rolizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Depending on the disorder, and the patient, to be treated, as well as the route of administration, compounds of the invention may be administered at varying therapeutically effective doses to a patient in need thereof. However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of the invention.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

Compounds of the invention may have the advantage that they are effective inhibitors of protein or lipid kinases (e.g. PI3K, such as class I PI3K, and/or mTOR; hence, they may advantageously be dual inhibitors). Advantageously, compounds of the invention may inhibit (e.g. selectively) certain protein or lipid kinases (e.g. PI3K, such as class I PI3K), without exhibiting inhibition (or significant inhibition) of other protein or lipid kinases. For instance, the compounds of the invention may selectively inhibit only one protein or lipid kinase (e.g. PI3K, such as class I PI3K).

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise.

Examples/Biological Tests

Determination of the activity of PI3 kinase activity of compounds of the invention is possible by a number of direct and indirect detection methods. Certain exemplary compounds described herein were prepared, characterized, and tested for their PI3K binding activity and in vitro activity against tumor cells. The range of PI3K binding activities was less than 1 nM to about 10 μM (i.e. certain compounds of the examples/invention had PI3K binding activity $IC_{50}$ values of less than 10 nM). Compounds of the examples/invention had tumor cell-based activity $IC_{50}$ values less than 100 nM (see Tables below).

PI3K Activity Assay

The kinase activity was measured by using the commercial ADP Hunter™ Plus assay available from DiscoveR$_x$ (#33-016), which is a homogeneous assay to measure the accumulation of ADP, a universal product of kinase activity. The enzyme, PI3K (p110α/p85α was purchased from Carna Biosciences (#07CBS-0402A). The assay was done following the manufacturer recommendations with slight modifications: Mainly the kinase buffer was replace by 50 mM HEPES, pH 7.5, 3 mM $MgCl_2$, 100 mM NaCl, 1 mM EGTA, 0.04% CHAPS, 2 mM TCEP and 0.01 mg/ml BGG. The PI3K was assayed in a titration experiment to determine the optimal protein concentration for the inhibition assay. To calculate the $IC_{50}$ of the ETP-compounds, serial 1:5 dilutions of the compounds were added to the enzyme at a fixed concentration (2.5 μg/ml. The enzyme was preincubated with the inhibitor and 30 μM $PIP_2$ substrate (P9763, Sigma) for 5 min and then ATP was added to a final 50 μM concentration. Reaction was carried out for 1 hour at 25° C. Reagent A and B were sequentially added to the wells and plates were incubated for 30 min at 37° C. Fluorescence counts were read in a Victor instrument (Perkin Elmer) with the recommended settings (544 and 580 nm as excitation and emission wavelengths, respectively). Values were normalized against the control activity included for each enzyme (i.e., 100% PI3 kinase activity, without compound). These values were plot against the inhibitor concentration and were fit to a sigmoid dose-response curve by using the Graphad software.

Cellular Mode of Action

Cell Culture

The cell lines were obtained from the American Type Culture Collection (ATCC). U2OS (human osteosarcoma) was cultured in Dulbecco's modified Eagle's medium (DMEM). PC3 (human prostate carcinoma), MCF7 (human breast cardinoma), HCT116 (human colon carcinoma), 768-0 (human neuroblastoma), U251 (human glyoblastoma) were grown in RPMI. All media were supplemented with 10% fetal bovine serum (FBS) (Sigma) and antibiotics-antimycotics. Cell were maintained in a humidified incubator at 37° C. with 5% $CO_2$ and passaged when confluent using trypsin/EDTA.

U2foxRELOC and U2nesRELOC Assay

The U2nesRELOC assay and the U2foxRELOC assay have been described previously (1, 2). Briefly, cells were seeded at a density of $1.0 \times 10^5$ cells/ml into black-wall clear-bottom 96-well microplates (BD Biosciences) After incubation at 37° C. with 5% $CO_2$ for 12 hours, 2 μl of each test compound were transferred from the mother plates to the assay plates. Cells were incubated in the presence of the compounds for one hour. Then cells were fixed and the nucleus stained with DAPI (Invitrogen). Finally the plates were washed with 1×PBS twice and stored at 4° C. before analysis. Compounds of the invention have a range of in vitro cell potency activities from about 1 nM to about 10 μM.

Image Acquirement and Processing

Assay plates were read on the BD Pathway™ 855 Bioimager equipped with a 488/10 nm EGFP excitation filter, a 380/10 nm DAPI excitation filter, a 515LP nm EGFP emission filter and a 435LP nm DAPI emission filter. Images were acquired in the DAPI and GFP channels of each well using 10× dry objective. The plates were exposed 0.066 ms (Gain 31) to acquire DAPI images and 0.55 ms (Gain 30) for GFP images.

Data Analysis

The BD Pathway Bioimager outputs its data in standard text files. Data were imported into the data analysis software BD Image Data Explorer. The nuclear/cytoplasmic (Nuc/Cyt) ratios of fluorescence intensity were determined by dividing the fluorescence intensity of the nucleus by the cytoplasmic. A threshold ratio of greater than 1.8 was employed to define nuclear accumulation of fluorescent signal for each cell. Based on this procedure we calculated the percentage of cells per well displaying nuclear translocation or inhibition of nuclear export. Compounds that induced a nuclear accumulation of the fluorescent signal greater than 60% of that obtained from wells treated with 4 nM LMB were considered as hits. In order to estimate the quality of the HCS assay, the Z' factor was calculated by the equation: $Z'=1-[(3 \times \text{std. dev. of positive controls}) + (3 \times \text{std. dev. of negative controls})/(\text{mean of positive controls}) - (\text{mean of negative controls})]$.

PI3K Signalling

AKT Phosphorylation Inhibition Western Blot Analysis

Subconfluent cells were incubated under different conditions and washed twice with TBS prior to lysis. Lysis buffer was added containing 50 mM Tris HCl, 150 mM NaCl, 1% NP-40, 2 mM $Na_3VO_4$, 100 mM NaF, 20 mM $Na_4P_2O_7$ and protease inhibitor cocktail (Roche Molecular Biochemicals). The proteins were resolved on 10% SDS-PAGE and transferred to nitrocellulose membrane (Schleicher & Schuell, Dassel, Germany). The membranes were incubated overnight at 4° C. with antibodies specific for Akt, phospho-Ser-473-Akt (Cell Signaling Technology) and α-tubulin (Sigma), they were washed and then incubated with IRDye800 conjugated anti-mouse and Alexa Fluor 680 goat anti-rabbit IgG secondary antibodies. The bands were visualized using an Odyssey infrared imaging system (Li-Cor Biosciences). Compounds of the invention have a range of in vitro cell potency activities from about 1 nM to about 10 μM.

Cytotoxicity Assessment

The compounds were tested on 96-well trays. Cells growing in a flask were harvested just before they became confluent, counted using a haemocytometer and diluted down with media adjusting the concentration to the required number of cells per 0.2 ml (volume for each well). Cells were then seeded in 96-well trays at a density between 1000 and 4000 cells/well, depending of the cell size. Cells were left to plate down and grow for 24 hours before adding the drugs. Drugs were weighed out and diluted with DMSO to get them into solution to a concentration of 10 mM. From here a "mother plate" with serial dilutions was prepared at 200× the final concentration in the culture. The final concentration of DMSO in the tissue culture media should not exceed 0.5%. The appropriate volume of the compound solution (usually 2 microliters) was added automatically (Beckman FX 96 tip) to media to make it up to the final concentration for each drug. The medium was removed from the cells and replaced with 0.2 ml of medium dosed with drug. Each concentration was assayed in triplicate. Two sets of control wells were left on each plate, containing either medium without drug or medium with the same concentration of DMSO. A third control set was obtained with the cells untreated just before adding the drugs (seeding control, number of cells starting the culture). Cells were exposed to the drugs for 72 hours and then processed for MTT colorimetric read-out. Compounds of the invention have a range of in vitro cell potency activities from about 1 nM to about 10 μM.

mTOR Assay

Mammalian target of rapamycin (mTOR) was assayed by monitoring phosphorylation of GFP-4EBP using a homogeneous time-resolved fluorescence resonante energy transfer format and assay reagents from Invitrogen. In the presence of 10 M ATP, 50 mM Hepes (pH 7.5), 0.01% (v/v) Polysorbate 20, 10 mM $MnCl_2$, 1 mM EGTA, and 2.5 mM DTT, the mTOR-mediated phosphorylation of 200 nM GFP-4E-BP1 was measured under initial rate conditions. After incubation at room temperature for 60 min, the reaction was terminated by addition of 10 mM EDTA, and phosphorylated GFP-4E-BP1 was detected with 2 nM Tb-anti-p4E-BP1 antibody before reading on a Perkin-Elmer Wallac 1420 Fluorescence Reader (exc 340; em 490/520).

PI3K Cellular Activity (Elisa Assay)

Activity is measured as endogenous levels of phospho-Akt1 (Ser473) protein. Osteosarcoma U2OS cells are plated in 96 Poly-D-Lysine coating tissue culture plates (18.000 cells/well). After the treatment with serial dilutions of the compound during 3 h, the cells are fixed directly in the wells with 4% paraformaldehyde.

After fixing, individual wells go through the same series of steps used for a conventional immunoblot: including blocking with 5% BSA, incubation with 1/1000 of primary antibody-AKT (Ser 74) in PBS containing 5% BSA at 4° C. overnight (Cell Signalling), washing and incubation with second antibody HRP-anti-mouse IgG for 1 h at RT (Amersham). After the addition of SuperSignal ELISA Femto maximum sensitivity chemiluminescent substrate (Pierce) the results are read using a luminescence plate reader (Victor).

Cell Viability Assays and Combination Assays

Cells were seeded at 10000-50000 cells/well in 96 plates for 16 h. On day two, nine serial 1:3 compound dilutions were made in DMSO in a 96 well plate. The compounds were added to duplicate wells in 96-well cell plates a using a FX BECKMAN robot (Beckman Coulter) and incubated at 37° C. with $CO_2$ atmosphere. After 3 days, relative numbers of viable cells were measured by MTT (Sigma) according to manufacturer's instruction and read on EndVision (Perkin Elmer). $EC_{50}$ values were calculated using Activityl)ase from IDBS. Drugs in combination assays were dosed starting at $4 \times EC_{50}$ concentrations and continuing with serial dilutions 1:2. PI3K inhibitors and chemotherapeutic agents were added simultaneously.

An additional exemplary in vitro cell proliferation assay includes the following steps:
1. An aliquot of 200 µl of cell culture containing optimal density (between $10^4$-$5 \times 10^4$ cells) (see Examples for cell lines and tumour type) in medium was deposited in each well of a 96-well flat bottom plates.
2. Control wells were prepared containing medium without cells
3. The compound was added to the experimental wells and incubated for 3 days.
4. One quarter volume of MTT reagent with respect to the volume of cell culture medium present in each well was added and incubated 24 h at 37° C. with 5% $CO_2$.
5. One quarter volume of solubilisation buffer with respect to the volume of cell culture medium present in each well was added and incubated 24 h at 37° C. with 5% $CO_2$.
6. Formazan salt formed was recorded and reported in graphs as relative growth vs. cells treated only with dmso.

The individual measured $EC_{50}$ values against the particular cell of the exemplary compounds and of the chemotherapeutic agent are compared to the combination $EC_{50}$ value. The combination Index (CI) score is calculated by the Chou and Talalay method (CalcuSyn software, Biosoft). A CI less 0.8 indicates synergy. A CI between 0.8 and 1.2 indicates additivity. A CI greater than 1.2 indicates antagonism.

Where compound names are given herein, they are typically generated with ChemDraw.

The invention is illustrated by way of the following examples, in which the following abbreviations (or chemical symbols) may be employed: "dba" dibenzylidene acetone; "DCM" dichloromethane; "MeOH" methanol; "EtOH" ethanol; "THF" tetrahydrofuran; "DMF" dimethylformamide; "$CHCl_3$" chloroform; "DME" dimethoxyethane; "$Et_2O$" diethyl ether; "Hex" hexane; "EtOAc" ethyl acetate; "Pd $(PPh_3)_4$" tetrakis(triphenylphosphine)palladium; "KOAc" potassium acetate; "DIPEA" diisopropylethylamine; "Pd $(PPh_3)_4$" tetrakis(triphenylphosphine)-palladium; "Pd(dppf) $Cl_2$.DCM" 1,1'-bis(diphenylphosphino)ferrocenepalladium (II) dichloride, dichloromethane; "min." minutes; and "h." hours.

EXAMPLES AND EXPERIMENTAL

General Procedure

The HPLC measurement was performed using a HP 1100 from Agilent Technologies comprising a pump (binary) with degasser, an autosampler, a column oven, a diode-array detector (DAD) and a column as specified in the respective methods below. Flow from the column was split to a MS spectrometer. The MS detector was configured with an electrospray ionization source or API/APCI. Nitrogen was used as the nebulizer gas. The source temperature was maintained at 150° C. Data acquisition was performed with ChemStation LC/MSD quad, software.

Method 1

Reversed phase HPLC was carried out on a RP-C18 Gemini column (150×4.6 mm, 5 um); 10 min. linear gradient of 50-100% acetonitrile in water+100% acetonitrile in water 2 min): 210 nm and 254 or DAD.

Method 2

Reversed phase HPLC was carried out on a Gemini-NX C18 (100×2.0 mm; 5 µm), Solvent A: water with 0.1% formic acid; Solvent B: acetonitrile with 0.1% formic acid. Gradient: 5% of B to 100% of B within 8 min at 50° C., DAD.

Method 3

Reversed phase HPLC was carried out on a Gemini-NX C18 (100×2.0 mm; 5 um), Solvent A: water with 0.1% formic acid; Solvent B: acetonitrile with 0.1% formic acid. Gradient: 5% of B to 40% of B within 8 min at 50° C., DAD.

Method 4

Reversed phase HPLC was carried out on a Gemini-NX C18 (100×2.0 mm; 5 um), Solvent A: water with 0.1% formic acid; Solvent B: acetonitrile with 0.1% formic acid. Gradient: 0% of B to 30% of B within 8 min at 50° C., DAD.

Analytical Data and PI3Kα Activity

Rt means retention time (in minutes), $[M+H]^+$ means the protonated mass of the compound, method refers to the method used for (LC)MS.

Biological activity in PI3Kα (see biological test above) for certain examples is represented in Tables 3 & 4 by quantative results: IC50 (µM).

TABLE 1

Intermediates

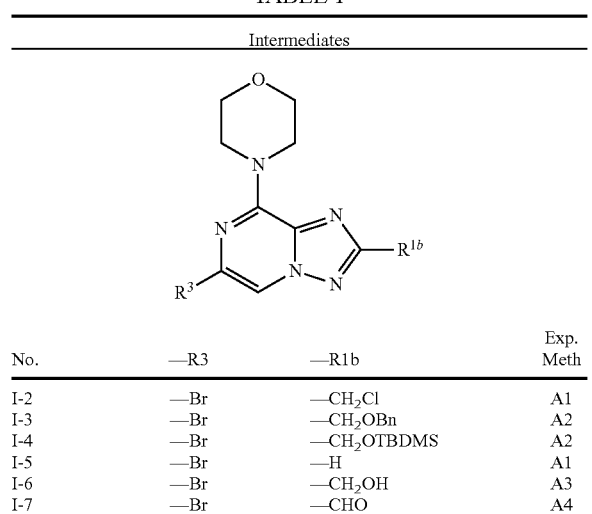

| No. | —R3 | —R1b | Exp. Meth |
|---|---|---|---|
| I-2 | —Br | —CH$_2$Cl | A1 |
| I-3 | —Br | —CH$_2$OBn | A2 |
| I-4 | —Br | —CH$_2$OTBDMS | A2 |
| I-5 | —Br | —H | A1 |
| I-6 | —Br | —CH$_2$OH | A3 |
| I-7 | —Br | —CHO | A4 |
| I-8 | —Br | (neopentyl-piperazinyl-SO$_2$Me) | A5 |
| I-9 | —Br | —Me | A1 |
| I-10 | —Br | (tetrahydropyranyl-C(Me)$_2$) | A1 |
| I-11 | —Br | (C(Me)$_2$CH(OH)Me) | A6 |
| I-12 | —Br | (neopentyl-piperidinyl) | A5 |

TABLE 1-continued

Intermediates

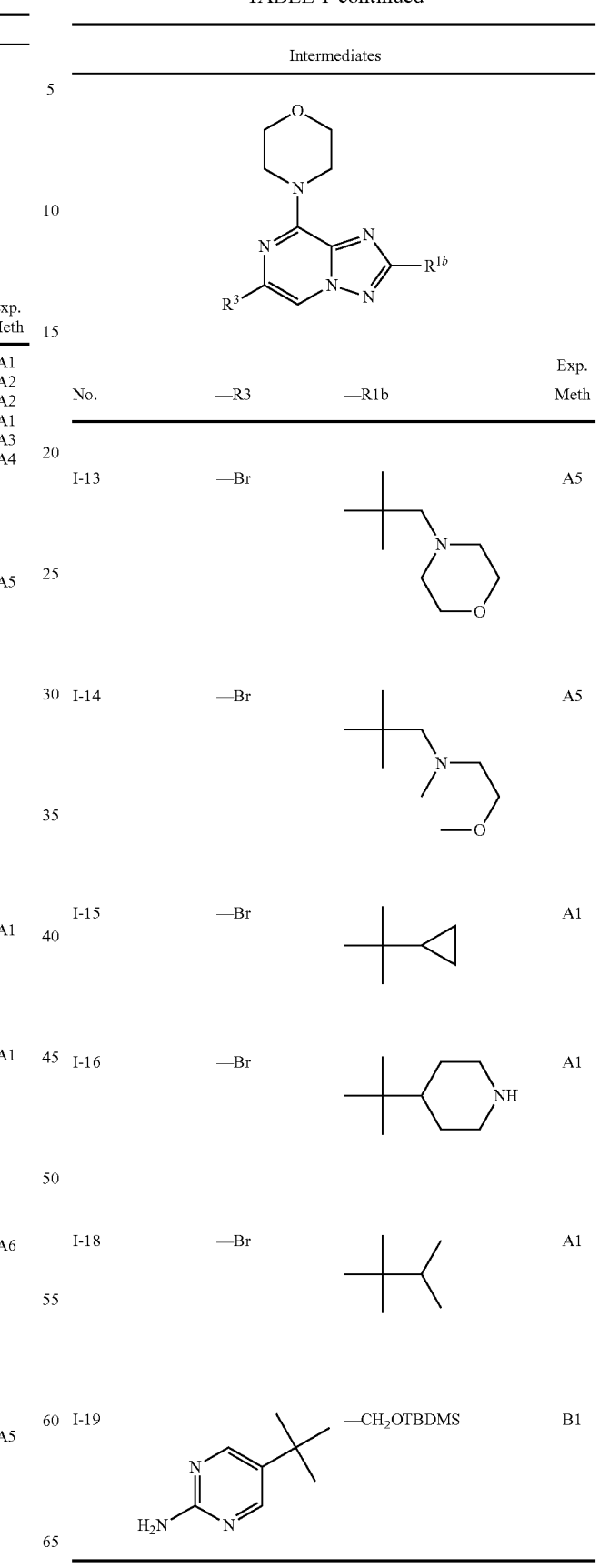

| No. | —R3 | —R1b | Exp. Meth |
|---|---|---|---|
| I-13 | —Br | (neopentyl-morpholinyl) | A5 |
| I-14 | —Br | (neopentyl-N(Me)CH$_2$CH$_2$OMe) | A5 |
| I-15 | —Br | (C(Me)$_2$-cyclopropyl) | A1 |
| I-16 | —Br | (C(Me)$_2$-piperidinyl-NH) | A1 |
| I-18 | —Br | (C(Me)$_2$CH(Me)$_2$) | A1 |
| I-19 | (2-aminopyrimidin-5-yl)-C(Me)$_2$ | —CH$_2$OTBDMS | B1 |

TABLE 2
Final Products
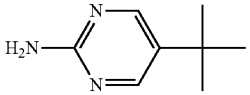
| Cpd. Nr. | —R3 | —R1b | R2 | Exp. | Method |
|---|---|---|---|---|---|
| 2-1 | 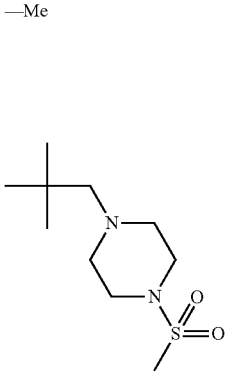 | —Me | —H | B1 | 2 |
| 2-2 |  | 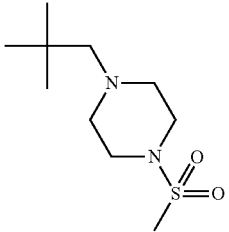 | —H | B1 | 2 |
| 2-3 | 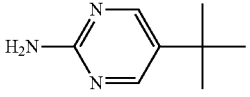 | 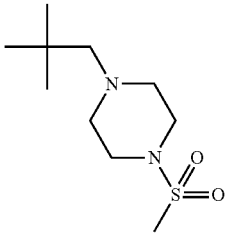 | —H | B1 | 2 |
| 2-4 | 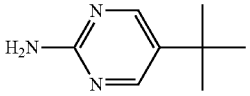 | 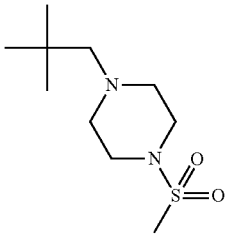 | —Cl | B2 | 2 |
| 2-5 | 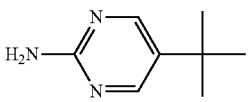 | 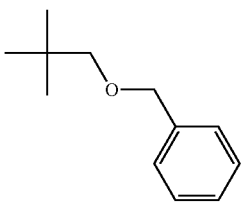 | —H | B1 | 2 |

TABLE 2-continued

Final Products

| Cpd. Nr. | —R3 | —R1b | R2 | Exp. | Method |
|---|---|---|---|---|---|
| 2-6 | 4-tert-butyl-1H-indazole | neopentyl benzyl ether | —H | B1 | 2 |
| 2-7 | 2-aminopyrimidin-5-yl | 3,3-dimethylbutan-2-yl | —H | B1 | 2 |
| 2-8 | 2-aminopyrimidin-5-yl | (piperidin-1-yl)methyl gem-dimethyl | —H | B1 | 2 |
| 2-9 | 2-aminopyrimidin-5-yl | (morpholin-4-yl)methyl gem-dimethyl | —H | B1 | 2 |
| 2-10 | 2-aminopyrimidin-5-yl | N-methyl-N-(2-methoxyethyl)aminomethyl gem-dimethyl | —H | B1 | 2 |
| 2-11 | 2-aminopyrimidin-5-yl | hydroxymethyl gem-dimethyl | —H | B2 | 2 |
| 2-12 | 2-aminopyrimidin-5-yl | cyclopropylmethyl gem-dimethyl | —H | B1 | 2 |

TABLE 2-continued

Final Products

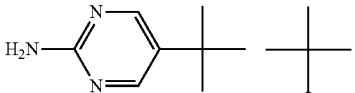

| Cpd. Nr. | —R3 | —R1b | R2 | Exp. | Method |
|---|---|---|---|---|---|
| 2-13 | 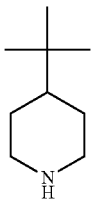 | 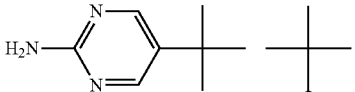 | —H | B1 | 2 |
| 2-14 | 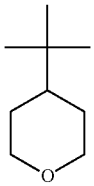 | 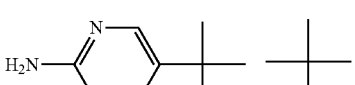 | —H | B1 | 2 |
| 2-15 | 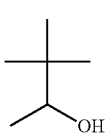 | | —H | B1 | 2 |

TABLE 3

Analytical Data and PI3Kα activity data (IC$_{50}$ values)

| Cpd. Nr. | Rt | [M + 1]+ | NMR | PI3Kα (μM) |
|---|---|---|---|---|
| 2-1 | 3.534 | 313.5 | $^1$H NMR (300 MHz, DMSO) δ 8.88 (s, 2H), 8.76 (s, 1H), 6.91 (s, 2H), 4.20 (s, 3H), 3.86-3.69 (m, 3H). | |
| 2-2 | 3.437 | 498.2 | $^1$H NMR (300 MHz, DMSO) δ 13.23 (s, 1H), 8.85 (s, 1H), 8.54 (s, 1H), 8.24 (s, 1H), 7.68 (d, J = 7.1 Hz, 1H), 7.61 (d, J = 8.3 Hz, 1H), 7.44 (dd, J = 8.3, 7.2 Hz, 1H), 4.25 (d, J = 4.5 Hz, 4H), 3.89-3.78 (m, 4H), 3.84 (s, 2H), 3.17-3.07 (m, 4H), 2.87 (s, 3H), 2.69-2.59 (m, 4H). | 0.128 |
| 2-3 | 2.192 | 475.6 | $^1$H NMR (300 MHz, DMSO) δ 8.88 (s, 2H), 8.80 (s, 1H), 6.92 (s, 2H), 4.20 (m, 4H), 3.8 (s, 2H) 3.79 (m, 4H), 3.11 (m, 4H), 2.83 (s, 3H), 2.62 (m, 4H). | 0.003 |
| 2-4 | 2.955 | 509.2 | $^1$H NMR (300 MHz, DMSO) δ = 8.68 (s, 2H), 7.05 (s, 2H), 4.16 (m, 4H), 3.86 (s, 2H), 3.81-3.72 (m, 4H), 3.11 (m, 4H), 2.87 (s, 3H), 2.63 (m, 4H). | 0.0014 |
| 2-5 | 3.437 | 498.2 | $^1$H NMR (300 MHz, DMSO) δ 8.82 (s, 2H), 8.78 (s, 1H), 7.28 (m, 5H), 6.87 (s, 2H), 4.66 (s, 2H), 4.55 (s, 2H), 4.15 (m, 4H), 3.85-3.59 (m, 4H). | 0.042 |
| 2-6 | 5.197 | 442.2 | $^1$H NMR (300 MHz, DMSO) δ 13.18 (s, 1H), 8.80 (s, 1H), 8.41 (s, 1H), 7.58 (dd, J = 25.6, 7.7 Hz, 2H), 7.50-7.15 (m, 6H), 4.71 (s, 2H), 4.58 (s, 2H), 4.29-4.10 (m, 4H), 3.90-3.61 (m, 4H). | |
| 2-7 | 4.519 | 341.2 | $^1$H NMR (300 MHz, DMSO) δ 8.87 (s, 2H), 8.78 (s, 1H), 6.90 (s, 2H), 4.24-4.14 (m, 4H), 3.82-3.73 (m, 4H), 1.34 (d, J = 6.9 Hz, 6H),. | 0.051 |

TABLE 3-continued

Analytical Data and PI3Kα activity data (IC$_{50}$ values)

| Cpd. Nr. | Rt | [M + 1]$^+$ | NMR | PI3Kα (µM) |
|---|---|---|---|---|
| 2-8 | 2.319 | 396.3 | $^1$H NMR (300 MHz, DMSO) δ 8.89 (s, 2H), 8.80 (s, 1H), 6.92 (s, 2H), 4.20 (m, 4H), 3.78 (m, 4H), 3.67 (s, 2H), 2.41 (m, 4H), 1.48 (m, 4H), 1.32 (m, 2H). | 0.195 |
| 2-9 | 2.559 | 398.5 | $^1$H NMR (300 MHz, DMSO) δ 8.88 (s, 2H), 8.80 (s, 1H), 6.92 (s, 2H), 4.20 (m, 4H), 3.85-3.76 (m, 4H), 3.73 (s, 2H), 3.63-3.52 (m, 4H), 2.55 (m, 4H). | |
| 2-10 | 2.796 | 400.3 | $^1$H NMR (300 MHz, DMSO) δ 9.05 (s, 2H), 8.97 (s, 1H), 7.08 (s, 2H), 4.38 (m, 4H), 4.00 (s, 2H), 4.00-3.89 (m, 4H), 3.62 (t, J = 6.0 Hz, 1H), 3.39 (s, 3H), 2.80 (t, J = 6.0 Hz, 1H), 2.43 (s, 3H). | |
| 2-11 | 2.918 | 329.2 | $^1$H NMR (300 MHz, DMSO) δ 8.82 (s, 2H), 8.73 (s, 1H), 6.85 (s, 2H), 5.46 (s, 1H), 4.58 (s, 2H), 4.14 (m, 4H), 3.84-3.52 (m, 4H). | 0.110 |
| 2-12 | 4.264 | 339.2 | $^1$H NMR (300 MHz, DMSO) δ 8.86 (s, 2H), 8.72 (s, 1H), 6.90 (s, 1H), 4.16 (s, 2H), 3.77 (d, 4H), 2.31-1.95 (m, 1H), 1.05 (dd, 2H), 0.96 (dd, 2H). | 0.054 |
| 2-13 | 0.381 | 382.2 | $^1$H NMR (300 MHz, DMSO) δ 8.80 (s, 2H), 8.73 (s, 1H), 8.32 (s, 1H), 6.84 (s, 1H), 4.14 (s, 1H), 3.72 (d, J = 4.7 Hz, 3H), 3.10 (d, J = 12.5 Hz, 2H), 2.75 (t, J = 10.8 Hz, 1H), 1.99 (d, J = 13.7 Hz, 2H), 1.85-1.64 (m, 2H), 1.17 (s, 1H). | |
| 2-14 | 3.932 | 383.3 | $^1$H NMR (300 MHz, DMSO) δ 8.86 (s, 2H), 8.78 (s, 1H), 6.89 (s, 2H), 4.19 (m, 4H), 3.92 (dd, J = 7.7, 2.8 Hz, 2H), 3.84-3.71 (m, 2H), 3.59-3.27 (m, 1H), 3.15 (m, 2H) 1.96 (m, 2H), 1.82 (m, 2H). | |
| 2-15 | 3.078 | 343.1 | $^1$H NMR (300 MHz, DMSO) δ 8.55 (s, 1H), 8.38 (s, 2H), 6.82 (s, 2H), 5.25 (m, 1H), 5.10 (m, 1H), 4.11 (m, 4H), 3.69 (m, 4H), 1.59 (d, 2H) | |

Synthesis of intermediates

Preparation of Intermediate I-1

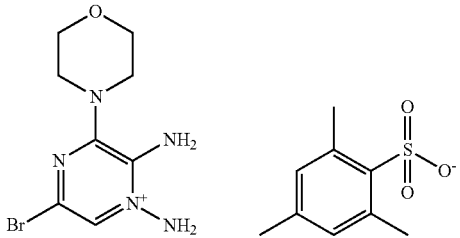

To a solution of 2-amino-5-bromo-3-morpholin-4-ylpyrazine (CAS:117719-17-2), (5 g, 19.297 mmol, 1 eq.) in DCM (250 mL), o-(mesitylsulfonyl)hydroxylamine, CAS: 36016-40-7, (4.154 g, 19.297 mmol, 1 eq.) was added. The mixture was stirred at rt for 18 h. The solid was filtered and dried, yielding: 8 g, of desired compound, intermediate I-1 (87%).

Method A1

Preparation of Intermediate I-2

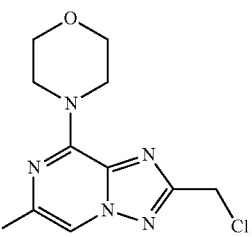

Method A:
To a solution of intermediate I-1 (200 mg, 0.422 mmol, 1 eq.) in 4 mL of dry DCM, DBU (0.189 mL, 1.265 mmol, 3 eq.) and chloroacetaldehyde (0.268 mL, 4.216 mmol, 10 eq.) were added and the mixture was stirred at rt in an open tube for 18 h. The solvent was evaporated to dryness. The residue was treated with MeOH, and the resulting solid was filtered off and dried. Yield: 760 mg of desired compound (54%), intermediate I-2.

Method B:
To a solution of 2,4,6-trimethyl-benzenesulfonic acid with 3,5-dibromo-2-imino-1(2H)-pyrazinamine (1:1), CAS: 785051-30-1, (0.200 g, 0.549 mmol, 1 eq.) in 2 mL of dry DCM, morpholine (0.144 mL, 1.648 mmol, 3 eq.) was added. The mixture was stirred at rt for 1 h and the solvent was evaporated to dryness. The residue was taken up into EtOH (2 mL) and chloroacetaldehyde (1 mL) and DBU (0.328 mL, 2.198 mmol, 4 eq.) were added and the mixture was stirred for 18 h at rt. The solvent was evaporated to dryness. The residue was purified by using a sep-pack in a manifold, hexane/EtOAc, 2/1. The desired fractions were collected and the solvent evaporated. Yield: 27 mg, 15% of intermediate I-2.

Preparation of Intermediate I-9

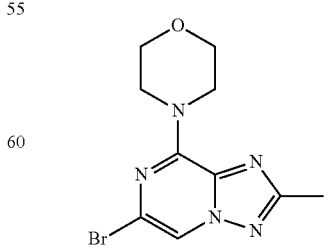

To a solution of 2,4,6-trimethyl-benzenesulfonic acid with 3,5-dibromo-2-imino-1(2H)-pyrazinamine (1:1), CAS:

785051-30-1, (100 mg, 0.275 mmol, 1 eq.) in 4 mL of dry DCM, morpholine (0.120 mL, 1.374 mmol, 5 eq.) was added. The mixture was stirred at RT for 1 h. Then, DBU (0.205 mL, 1.374 mmol, 5 eq.) and acetaldehyde (0.308 mL, 5.494 mmol, 20 eq.) were added and the mixture was stirred at rt in an open tube for 18 h. The solvent was evaporated to dryness. The residue was purified by using a sep-pack in a manifold, hexane/EtOAc, 5/1. The desired fractions were collected and the solvent evaporated. Yield: 17 mg, 20% of intermediate I-9.

Preparation of Intermediate I-10

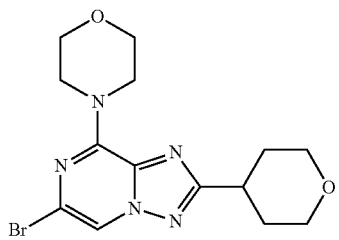 [SMILES: Brc1cn2nc(C3CCOCC3)nc2c(N2CCOCC2)n1]

Two batches were progressed:

To a solution of 2,4,6-trimethyl-benzenesulfonic acid with 3,5-dibromo-2-imino-1(2H)-pyrazinamine (1:1), CAS: 785051-30-1 (100 mg,) in 2 mL of dry DCM, morpholine (0.120 mL) was added. The mixture was stirred at rt for 1 h. Then, tetrahydropyranecarboxaldehyde (0.627 mg, 20 eq.) and DBU (0.205 mL, 5 eq.) were added and the mixture was stirred at rt in an open tube for 18 h. The solvent was evaporated to dryness. The residue from the two batches was purified in cyclohexane/EtOAc 5:1 to obtain the expected product as intermediate I-10.

Preparation of Intermediate I-5

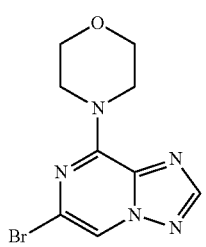 [SMILES: Brc1cn2ncnc2c(N2CCOCC2)n1]

Five separate reactions were performed as follow:

To a solution of 2,4,6-trimethyl-benzenesulfonic acid with 3,5-dibromo-2-imino-1(2H)-pyrazinamine (1:1), CAS: 785051-30-1 (200 mg, 0.549 mmol, 1 eq.) in 4 mL of dry DCM, morpholine (0.240 mL, 2.747 mmol, 5 eq.) was added. The mixture was stirred at RT for 1 h. Then, DBU (0.246 mL, 1.648 mmol, 3 eq.) and paraformaldehyde (330 mg, 2.74 mmol, 5 eq.) were added and the mixture was stirred in an open tube for 18 h at rt. After evaporation the five reactions were purified together by using a sep-pack in a manifold, eluent: cyclohexane/AcOEt, 5/1; the desired fractions were collected and the solvent was evaporated. Yield: 57 mg, 7%.

Method A2

Preparation of Intermediate I-4

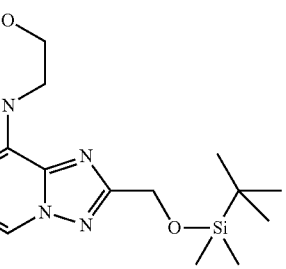

To a solution of morpholine (2.4 mL, 27.47 mmol, 10 eq.) in 75 mL of dry DCM, at 0° C., under $N_2$, NaH (604 mg, 15.1 mmol, 5.5 eq.) was added. The mixture was stirred at rt for 10 min., then 2,4,6-trimethyl-benzenesulfonic acid with 3,5-dibromo-2-imino-1(2H)-pyrazinamine (1:1), CAS: 785051-30-1, (1 g, 2.74 mmol, 1 eq.) was added portionwise. The mixture was stirred for 2 h at rt. Then, tert-butyldimethylsilyloxyacetaldehyde (0.628 mL, 3.29 mmol, 1.2 eq.) was added and the reaction was stirred at rt for 20 h. Water was added. The organic phase was separated, dried ($Na_2SO_4$), filtered and evaporated. The residue was purified in the biotage: Hexane/AcOEt. The desired fractions were collected and evaporated. Yield: 80 mg of intermediate I-4, 7% and 150 mg of intermediate 5-(8-Morpholin-4-yl-[1,2,4]triazolo[1,5-a]pyrazin-6-yl)-pyrimidin-2-ylamine, Y: 19%.

Method A3

Preparation of Intermediate I-6

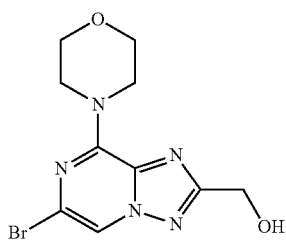 [SMILES: OCc1nc2c(N3CCOCC3)nc(Br)cn2n1]

A solution of intermediate I-4 (80 mg, 0.187 mmol, 1 eq.) in tetrabutylammonium fluoride (2.8 mL, 2.8 mmol, 15 eq.) was stirred at rt for 1 h. The solvent was evaporated to dryness, the residue was used in the next reaction step without further purification as intermediate I-6.

Method A4

Preparation of Intermediate I-7

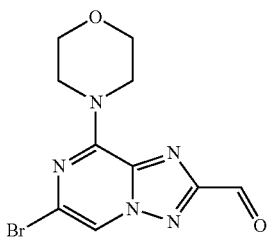 [SMILES: O=Cc1nc2c(N3CCOCC3)nc(Br)cn2n1]

Method A:
A mixture of intermediate I-6 (0.187 mmol, 1 eq.) and manganese dioxide (276 mg, 3.179 mmol, 17 eq.) in chloroform (4 mL) was stirred at reflux for 20 h. After filtration through dicalite, the solvent was evaporated to dryness. The residue was used in the next reaction step without further purification as intermediate I-7.

Method B:
To a solution of intermediate I-5 (90 mg, 0.317 mmol, 1 eq.) in THF (2 mL) at −78° C., LDA (0.352 mL, 1.8 M in hexanes, 0.634 mmol, 2 eq.) was added. After 1 h, DMF (1 mL) was added, and the mixture was stirred at −78° C. for 1 h, a saturated solution of ClNH$_4$ was added at −78° C., and AcOEt was added. After the mixture was allowed to warm to rt the organic phase was separated, dried (Na$_2$SO$_4$), filtered and evaporated to dryness, the residue was used in the next step without further purification as intermediate I-7.

Method A5

Preparation of Intermediate I-8

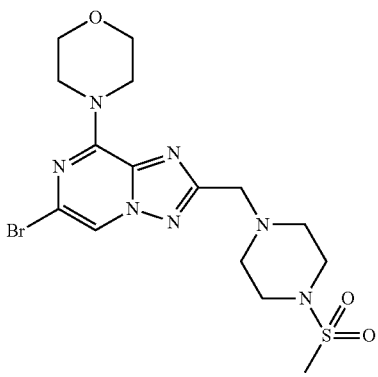 [SMILES: CS(=O)(=O)N1CCN(Cc2nc3c(N4CCOCC4)nc(Br)cn3n2)CC1]

A mixture of intermediate I-7 (0.187 mmol, 1 eq.), 1-(methylsulfonyl)piperazine (40 mg, 0.243 mmol, 1.3 eq.) and trimethyl orthoformate (0.205 mL, 1.87 mmol, 10 eq.) in DCE (4 mL) was stirred at rt for 4 h. Sodium triacetoxyborohydride (48 mg, 0.224 mmol, 1.2 eq.) was added to the reaction mixture and it was stirred at rt for 16 h. Water was added and the reaction was extracted with DCM. The combined organic layers were dried over Na$_2$SO$_4$, filtered and concentrated under reduced pressure. The residue was purified by using a sep-pack in a manifold: DCM/MeOH, 96/4. The desired fractions were collected, yielding: 48 mg of intermediate I-8

Method A6

Intermediate I-11

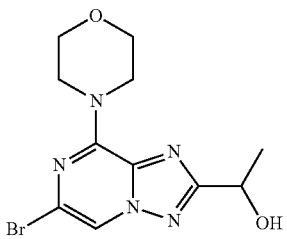 [SMILES: CC(O)c1nc2c(N3CCOCC3)nc(Br)cn2n1]

To a solution of intermediate I-7 (0.317 mmol, 1 eq.) in THF (4 mL) at 0° C., methylmagnesium chloride (3M in THF) (1.05 mL, 3.17 mmol, 10 eq.) was added. The mixture was stirred at rt for 1 h. NH$_4$Cl (aq. sat.) was added and the mixture was extracted with AcOEt. The organic phase was separated, dried (Na$_2$SO$_4$), filtered and evaporated to dryness. The residue was used in the next step without further purification.

Synthesis of Final Products

Example B1

Preparation of Final Product 2-2

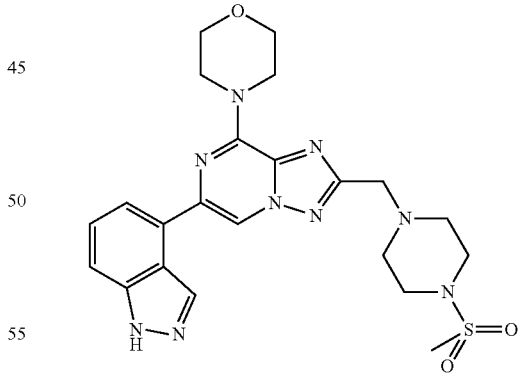

To a mixture of intermediate I-8 (48 mg, 0.104 mmol, 1 eq.), indazole-4-boronic acid hydrochloride (27 mg, 0.136 mmol, 1.3 eq.), and PdCl$_2$ (dppf) (9 mg, 0.010 mmol, 0.1 eq.), in DME (1 ml), a saturated solution of potassium carbonate (0.1 ml) was added. The mixture was heated at 130° C. under microwave irradiation for 30 min. The reaction mixture was diluted with DCM and water was added. After filtration through dicalite, the organic phase was separated, dried (Na$_2$SO$_4$) and evaporated to dryness. The residue was purified by using a sep-pack in a manifold: DCM:MeOH, 92:8. The desired fractions were collected and the solvent was evaporated to dryness. The residue was purified by HPLC. Yielding: 13 mg, 25%.

Preparation of Final Product 2-3

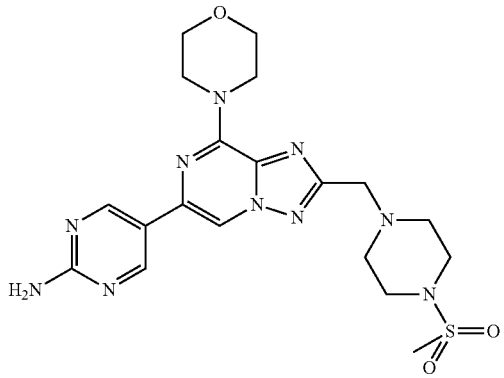

To a mixture of intermediate I-8 (45 mg, 0.098 mmol, 1 eq.), 2-aminopyrimidine-5-boronic acid pinacol ester (28 mg, 0.127 mmol, 1.3 eq.), and PdCl$_2$ (dppf) (8 mg, 0.01 mmol, 0.1 eq.), in DME (2 ml), a saturated solution of potassium carbonate (0.2 ml) was added. The mixture was heated at 130° C. under microwave irradiation for 1 h. The reaction mixture was diluted with DCM and water was added. After filtration through dicalite, the organic phase was separated, dried (Na$_2$SO$_4$) and evaporated to dryness. The residue was purified by CCTLC in a chromatotron: DCM:MeOH, 92:8. The desired fractions were collected and the solvent was evaporated to dryness. The residue was treated with CH$_3$CN/Et$_2$O, filtered and dried. Yield: 10 mg, 21% of compound 2-3.

Preparation of final product 2-1

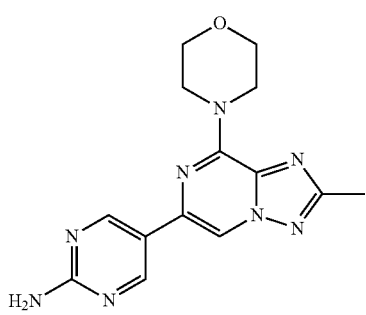 [SMILES: Cc1nc2c(N3CCOCC3)nc(-c3cnc(N)nc3)cn2n1]

To a mixture of intermediate I-9 (17 mg, 0.057 mmol, 1 eq.), 2-aminopyrimidine-5-boronic acid pinacol ester (16 mg, 0.074 mmol, 1.3 eq.), and PdCl$_2$ (dppf) (5 mg, 0.006 mmol, 0.1 eq.), in DME (1 ml), a saturated solution of potassium carbonate (0.1 ml) was added. The mixture was heated at 130° C. under microwave irradiation for 1 h. The reaction mixture was diluted with DCM and water was added. After filtration through dicalite, the organic phase was separated, dried (Na$_2$SO$_4$) and evaporated to dryness. The residue was purified by CCTLC in a chromatotron, eluent: DCM/MeOH, 92/8. The desired fractions were collected and the solvent was evaporated. Yield: 17 mg, 40% of compound 2-1.

Preparation of Final Product 2-14

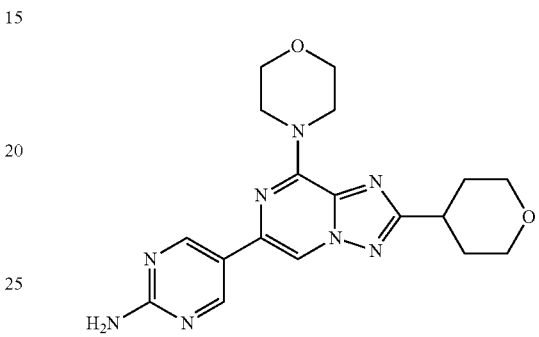

To a reaction mixture of intermediate I-10 (100 mg), 2-aminopyrimidine boronate (72 mg), and PdCl$_2$ (dppf), (22 mg) in DME (2 ml), was added a saturated solution of potassium carbonate (1 ml). The mixture was heated at 130° C. under microwave irradiation for 30 min. The mixture was filtered through celite, the filtrate was extracted with water. The organic phase was dried (Na$_2$SO$_4$), filtered and evaporated. The residue was precipitated with MeOH and washed with Et$_2$O to obtain impure final compound, which was purified by sep pack chromatography in DCM/MeOH 100 to 98:2 to obtain 5 mg of a white solid after liophilization as final product 2-14.

Example B2

Preparation of Final Product 2-4

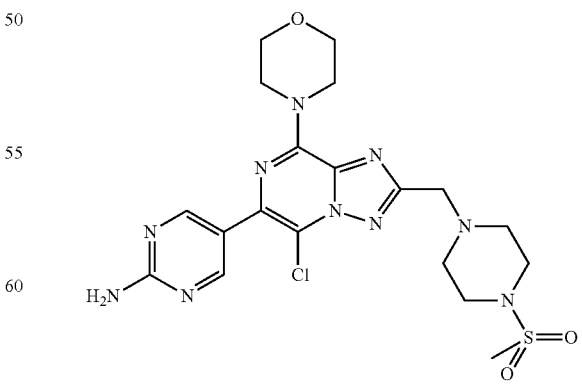

Final compound 2-3 (0.434 mmol, 1 eq) was suspended in DCM (4.3 mL) and NCS (58 mg, 0.434 mmol, 1 eq) was added. The reaction mixture was stirred at rt for 20 h. The suspension was concentrated and the residue was purified by biotage (eluent cyclohexane/EtOAc: 100/0 to 60:40) to obtain final product 2-17 as a white solid, 120 mg, 55%.

Example B3

Preparation of Final Product 2-11

A solution of intermediate I-19 (25 mg, 0.056 mmol, 1 eq.) in tetrabutylammonium fluoride (0.847 mL, 0.847 mmol, 15 eq.) was stirred at rt for 1 h. The solvent was evaporated to dryness, the residue was treated with MeOH, the solid was filtered, then purified by HPLC. Yielding: 3 mg, Y: 16% as final compound 2-11.

Preparation of Intermediate I-19

The following intermediate was prepared in accordance with the procedures described herein (e.g. from intermediate I-4 and 2-aminopurimide-5-boronate (or the corresponding boronic acid pinacol ester)).

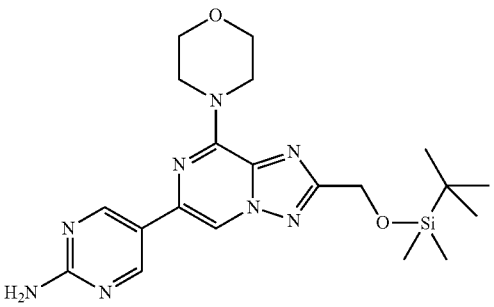 [SMILES: CC(C)(C)[Si](C)(C)OCc1nc2c(N3CCOCC3)nc(-c3cnc(N)nc3)cn2n1]

Any remaining compounds of Table 2 were prepared in accordance with the procedures described herein.

TABLE 4

| Cpd Nr. | Compound | Rt | [M + 1]⁺ | Meth | NMR | PI3Kα (µM) |
|---|---|---|---|---|---|---|
| 3-1 | | 4.513 | 341.2 | 2 | ¹H NMR (300 MHz, DMSO) δ 8.75 (s, 1H), 7.66 (s, 1H), 7.62 (m, 1H), 7.35 (t, J = 7.9 Hz, 1H), 6.94 (s, 1H), 6.92 (m, 1H), 5.34 (t, J = 5.7 Hz, 1H), 4.65 (d, J = 5.7 Hz, 1H), 4.13-3.63 (m, 8H), 3.83 (s, 3H) | |
| 3-2 | | 3.822 | 327.2 | 2 | ¹H NMR (300 MHz, DMSO) δ 9.46 (s, 1H), 8.59 (s, 1H), 7.47 (m, 1H), 7.45 (m, 1H), 7.22 (t, J = 7.9 Hz, 1H), 6.93 (s, 1H), 6.78-6.71 (m, 1H), 5.33 (t, J = 5.7 Hz, 1H), 4.64 (d, J = 5.7 Hz, 2H), 3.80 (m, 8H). | 0.174 |
| 3-3 | | 4.765 | 326.2 | 2 | ¹H NMR (300 MHz, DMSO) δ 8.30 (s, 1H), 7.673 (m, 1H), 7.62 (m, 1H), 7.38 (t, J = 8.0 Hz, 1H), 6.96 (dd, J = 7.8, 2.3 Hz, 1H), 4.30 (m, 4H), 3.8 (s, 3H), 3.69 (m, 4H), 2.72 (s, 3H). | |

TABLE 4-continued

Further Examples & Analytical Data and PI3Kα activity (IC$_{50}$)

| Cpd Nr. | Compound | Rt | [M + 1]$^+$ | Meth | NMR | PI3Kα (μM) |
|---|---|---|---|---|---|---|
| 3-4 | | 3.851 | 335.4 | 2 | $^1$H NMR (300 MHz, DMSO) δ 13.22 (s, 1H), 8.55 (s, 1H), 8.21 (s, 1H), 7.68 (m, 1H), 7.59 (m, 1H), 7.51-7.37 (m, 1H), 4.34 (m, 4H), 3.98-3.63 (m, 4H), 2.76 (s, 3H). | |
| 3-5 | | 2.849 | 313.5 | 2 | $^1$H NMR (300 MHz, DMSO) δ = 8.82 (s, 2H), 8.16 (s, 1H), 6.83 (s, 1H), 4.23 (m, 4H), 3.84-3.55 (m, 4H), 2.62 (s, 3H). | 0.165 |
| 3-6 | | 3.876 | 312.5 | 2 | $^1$H NMR (300 MHz, DMSO) δ = 9.56 (s, 1H), 8.27 (s, 1H), 7.73-7.43 (m, 2H), 7.31 (t, J = 8.1, 1H), 7.02-6.72 (m, 1H), 4.37 (m, 4H), 3.99-3.69 (m, 4H), 2.78 (s, 3H). | 0.952 |
| 3-7 | | 4.522 | 298.1 | 2 | $^1$H NMR (300 MHz, DMSO) δ = 9.56 (s, 1H), 8.64 (s, 1H), 7.95 (s, 1H), 7.72-7.65 (m, 2H), 7.28 (t, J = 8.1, 1H), 6.92-6.85 (m, 1H), 4.07 (m, 4H), 3.84-3.76 (m, 4H), 3.16 (s, 2H). | |

TABLE 4-continued
Further Examples & Analytical Data and PI3Kα activity (IC$_{50}$)
| Cpd Nr. | Compound | Rt | [M + 1]⁺ | Meth | NMR | PI3Kα (μM) |
|---|---|---|---|---|---|---|
| 3-8 | 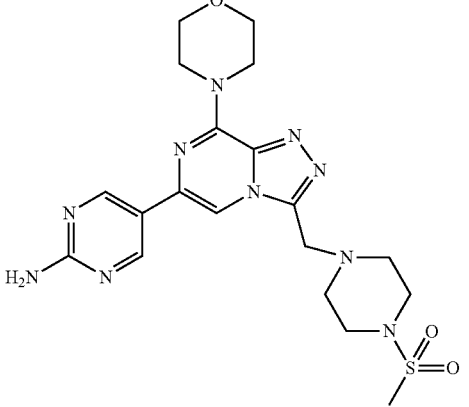 | 3.104 | 475.7 | 2 | ¹H NMR (300 MHz, DMSO) δ = 8.87 (s, 2H), 8.28 (s, 1H), 6.93 (s, 2H), 4.31 (m, 4H), 4.10 (s, 2H), 3.89-3.67 (m, 4H), 3.08 (m, 4H), 2.84 (s, 3H), 2.61 (s, 4H). | |
| 3-9 | 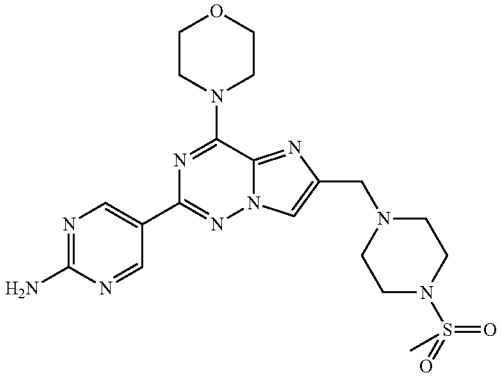 | | | | ¹H NMR (300 MHz, DMSO) δ = 8.97 (s, 2H), 7.98 (s, 1H), 7.14 (s, 2H), 4.78 (m, 2H), 4.10 (m, 2H), 3.94-3.72 (m, 4H), 3.65 (s, 2H), 3.12 (m, 4H), 2.87 (s, 3H), 2.55 (m, 4H). | 0.003 |
| 3-10 | 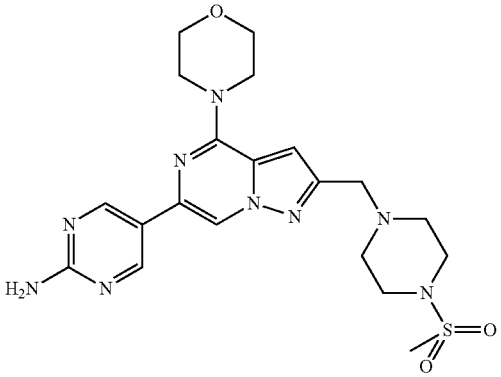 [SMILES: CS(=O)(=O)N1CCN(Cc2cc3c(N4CCOCC4)nc(-c4cnc(N)nc4)cn3n2)CC1] | 2.990 | 474.5 | 2 | ¹H NMR (300 MHz, DMSO) δ 8.86 (s, 2H), 8.66 (s, 1H), 6.92 (s, 1H), 6.83 (s, 2H), 3.77 (s, 8H), 3.72 (s, 2H), 3.11 (m, 4H), 2.86 (s, 3H), 2.53 (m, 4H). | 0.002 |
| 3-11 | 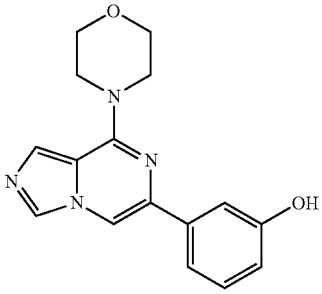 [SMILES: Oc1cccc(-c2cn3cncc3c(N3CCOCC3)n2)c1] | 3.201 | 297.1 | 2 | ¹H NMR (300 MHz, DMSO) d 9.45 (s, 1H), 8.43 (s, 1H), 8.35 (s, 1H), 7.85 (s, 1H), 7.40 (t, J = 2.0 Hz, 1H), 7.36 (d, J = 7.9 Hz, 1H), 7.22 (t, J = 7.9 Hz, 1H), 6.75 (dd, J = 7.9, 0.8 Hz, 1H), 3.84 (d, J = 5.1 Hz, 4H), 3.79 (d, J = 4.9 Hz, 4H). ¹³C NMR (75 MHz, DMSO) d 157.54, 150.27, 138.19, 135.24, 131.37, 129.42, 124.03, 117.66, 115.88, 114.97, 112.48, 104.50, 65.74, 46.29. | 0.317 |

TABLE 4-continued

Further Examples & Analytical Data and PI3Kα activity (IC$_{50}$)

| Cpd Nr. | Compound | Rt | [M + 1]$^+$ | Meth | NMR | PI3Kα (μM) |
|---|---|---|---|---|---|---|
| 3-12 | | 4.217 | 311.2 | 2 | 1H NMR (300 MHz, DMSO) d 8.46 (d, J = 0.6, 1H), 8.42 (s, 1H), 7.86 (s, 1H), 7.54 (m, J = 8.5, 1.8, 2H), 7.36 (t, J = 7.9, 1H), 6.93 (ddd, J = 8.2, 2.5, 0.9, 1H), 3.85 (m, 4H), 3.82 (s, 3H), 3.78 (m, 4H). | 2 |

Preparation of Final Product 3-2

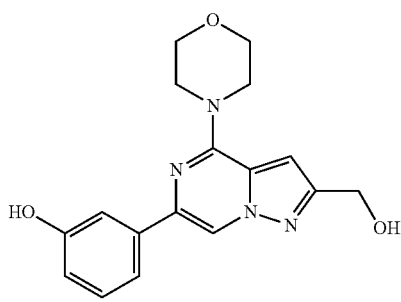 [SMILES: OCc1cc2c(N3CCOCC3)nc(-c3cccc(O)c3)cn2n1]

Boron fluoride-dimethyl sulfide complex (0.216 mL, 2.057 mmol) was added to a stirred solution of final product 3-1 (70 mg, 0.206 mmol) in DCM (1.2 mL) at rt. The mixture was stirred at rt for 24 h. NaHCO$_3$ sat. was added and the mixture was extracted with DCM/MeOH 90:1. The organic phase was separated, dried (Na$_2$SO$_4$), filtered and evaporated to dryness. The residue was purified by biotage (eluent: DCM/MeOH 100/0 to 60/40) to obtain final product 3-2 as a white solid (45 mg, 67% yield).

Preparation of Final Product 3-1

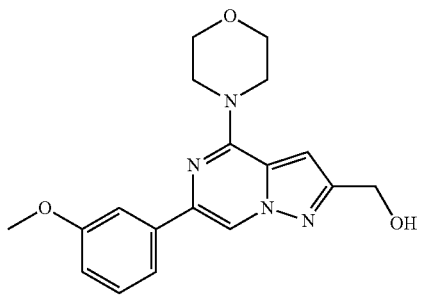 [SMILES: COc1cccc(-c2cn3nc(CO)cc3c(N3CCOCC3)n2)c1]

To a stirred slurry of LiAlH$_4$ (52 mg, 1.360 mmol) in dry THF (1 mL) was slowly added intermediate II-24 (5.63 mmol) in THF (1.6 mL) at 0° C. After the addition, the reaction mixture was stirred at room temperature for 2 h. The reaction mixture was quenched with saturated NH$_4$Cl/NH$_4$OH and DCM was added. The organic layer was washed with saturated NaCl and dried over anhydrous Na$_2$SO$_4$. The filtrate was concentrated under reduced pressure. The crude was purified by biotage (eluent: cyclohexane/EtOAc 100/0 to 0/100) to obtain 140 mg of a white solid as final product 3-1.

Preparation of Intermediate II-24

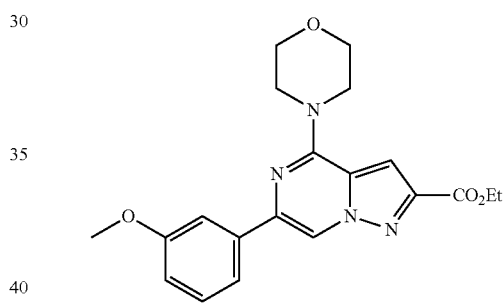

Intermediate II-9 (0.7 g, 2.110 mmol, 1 eq) was dissolved in DCM (7 mL) and morpholine (0.185 mL, 2.110 mmol) was carefully added, after which a solid crashing out was observed. The reaction mixture was stirred at RT for 36 h. Then, the solvent was evaporated, and the residue was purified by biotage (eluent: cyclohexane/EtOAc: 100/0 to 60/40 to obtain 680 mg (84% yield) of intermediate II-24 as a white solid.

Preparation of Intermediate II-9

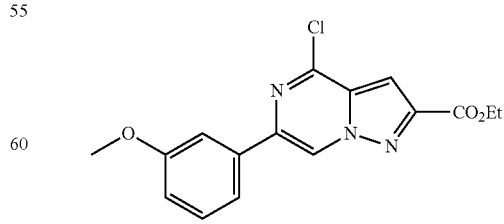

A solution of intermediate II-8 (0.100 g, 0.319 mmol) in phosphorus oxychloride (2 mL) was heated at reflux for 2 h. The reaction mixture was poured over a saturated solution of sodium bicarbonate (20 mL) and the mixture was neutralised with potassium carbonate. The precipitate (white solid) was filtered, washed with water and dried under vacuum to obtain the expected compound as intermediate II-9 which was used in next reaction step without further purification.

Preparation of Intermediate II-8

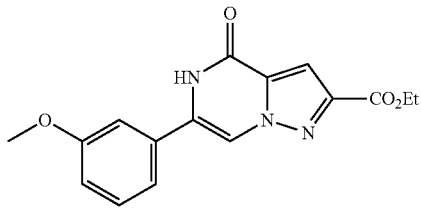 [SMILES: CCOC(=O)c1cc2c(=O)[nH]c(-c3cccc(OC)c3)cn2n1]

The reaction was performed in two batches to obtain intermediate II-8 (approx 0.8 g each).

To a solution of intermediate II-7 (0.840 g, 2.914 mmol) in acetic acid (37 mL), ammonium acetate (1.695 g, 29.136 mmol) was added. The reaction mixture was heated at reflux for 3 days. The reaction mixture was poured over ice water and the mixture was neutralised with sodium carbonate. The precipitate (white solid) was filtered, washed with cool water and dried. The solid was dissolved in DCM and washed with water. The organic phase was separated, dried over $Na_2SO_4$ and concentrated to obtain a white solid which was purified by biotage (eluent: cyclohexane/EtOAc 100/0 to 80/20 and then DCM/MeOH 100/0 to 50/50 to obtain a white solid, 840 mg of intermediate II-8 (61% yield).

Preparation of Intermediate II-7

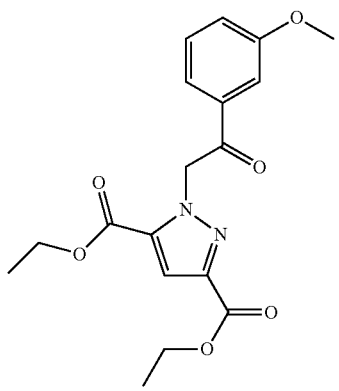 [SMILES: CCOC(=O)c1cc(C(=O)OCC)n(CC(=O)c2cccc(OC)c2)n1]

To a solution of diethyl 3,5-pyrazoledicarboxylate (1 g, 4.712 mmol) in acetone (20 ml), 2-bromo-3'-methoxyacetophenone (1.079 g, 4.712 mmol) and potassium carbonate (0.716 mg, 5.184 mmol) were added. The reaction mixture was stirred at RT 12 h. The solvent was evaporated and residue was dissolved in DCM and washed with water. The organic phase was dried over $Na_2SO_4$ and concentrated in vacuo. The residue, a yellow oil, (1.605 g, 95% yield) was used in the next reaction step without further purification as intermediate II-7.

Preparation of Final Product 3-6

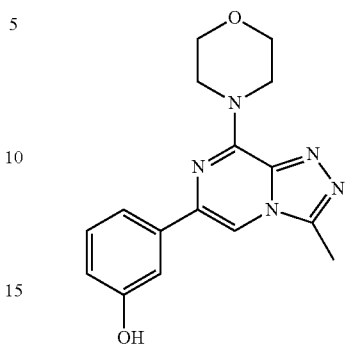

To a stirred solution of product 3-3 (40 mg, 0.123 mmol, 1 eq.) in DCM (2 mL) at rt, boron fluoride-dimethyl sulfide complex (0.129 mL, 1.229 mmol, 10 eq.) was added. The mixture was stirred at rt for 24 h. $NaHCO_3$ (sat.) was added and the mixture was extracted (with DCM/MeOH: 90/10). The organic phase was separated, dried ($Na_2SO_4$) and evaporated to dryness. The residue was precipitated from MeOH/ $Et_2O$, filtered off and dried to yield 0.036 g of final product 3-6, 94%.

Preparation of Final Product 3-3

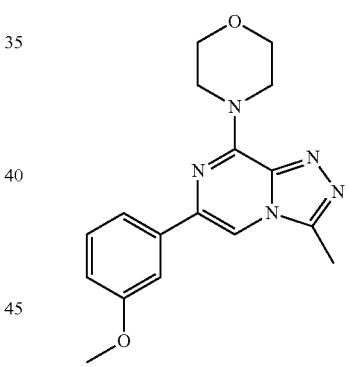

To a mixture of intermediate II-4 (0.035 g, 0.117 mmol, 1 eq.), 3-methoxyphenylboronic acid (21 mg, 0.141 mmol, 1.2 eq.), and $PdCl_2$ (dppf) (10 mg, 0.012 mmol, 0.1 eq.), in DME (2 ml), a saturated solution of potassium carbonate (0.2 ml) was added. The mixture was heated at 130° C. under microwave irradiation for 15 min. The reaction mixture was diluted with DCM and water was added. The organic phase was separated, dried ($Na_2SO_4$) and evaporated to dryness. The residue was purified by CCTLC in a chromatotron, eluent: DCM/MeOH, 96/4, the desired fractions were collected and the solvent was evaporated. Yielding final product 3-3: 0.020 g, Y: 52%.

Final compound 3-4 was prepared following a similar synthetic route to final compound 3-8, by using indazole-4-boronic acid hydrochloride as the coupling agent (CAS: 1023595-17-6) and intermediate II-4. Yield: 47% Final compound 3-5 was prepared following similar synthetic route to final compound 3-8, by using 2-aminopyrimidine-5-boronic acid, pinacol ester as the coupling agent (CAS: 402960-38-7) and intermediate II-4. Yield: 7%.

Preparation of Intermediate II-4

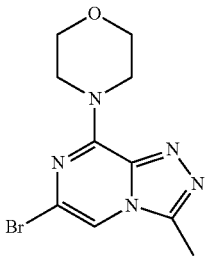 [SMILES: Cc1nnc2c(N3CCOCC3)nc(Br)cn12]

A mixture of intermediate II-3 (1.375 mmol, 1 eq.) in triethyl orthoacetate (4 mL) was heated at 140° C. for 2 h. The solid was filtered off and dried, yielding intermediate II-4: 0.035 g, 8%.

Preparation of Intermediate II-3

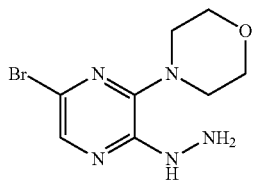

Intermediate II-2 (0.383 g, 1.375 mmol, 1 eq.) and hydrazine hydrate (0.535 mL, 5.5 mmol, 4 eq.) were dissolved in DMSO (4 mL) and heated at reflux for 2 h. EtOAc and water were added. The organic phase was separated, dried ($Na_2SO_4$), filtered and evaporated to dryness. The residue was taken up into $CH_3CN$ and water and liophilised. The residue was used in the next step without further purification as intermediate II-3.

Preparation of Intermediate II-2

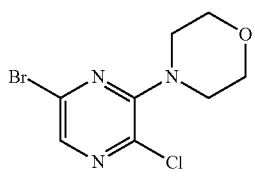

To a well stirred solution of intermediate II-1 (0.5 g, 1.930 mmol, 1 eq.) in DCM (5 mL) cooled to 0° C., titanium(IV) chloride (1 M in DCM) (1.93 mL, 1.93 mmol, 1 eq.) was added in one portion. Tert-butyl nitrite (0.459 mL, 3.859 mmol, 2 eq.) is then added dropwise. The ice bath is removed and the reaction is allowed to proceed at rt. More $TiCl_4$ (1 M in DCM) (2.31 mL, 2.31 mmol, 1.2 eq.) was added and the mixture was stirred for 1 h. The solid was filtered off and dried and used in the next step without further purification as intermediate II-2.

Preparation of Intermediate II-1

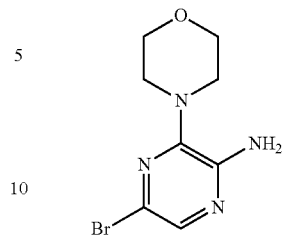

A solution of product 2-amino-3,5-dibromo-4-ylpyrazine (cas: 117719-17-2), (40 g, 158 mmol, 1.0 eq) in morpholine (41.5 ml, 474 mmol 3.0 eq) was heated at 120° C. in a parr reactor for 24 h. A brown solid appears. The solid was suspended in DCM and washed with $Na_2CO_3$ aq. sat (twice). The organic phase was dried ($MgSO_4$), filtered and solvent removed in vacuo to give a brown solid, which was triturated from $Et_2O$ to afford the desired product (30.54 g, 74%) as a pale brown solid as II-1.

Preparation of Final Compound 3-7

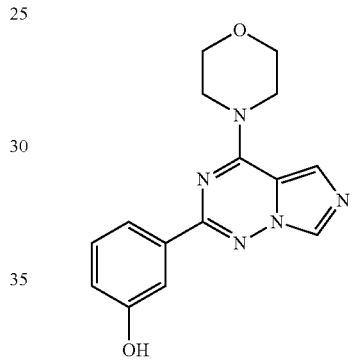

$BF_3Me_2$ S complex was added to a 0° C. mixture of intermediate II-25 in DCM. The reaction was stirred at rt for 48 h. MeOH was added at 00° C. and the mixture was stirred for 1 h, then solvents were removed under reduced pressure, additional MeOH (15 mL) was added and then evaporated. The residue was treated with water and 32% $NH_4OH$ until basic pH. The mixture was extracted with EtOAc (x3). Combined organic layers were washed with brine, dried and evaporated.

The residue was purified on silica gel (biotage DCM/MeOH 5 to 10% MeOH) to give final compound 3-7, 17 mg. Yield 66%.

Preparation of Intermediate II-25

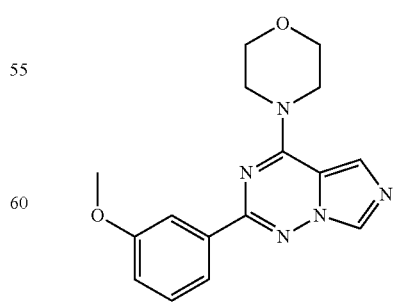

Morpholine was added to a mixture of intermediate II-26 and TEA in dioxane. The reaction mixture was stirred at rt for 4.5 h. Solvents were evaporated to dryness. The residue was diluted with EtOAc, washed with NaHCO₃, brine, dried and evaporated. The residue was used in next reaction without further purification. Yield 100%.

Preparation of Intermediate II-26

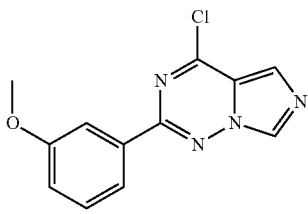 [SMILES: COc1cccc(-c2nc(Cl)c3cncn3n2)c1]

A mixture of intermediate II-27 and N,N-dimethylaniline in phosphorus oxychloride was stirred in a sealed tube at 90° C. for 4 h. POCl₃ was evaporated and ice was added to the residue. The mixture was extracted with CHCl₃ (x3).

The combined organic layers were dried and evaporated. The residue was purified on silica gel (biotage c-Hex/EtOAc 20% then 30% then 50% EtOAc) to give intermediate II-26, 23 mg, yield 21%.

Preparation of Intermediate II-27

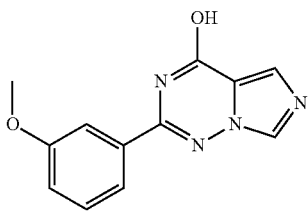 [SMILES: COc1cccc(-c2nc(O)c3cncn3n2)c1]

A mixture of intermediate II-28 and t-BuOK in t-BuOH was heated at 160° C. in a sealed vessel for 24 h, then it was stirred at rt for 2-3 days. The reaction mixture was heated at 16000 for additional 24 h. After cooling down to rt the mixture was neutralised with 1N HCl, diluted with EtOAc and a small amount of water was added. The aqueous layer was extracted with EtOAc (x2). Combined organic layers were washed with brine, dried and evaporated. The white residue was only partially soluble in MeOH, DCM. The residue was a 1:1 mixture of intermediate II-27 and starting material (intermediate II-28) and it was used as such in the next reaction.

Preparation of Intermediate II-28

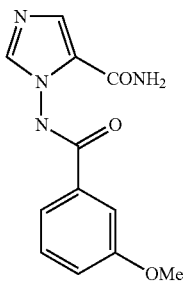 [SMILES: COc1cccc(C(=O)Nn2cncc2C(N)=O)c1]

3-Methoxybenzoyl chloride was added to a mixture of intermediate II-29 in pyridine. The reaction mixture was stirred at 60° C. for 2 h then overnight at rt. Solvents were evaporated to dryness. EtOAc was added and the mixture was washed with sat aqueous NaHCO₃. An emulsion was formed. It was collected with the aqueous layer. The organic layer was dried and evaporated to afford only 115 mg. On standing, the emulsion started to give a solid. Filtration, washing with H₂O and trituration with Et₂O gave 292 mg of a white solid as intermediate II-44. The residue obtained from the organic layer was treated with water, the solid was filtered, washed with water and then triturated with Et₂O to give 40 mg more of intermediate II-28. Yield 56%

Preparation of Intermediate II-29

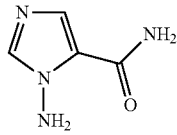

A mixture of intermediate II-30 and NH₄Cl in 7N NH₃/MeOH solution was heated at 90° C. (sand bath) in a closed vessel for 72 h. The reaction was heated at 11° C. for 24 h. Fresh 7N NH₃/MeOH was added (20 mL) and the reaction was heated at 120° C. for 5 h. Solvents were evaporated to dryness. The residue was partitioned between EtOAc/water. The organic layer was washed once with water, dried and evaporated to give only 11 mg of residue. The aqueous layer was evaporated to dryness to give 400 mg of a white solid, as a mixture of desired product, intermediate II-29 and NH₄C salts (yield >100%) that was used as such in next reaction.

Preparation of Intermediate II-30

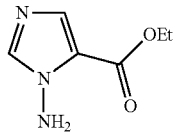 [SMILES: CCOC(=O)c1cncn1N]

LiHMDS was added to a −10° C. solution of ethyl imidazole-4-carboxylate in DMF. After 15 min, o-diphenylphosphinylhydroxylamine (CAS: 72804-96-7) was added in one portion and the mixture was stirred at rt for 6 h. The reaction was quenched with water (an exothermic reaction occcurs) until a clear solution is obtained. The solvents were removed under reduced pressure. The residue was dissolved in water and it was extracted with DCM (x3). Combined organic layers were dried and evaporated. The residue was purified on silica gel (biotage, DCM/MeOH 0 to 10% MeOH) to obtain: 356 mg of desired product, intermediate II-30. Yield 65%.

Preparation of Final Compound 3-8

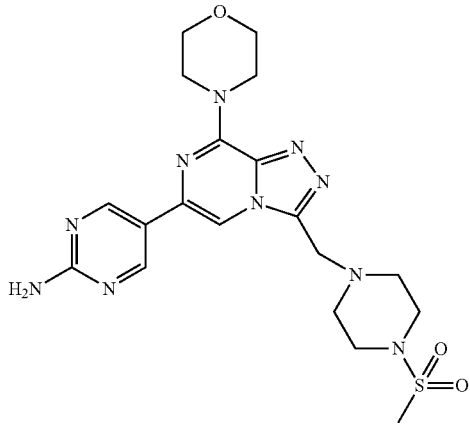 [SMILES: CS(=O)(=O)N1CCN(Cc2nnc3c(N4CCOCC4)nc(-c4cnc(N)nc4)cn23)CC1]

To a mixture of intermediate II-5 (0.1 g, 0.217 mmol, 1 eq.), 2-aminopyrimidine-5-boronic acid, pinacol ester (48 mg, 0.217 mmol, 1 eq.), and $PdCl_2$ (dppf) (18 mg, 0.022 mmol, 0.1 eq.), in DME (2 ml), a saturated solution of potassium carbonate (0.2 ml) was added. The mixture was heated at 130° C. for 2 h. The reaction mixture was diluted with DCM and water was added. The organic phase was separated, dried ($Na_2SO_4$) and evaporated to dryness. The residue was purified by CCTLC in a chromatotron, then by HPLC. Yielding: 3 mg, Y:3% of final compound 3-8.

Preparation of Intermediate II-5

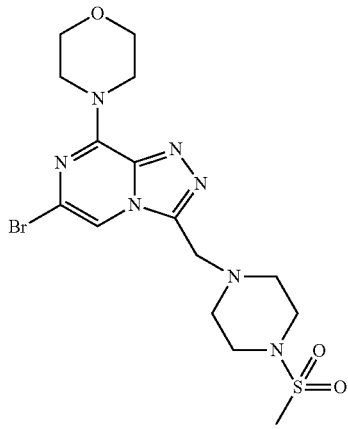 [SMILES: CS(=O)(=O)N1CCN(Cc2nnc3c(N4CCOCC4)nc(Br)cn23)CC1]

A mixture of the reaction crude 11-6 (1.262 mmol, 1 eq.), methylsulfonylpiperazine (0.207 g, 1.262 mmol, 1 eq.) and $K_2CO_3$ (0.262 g, 1.893 mmol, 1.5 eq.) in AcCN (8 mL) was heated at 120° C. in a seal tube for 3 h. Water and AcOEt were added, the organic phase was separate, dried ($Na_2SO_4$), filtered and evaporated. The residue was purified by CCTLC in a chromatotron: DCM/MeOH, 96/4. The desired fractions were collected, yielding: 100 mg.

Preparation of Intermediate II-6

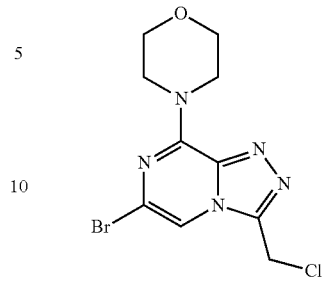

A mixture of intermediate II-3 (0.346 g, 1.262 mmol, 1 eq.) in 2-chloro-1,1,1-triethoxyethane (2 mL) was heated at 140° C. for 1 h. The solvent was evaporated, and the residue was used in the next step without further purification.

Preparation of Final Product 3-9

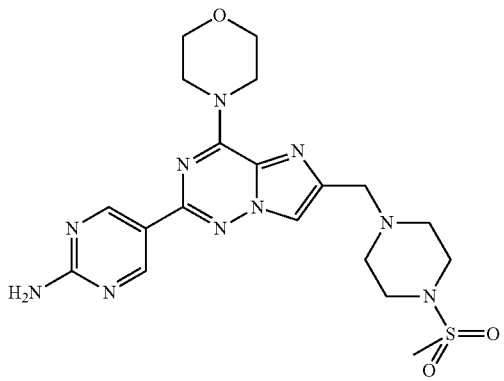 [SMILES: CS(=O)(=O)N1CCN(Cc2cn3nc(-c4cnc(N)nc4)nc(N4CCOCC4)c3n2)CC1]

To a solution of intermediate II-10 (0.140 g, 0.327 mmol, 1.0 eq) in DME (5.0 mL) were added 2-aminopyrimidine-5-boronic acid, pinacol ester (0.145 g, 0.655 mmol, 2.0 eq), Pd(dppf)$Cl_2$ (0.271 g, 0.327 mmol, 1.0 eq) and $Cs_2CO_3$ (0.213 g, 0.655 mmol, 2.0 eq). The reaction mixture was heated at 130° C. for 18 h. The crude mixture was filtered off and the solvent was removed in vacuo to give a dark oil which was purified by column chromatography and then by HPLC preparative to afford the desired product (0.010 g, 7%,) as a white solid.

Preparation of Intermediate II-10

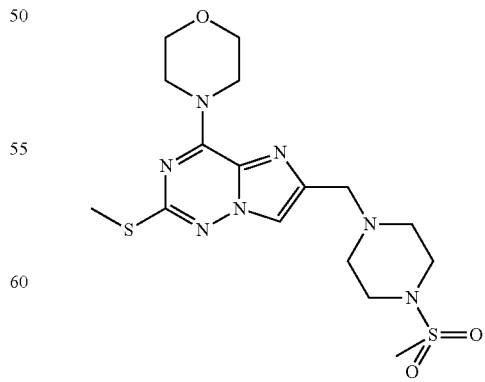

A mixture of intermediate II-11 (0.091 g, 0.326 mmol, 1.0 eq), 1-(methylsulfonyl)piperazine (0.070 g, 0.424 mmol, 1.3 eq) and trimethyl orthoformate (0.356 mL, 0.326 mmol, 10.0 eq) in DCE (10 mL) was stirred at rt for 4 h. Sodium triacetoxyborohydride (0.090 g, 0.424 mmol, 1.3 eq) was added to the reaction mixture and it was stirred at rt for 18 h. The solvent was removed in vacuo and redissolved in DCM (50 mL). Then, the mixture was extracted with brine (20 mL).

The organic layer was dried ($MgSO_4$), filtered and evaporated to afford the desired product (0.140 g, 99%) as a white solid.

Preparation of Intermediate II-11

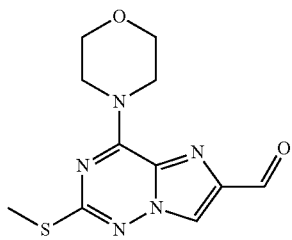 [SMILES: CSc1nc(N2CCOCC2)c2nc(C=O)cn2n1]

To a solution of intermediate II-12 (0.160 g, 0.57 mmol, 1.0 eq) in chloroform (20 mL) was added manganese dioxide (0.841 g, 9.6 mmol, 17.0 eq). The reaction mixture was refluxed for 2 h. The solution was filtered off and the solvent removed in vacuo to afford the desired product (0.091 g, 57%) as a white solid.

Preparation of Intermediate II-12

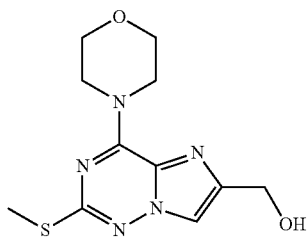 [SMILES: CSc1nc(N2CCOCC2)c2nc(CO)cn2n1]

To a solution of intermediate II-13 (0.320 g, 0.990 mmol, 1.0 eq) in THF (20 mL) at 0° C., was added a solution of lithium aluminum hydride 1M in THF (2.47 mL, 2.47 mmol, 2.5 eq). The reaction mixture was sirred at 0° C. for 1 h. Then, water (0.3 mL) was added and the crude mixture stirred for 10 min at 0° C. NaOH 2M (0.6 mL) was added and again stirred at 000° C. for 10 min. Finally, water (0.3 mL) was added again and stirred for 10 min more. The crude mixture was filtered off to remove impurities. Solvent was removed in vacuo to give a yellow solid which was triturated from MeOH to afford the desired product (0.157 g, 56%) as a white solid.

Preparation of Intermediate II-13

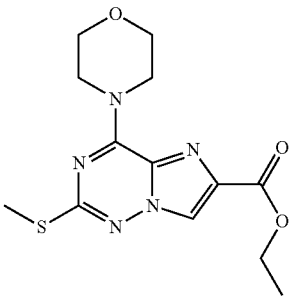 [SMILES: CCOC(=O)c1cn2nc(SC)nc(N3CCOCC3)c2n1]

To a solution of 1,2,4-triazin-6-amine, 3,5-bis(methylthio), CAS:84582-90-1 (0.3 g, 1.59 mmol, 1.0 eq) in dry toluene (30 mL) were added ethyl bromopyruvate (1.0 mL, 7.96 mmol, 5.0 eq) and p-toluensulfonic acid (0.048 g, 0.255 mmol, 0.16 eq). The reaction mixture was refluxed for 18 h. Then, solvent was removed in vacuo and the residue dissolved in DCM (100 mL). The organic solvent was washed with water (2×50 mL), dried ($MgSO_4$) and solvent removed in vacuo to give a dark oil. The resulting residue was dissolved in MeCN (20.0 mL) and morpholine (1.39 mL, 15.9 mmol, 10.0 eq) was added. The reaction mixture was heated at 85° C. until the completion of the reaction. The solvent was removed in vacuo and the residue dissolved in DCM (150 mL). The organic solvent was washed with water (2×50 mL), dried ($MgSO_4$), filtered and evaporated to obtain a dark oil which was triturated from EtOH to afford the desired product (0.325 g, 63%, 10922702) as a pale brown solid. The resulting residue was used in next reaction step without further purification.

Preparation of Final Product 3-10

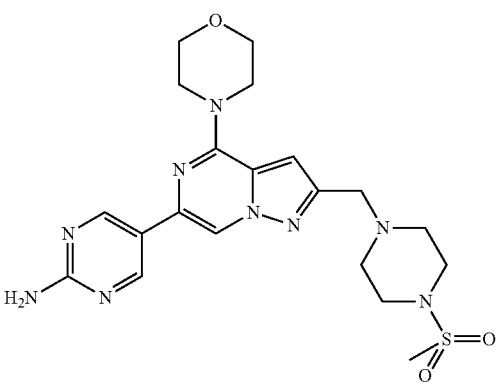 [SMILES: CS(=O)(=O)N1CCN(Cc2cc3c(N4CCOCC4)nc(-c4cnc(N)nc4)cn3n2)CC1]

A solution of intermediate II-14 (98 mg, 0.14 mmol) in 1,2 DCE (4 mL) was cooled to 0° C. Then, trifluoroacetic acid (1.75 mL) and 98% $H_2SO_4$ (two drops) were added and the mixture was stirred for 12 h at room temperature. The solvents were removed in vacuo to give a brown residue that was dissolved in water (1 mL) and cooled to 0° C. Aqueous $NH_4OH$ was added up to pH~8 and the resulting white solid was filtered, washed with water and dried to give a white solid that was combined with a second batch followed by purification by column chromatography (DCM/MeOH 100:1 to 100:5 mixtures) to afford 5-[2-(4-methanesulfonyl-piperazin-1-ylmethyl)-4-morpholin-4-yl-pyrazolo[1,5-a]pyrazin-6-yl]-pyrimidin-2-ylamine as a white solid (41 mg, 52% combined yield).

Preparation of Intermediate II-14

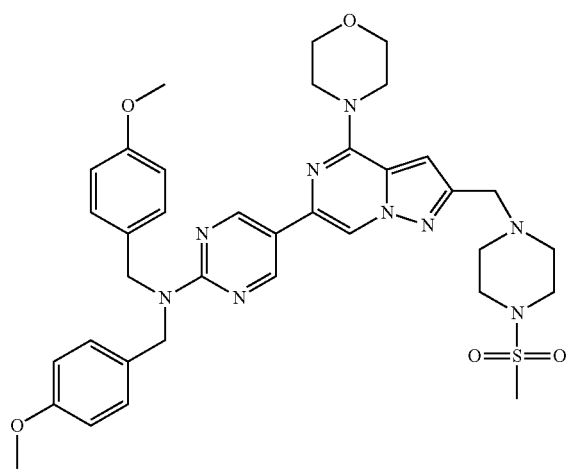 [SMILES: COc1ccc(CN(Cc2ccc(OC)cc2)c2ncc(-c3cn4nc(CN5CCN(S(C)(=O)=O)CC5)cc4c(N4CCOCC4)n3)cn2)cc1]

A solution of intermediate II-15 (200 mg, 0.35 mmol) and MnO$_2$ (500 mg, 5.75 mmol) in 1,2-DCE (10 mL) was stirred for 5 h at room temperature showed the formation of aldehyde and some starting material remaining. The mixture was filtered, the filtrate washed with DCM and EtOAc and the solvents removed in vacuo to give a green oil (268 mg). This oil was dissolved in 1,2-DCE (10 mL) and 1-methanesulfonyl-piperazine (115 mg, 0.7 mmol), AcOH (2 drops) and Na$_2$SO$_4$ (1 g) were added and the mixture was stirred for 3 h at room temperature. Sodium triacetoxyborohydride (111 mg, 0.52 mmol) was added and the mixture was stirred for 3 h at room temperature and the solvents removed in vacuo to give a white residue that was purified by column chromatography (EtOAc/MeOH mixtures) to give desired compound as a colourless oil (118 mg, 47% yield).

Preparation of Intermediate II-15

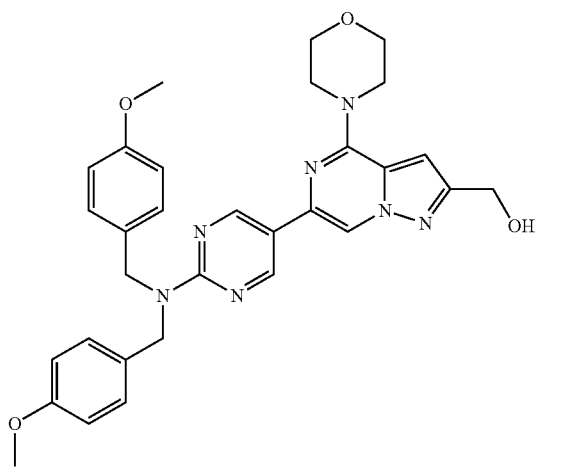 [SMILES: COc1ccc(CN(Cc2ccc(OC)cc2)c2ncc(-c3cn4nc(CO)cc4c(N4CCOCC4)n3)cn2)cc1]

A solution of intermediate II-16 (300 mg, 0.49 mmol) in dry THF (30 mL) was cooled to 0° C. Then LiAlH$_4$ (1M solution in THF, 1.0 mL, 1.0 mmol) was added dropwise and the solution was stirred for 4 h at 00° C. The mixture was quenched sequentially with water (0.30 mL), 2N NaOH (0.30 mL) and water (0.6 mL) and stirred for 10 minutes. The resulting solid was filtered off and washed with EtOAc and MeOH. The solvents were removed in vacuo and the residue was purified by column chromatography (EtOAc as eluant) to give desired product (208 mg, 75% yield) as a yellow oil.

Preparation of Intermediate II-16

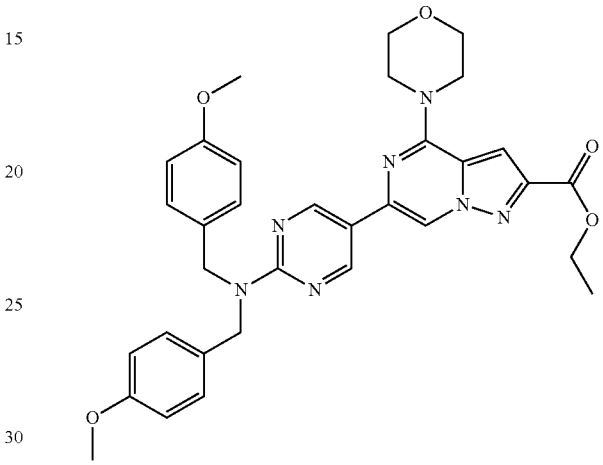

A mixture of intermediate II-17 (1.89 g, theorical 1.19 mmol), morpholine (2.01 mL, 23.8 mmol) and triethylamine (3.36 mL, 23.8 mmol) in dioxane (50 mL) was stirred at room temperature for 3 days. The solvent was removed in vacuo and the residue was purified by column chromatography (using hexane (EtOAc mixtures as eluents) to give 6-{2-[bis-(4-methoxy-benzyl)-amino]-pyrimidin-5-yl}-4-morpholin-4-yl-pyrazolo[1,5-a]pyrazine-2-carboxylic acid ethyl ester as a white solid (444 mg).

Preparation of Intermediate II-17

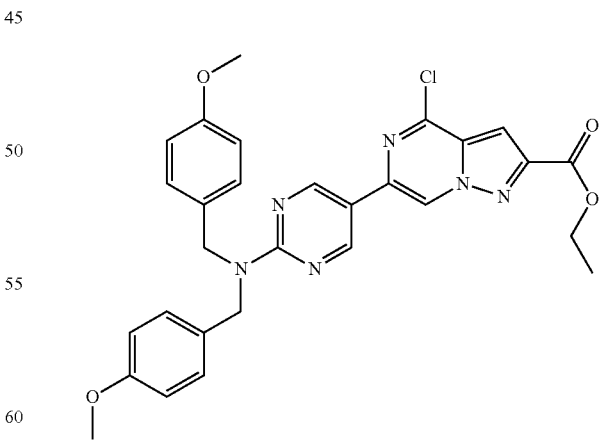

A mixture of intermediate II-18 (650 mg, 1.19 mmol) and N,N-dimethylaniline (0.5 mL) in POCl$_3$ (6 mL) was stirred for 3 h at 80° C., then for a further 18 h at 80° C. On cooling to room temperature, more N,N-dimethylaniline (0.5 mL) and POCl$_3$ (6 mL) were added and the mixture was heated for 24 h at 90° C. POCl₃ was removed in vacuo, the residue taken up in DCM (200 mL) and the mixture poured onto ice. After stirring for 15 minutes, NaHCO₃ was added portionwise up to pH~8 and the organic layer was separated, washed with water (25 mL), dried (Na₂SO₄) and the solvent removed in vacuo to give a blue oil (1.89 g) which was used in next reaction step without further purification.

Preparation of Intermediate II-18

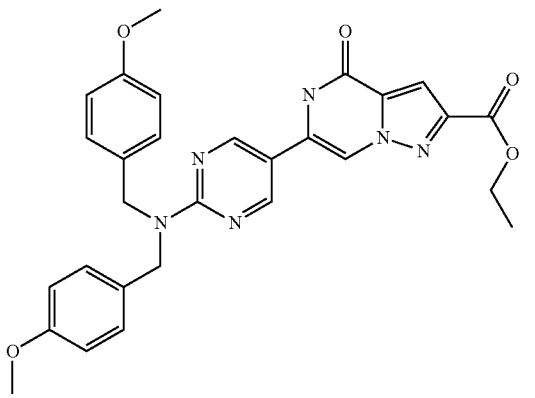 [SMILES: CCOC(=O)c1cc2c(=O)[nH]c(-c3cnc(N(Cc4ccc(OC)cc4)Cc4ccc(OC)cc4)nc3)cn2n1]

A mixture of intermediate II-19 (220 mg, 0.37 mmol) and NH₄OAc (0.383 g, 4.96 mmol) in EtOH (5 mL) was heated for 1 h at 150° C. under microwave irradiation. On cooling to 0° C., the crude reaction mixture was combined with a second batch and the resulting solid was filtered off, washed with water/EtOH (1:1) and dried to give desired product as a white solid (704 mg, 94% combined yield).

Preparation of Intermediate II-19

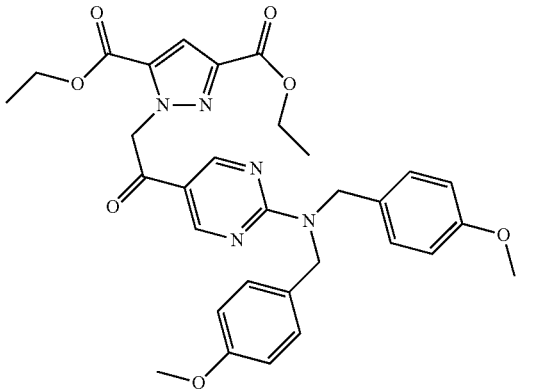 [SMILES: CCOC(=O)c1cc(C(=O)OCC)n(CC(=O)c2cnc(N(Cc3ccc(OC)cc3)Cc3ccc(OC)cc3)nc2)n1]

A mixture of diethyl 3,5-pyrazoledicarboxylate (539 mg, 2.54 mmol), intermediate 11-20 (1.21 g, 2.65 mmol) and K₂CO₃ (440 mg, 3.18 mmol) in acetone (20 mL) was stirred overnight at room temperature. Then, water (50 mL) was added and the mixture was extracted with DCM (4×150 mL). The combined organic layers were washed with brine (50 mL), dried (MgSO₄) and the solvent removed in vacuo to give a residue that was purified by column chromatography (hex-anes/EtOAc 7:3 as eluent) to give an oil that was triturated from ether to give desired product as a white solid (898 mg, 66% yield).

Preparation of Intermediate II-20

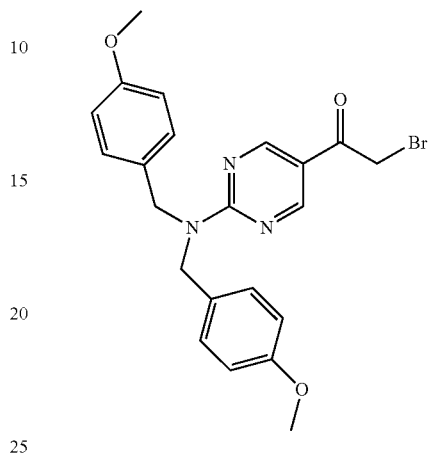

A mixture of intermediate II-21 (879 mg, 2.33 mmol) and dry TEA (0.96 mL, 7 mmol) in dry THF (50 mL) was cooled to 0° C. Then, trimethylsilyl trifluoromethanesulfonate (1.27 mL, 7 mmol) was added dropwise and the mixture was stirred for 2 h at 0° C. Then, NBS (626 mg, 3.45 mmol) was added portionwise and the mixture was stirred for 1 h at 0° C.

The reaction mixture was diluted with water (30 mL) and extracted with EtOAc (4×150 mL). The combined organic layers were washed with saturated aqueous NaHCO₃, dried (MgSO₄) and the solvent removed in vacuo to give desired compound as a brown oil (1.21 g). The product was used without further purification in next step.

Preparation of Intermediate II-21

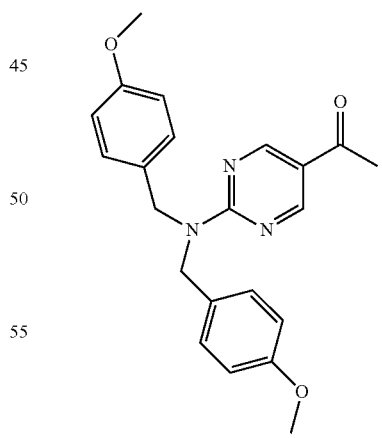

A mixture of intermediate II-22 (1.81 g, 4.37 mmol), tributyl(1-ethoxyvinyl)tin (1.42 mL, 4.24 mmol) and dichlorobis(triphenylphosphine)palladium(II) (0.15 g, 0.21 mmol) in dry DMF (15 mL) was heated at 100° C. for 4 h, and then for a further 18 h at 100° C. On cooling, the reaction mixture was diluted with ether (300 mL), the mixture was treated with aqueous 15% KF solution (100 mL). The mixture was vigorously stirred for 1 h, the organic layer was separated and washed with saturated NaHCO$_3$ (50 mL), brine (50 mL), dried (MgSO$_4$) and the solvents removed in vacuo to give a residue that was purified by column chromatography (10:1 cyclohexane/EtOAc as eluant) to give 1-{2-[bis-(4-methoxy-benzyl)-amino]-pyrimidin-5-yl}-ethanone (997 mg).

Preparation of Intermediate II-22

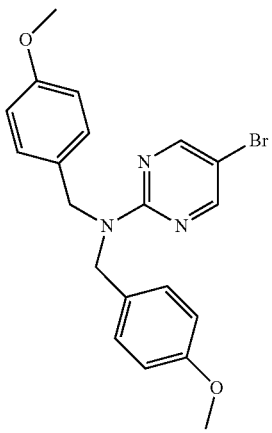 [SMILES: COc1ccc(CN(Cc2ccc(OC)cc2)c2ncc(Br)cn2)cc1]

A mixture of 2-chloro-5-bromopyrimidine (1.0 g, 5.16 mmol), N-(4-methoxybenzyl)(4-methoxyphenyl)methanamine hydrochloride, (cas 854391-95-0) (1.59 g, 5.418 mmol) and DIPEA (2.68 mL, 15.48 mmol) in dry dioxane (10 mL) was heated for 1 h at 160° C. under microwave irradiation. On cooling, the mixture was diluted with EtOAc (200 mL) and the organic phase was washed with saturated aqueous NaHCO$_3$ (50 mL), brine (50 mL), dried (MgSO$_4$) and the solvent removed in vacuo to give a residue that was purified by column chromatography (hexane/EtOAc mixtures-20:1 to 10:1- as eluent) to give desired product as a white solid (1.81 g, 85% yield).

Preparation of Final Product 3-11

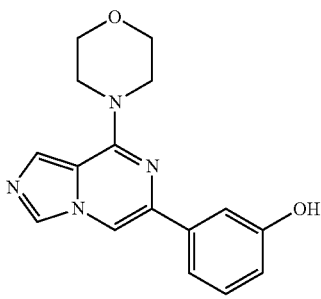

A mixture of final product 3-12 (50 mg, 0.16 mmol) in dry DCM (2 mL) was cooled to 0° C. and then boron fluoride-dimethyl sulfide complex (0.5 mL, 3.1 mmol) was added dropwise and the mixture was stirred for 18 h at room temperature. The mixture was cooled to 0° C. and MeOH (2 mL) was added dropwise and the mixture was stirred 1 h at room temperature. The solvents were removed in vacuo, the residue was dissolved in MeOH (5 mL) and the mixture stirred for 1 h at room temperature. The solvents were removed in vacuo to give a brown oil that was suspended in water (2 mL) and 28% aqueous solution of NH$_4$OH (in an amount such that pH was up to pH~8). The resulting solid was filtered, washed with water and dried (21 mg) to yield final compound 3-11.

Preparation of Final Product 3-12

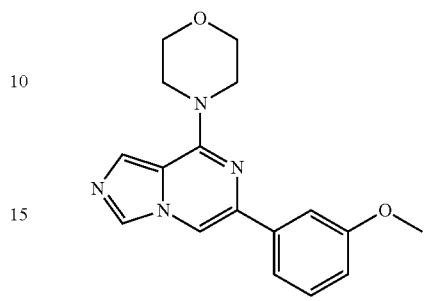

A mixture of intermediate II-31 (150 mg, 0.58 mmol), morpholine (0.1 mL, 1.16 mmol) and triethylamine (0.3 mL, 2.12 mmol) in dioxane (2 mL) was stirred at room temperature for 18 h. The mixture, was then, refluxed for 6 h. The solvent was removed in vacuo and the residue was purified by column chromatography (using DCM/MeOH mixtures as eluents) to give final product 3-12, 6-(3-methoxy-phenyl)-8-morpholin-4-yl-imidazo[1,5-a]pyrazine (10843040) as a yellow solid (159 mg, 89% yield).

Preparation of Intermediate II-31

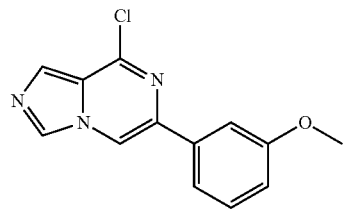 [SMILES: COc1cccc(-c2cn3cncc3c(Cl)n2)c1]

A mixture of intermediate II-32 (387 mg, 1.60 mmol) and N,N-dimethylaniline (0.6 mL) in POCl$_3$ (2.2 mL) was stirred at room temperature for 18 h. Then, the mixture was heated at 90° C. for 5 h. On cooling, POCl$_3$ was removed in vacuo and the residue taken up in DCM (100 mL) and poured onto ice. After stirring for 15 minutes, K$_2$CO$_3$ was added portionwise up to pH~8, the organic layer was separated, washed with water (25 mL), dried (Na$_2$SO$_4$) and the solvent was removed in vacuo to give a brown residue that was purified by column chromatography (DCM/MeOH 100:1 as eluent) to give intermediate II-31, as a yellow solid (156 mg).

Preparation of Intermediate II-32

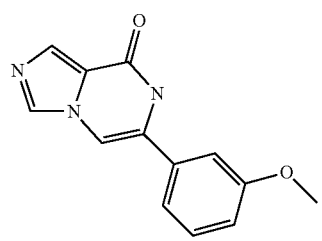 [SMILES: COc1cccc(-c2cn3cncc3c(=O)[nH]2)c1]

A mixture of intermediate II-33 (787 mg, 3.07 mmol) and imidazole (5.22 g, 76.75 mmol) was heated at 170° C. for 18 h. On cooling, water (25 mL) was added and the resulting solid was filtered off, washed with water and dried to give a brown solid that was recrystallised from MeOH affording 6-(3-methoxy-phenyl)-7H-imidazo[1,5-a]pyrazin-8-on, intermediate II-32, as a brown solid (392 mg) which was used in next reaction step without further purification.

Preparation of Intermediate II-33

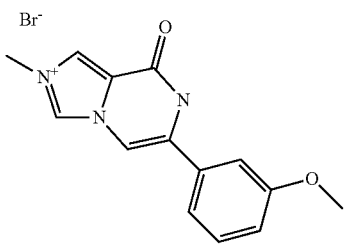

A mixture of 1-Methyl-1H-imidazole-4-carboxamide, (cas:129993-47-1) (560 mg, 4.47 mmol, 1 eq) and 2-bromo-3'-methoxyacetophenone (1.124 g, 4.91 mmol, 1.1 eq) in MeCN (10 mL) and DMF (3 mL) was refluxed for 18 h. On cooling to 0° C., the resulting solid was filtered off, washed with MeCN and dried to give 6-(3-methoxy-phenyl)-2-methyl-8-oxo-7,8-dihydro-imidazo[1,5-a]pyrazin-2-ium; bromide, intermediate II-33, (796 mg, 53% yield) as a white solid.

Preparation of Compound 3-13

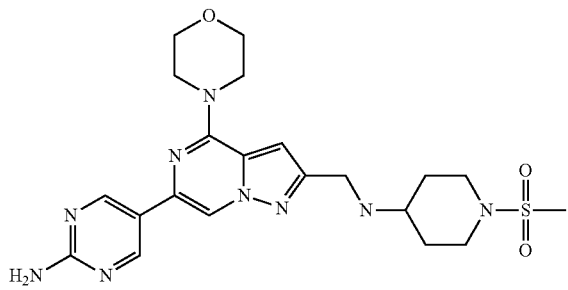 [SMILES: CS(=O)(=O)N1CCC(NCc2cc3c(N4CCOCC4)nc(-c4cnc(N)nc4)cn3n2)CC1]

Following a similar procedure described for the synthesis of final product 3-10 afforded 5-{2-[(1-methanesulfonyl-piperidin-4-ylamino)-methyl]-4-morpholin-4-yl-pyrazolo[1,5-a]pyrazin-6-yl}-pyrimidin-2-ylamine as a yellowish solid (31.2 mg, 64% yield in the last step).

$^1$H NMR (DMSO, 300 MHz): δ 8.86 (s, 2H), 8.64 (s, 1H), 6.96 (s, 1H), 6.83 (s, 2H), 3.89 (s, 2H), 3.78 (s, 8H), 3.45 (m, 2H), 2.83 (s, 1H), 2.82 (s, 3H), 2.75 (m, 2H), 1.92 (m, 2H), 1.36 (m, 2H).

LC/MS (Method 1): Rt 2.23, [M+1]$^+$: 488.3

IC50 PI3Kα (μM): 0.058

Preparation of Compound 3-14

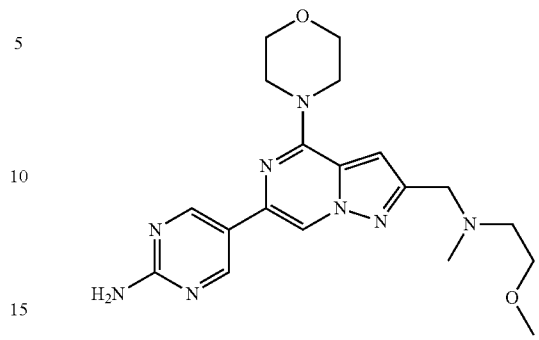

Following a similar procedure described for the synthesis of final product 3-10, afforded 5-(2-{[(2-methoxy-ethyl)-methyl-amino]-methyl}-4-morpholin-4-yl-pyrazolo[1,5-a]pyrazin-6-yl)-pyrimidin-2-ylamine as a white solid (31.7 mg, 82% yield in the last step).

$^1$H NMR (300 MHz, DMSO) δ 8.88 (s, 2H), 8.69 (s, 1H), 7.03 (s, 1H), 6.86 (s, 2H), 4.02 (s, 2H), 3.79 (s, 8H), 3.52 (m, 2H), 3.27 (s, 3H), 2.87 (s, 2H).

LC/MS (Method 3): Rt 0.328, [M+1]$^+$: 399.3

IC50 PI3Kα (μM): 0.106

Preparation of Compound 3-15

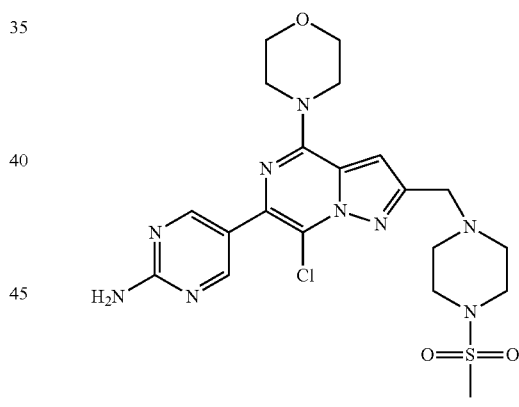

A mixture of final product 3-10 (22 mg, 0.046 mmol, 1 eq) and n-chlorosuccinimide (6.2 mg, 0.046 mmol) in DCM (2 mL) was stirred for 18 h at room temperature. Then, more NCS (2 mg, 0.015 mmol) was added and the mixture was stirred for 48 h at room temperature. The organic solvents were removed in vacuo and the residue was purified by column chromatography (EtOAc/MeOH mixtures) to give 5-[7-chloro-2-(4-methanesulfonyl-piperazin-1-ylmethyl)-4-morpholin-4-yl-pyrazolo[1,5-a]pyrazin-6-yl]-pyrimidin-2-ylamine as a white solid, final compound 3-15 (3 mg, 23% yield).

$^1$H NMR (300 MHz, DMSO) δ 8.67 (s, 2H), 7.13 (s, 1H), 6.97 (s, 2H), 3.77 (s, 2H), 3.75 (m, 4H), 3.12 (bs, 4H), 2.87 (s, 3H), 2.55 (bs, 4H).

LC/MS (Method 1): Rt 2.454, [M+1]$^+$: 507.9

Preparation of Compound 3-16

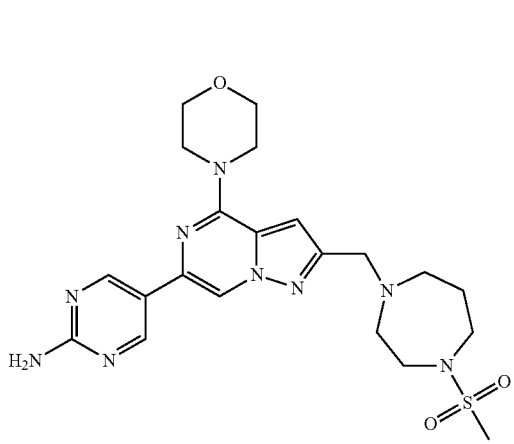 [SMILES: CS(=O)(=O)N1CCCN(Cc2cc3c(N4CCOCC4)nc(-c4cnc(N)nc4)cn3n2)CC1]

Following a similar procedure described for the synthesis of final product 3-10, afforded 5-[2-(4-methanesulfonyl-[1,4]diazepan-1-ylmethyl)-4-morpholin-4-yl-pyrazolo[1,5-a]pyrazin-6-yl]-pyrimidin-2-ylamine as a yellowish solid (13.6 mg, 33% yield in the last step).

$^1$H NMR analysis (300 MHz, DMSO) δ 8.86 (s, 2H), 8.67 (s, 1H), 6.92 (s, 1H), 6.83 (s, 2H), 3.83 (s, 2H), 3.77 (s, 8H), 3.3 (m, 4H), 2.88 (s, 3H), 2.72 (m, 4H), 1.79 (m, 2H).

LC/MS (Method 1): Rt 2.267, [M+1]$^+$: 488.3

IC50 PI3Kα (μM): 0.013

Preparation of Compound 3-17

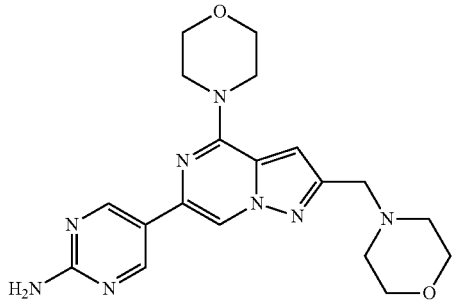 [SMILES: Nc1ncc(-c2cn3nc(CN4CCOCC4)cc3c(N3CCOCC3)n2)cn1]

Following a similar procedure described for the synthesis of final product 3-10, afforded 5-(4-morpholin-4-yl-2-morpholin-4-ylmethyl-pyrazolo[1,5-a]pyrazin-6-yl)-pyrimidin-2-ylamine as a white solid (27.9 mg, 70% yield in the last step).

$^1$HNMR (300 MHz, DMSO) δ 8.86 (s, 2H), 8.66 (s, 1H), 6.93 (s, 1H), 6.83 (s, 2H), 3.77 (s, 8H), 3.64 (s, 2H), 3.58 (t, J=4.2 Hz, 4H), 2.43 (t, J=4.2 Hz, 4H).

LC/MS (Method 1): Rt 2.062, [M+1]$^+$: 397.2

IC50 PI3Kα (μM): 0.080

Preparation of Compound 3-18

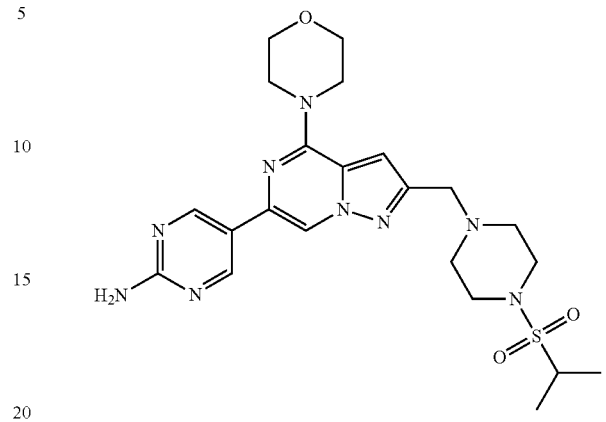

Following a similar procedure described for the synthesis of final product 3-10, afforded 5-{4-morpholin-4-yl-2-[4-(propane-2-sulfonyl)-piperazin-1-ylmethyl]-pyrazolo[1,5-a]pyrazin-6-yl}-pyrimidin-2-ylamine as a yellowish solid (29.3 mg, 66% yield in the last step).

$^1$H NMR (300 MHz, DMSO) δ 8.86 (s, 2H), 8.67 (s, 1H), 6.93 (s, 1H), 6.84 (s, 2H), 3.78 (s, 8H), 3.71 (s, 2H), 3.25 (s, 4H), 1.22 (d, J=6.2 Hz, 6H).

LC/MS (Method 1): Rt 2.549, [M+1]$^+$: 502.3

IC50 PI3Kα (μM): 0.006

Preparation of Compound 3-19

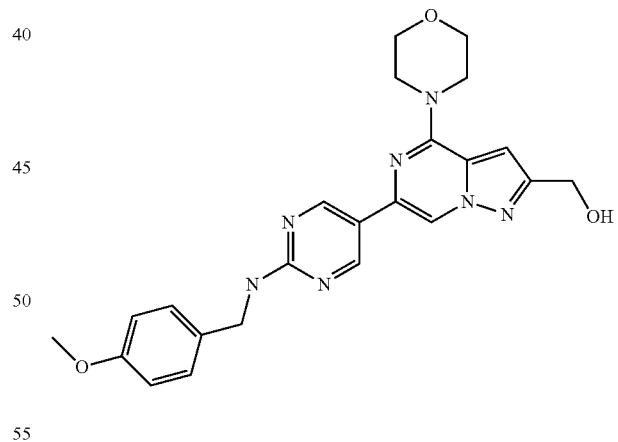

Following a similar procedure described for the synthesis of final product 3-10, afforded {6-[2-(4-methoxy-benzylamino)-pyrimidin-5-yl]-4-morpholin-4-yl-pyrazolo[1,5-a]pyrazin-2-yl}-methanol as a white solid (18 mg, 46% yield in the last step).

$^1$H NMR (300 MHz, DMSO) δ 8.91 (s, 2H), 8.64 (s, 1H), 7.89 (t, J=6.1 Hz, 1H), 7.25 (d, J=8.5 Hz, 2H), 6.92 (s, 1H), 6.86 (d, J=8.5 Hz, 2H), 5.32 (t, J=5.7 Hz, 1H), 4.63 (d, J=5.7 Hz, 2H), 4.47 (d, J=6.2 Hz, 2H), 3.77 (s, 8H), 3.71 (s, 3H).

LC/MS (Method 1): Rt 4.549, [M+1]$^+$: 448.3

Preparation of Compound 3-20

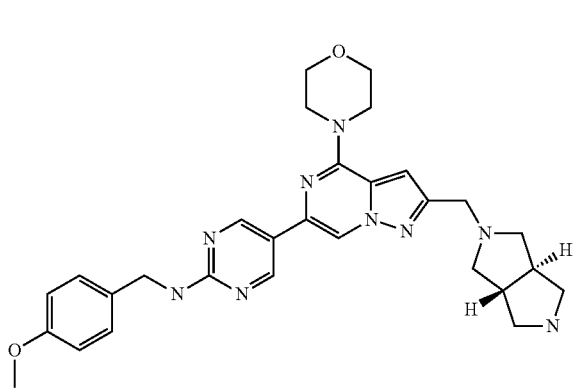 [SMILES: COc1ccc(CNc2ncc(-c3cn4nc(CN5C[C@H]6CNC[C@@H]6C5)cc4c(N4CCOCC4)n3)cn2)cc1]

Following a similar procedure described for the synthesis of final product 3-10, afforded (5-{2-[(3aS,6aR)-1-(hexahydro-pyrrolo[3,4-c]pyrrol-2-yl)methyl]-4-morpholin-4-yl-pyrazolo[1,5-a]pyrazin-6-yl}-pyridin-2-yl)-(4-methoxy-benzyl)-amine as a brown solid (13.9 mg, 29% yield in the last step).

$^1$H NMR (300 MHz, DMSO) 8.90 (s, 2H), 8.64 (s, 1H), 7.90 (q, J=6.0 Hz, 1H), 7.25 (d, J=8.5 Hz, 2H), 6.93 (s, 1H), 6.86 (d, J=8.5 Hz, 2H), 4.47 (d, J=6.2 Hz, 2H), 3.77 (s, 8H), 3.75 (s, 3H), 3.71 (s, 2H), 3.70 (s, 2H), 2.84 (d, J=11.6 Hz, 2H), 2.72 (s, 2H), 2.59 (m, 2H), 2.26 (t, J=20.2 Hz, 2H).

LC/MS (Method 1): Rt 2.661, [M+1]$^+$: 542.1

Preparation of Compound 3-21

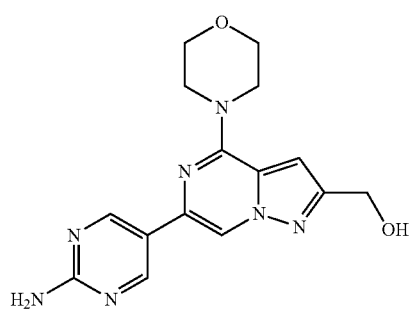 [SMILES: Nc1ncc(-c2cn3nc(CO)cc3c(N3CCOCC3)n2)cn1]

Following a similar procedure described for the synthesis of final product 3-10, deprotection of compound 3-19 (14.0 mg, 0.031 mmol) afforded, after purification of the crude reaction mixture by reverse column chromatography (water/MeCN mixtures as eluant) and then in Silicagel (EtOAc/MeOH 7:3 mixtures), desired compound 6-(2-amino-pyrimidin-5-yl)-4-morpholin-4-yl-pyrazolo[1,5-a]pyrazin-2-yl]-methanol (3-21) as a white solid solid (4.76 mg, 47% yield).

$^1$H NMR (DMSO, 300 MHz) δ 8.87 (s, 2H), 8.64 (s, 1H), 6.93 (s, 1H), 6.84 (s, 2H), 4.63 (s, 2H), 3.78 (s, 8H).

LC/MS (Method 2): Rt 2.907, [M+1]$^+$: 328.1

Preparation of Compound 3-21A

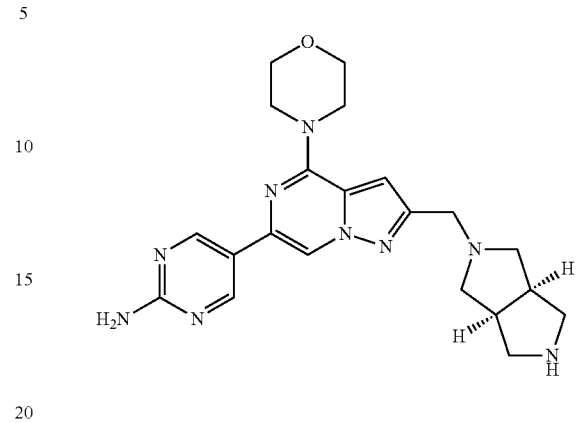

Following a similar procedure described for the synthesis of final product 3-10, deprotection of compound 3-20 (11.51 mg, 0.021 mmol) afforded 5-{2-[(3aS,6aR)-1-(hexahydro-pyrrolo[3,4-c]pyrrol-2-yl)methyl]-4-morpholin-4-yl-pyrazolo[1,5-a]pyrazin-6-yl}-pyrimidin-2-ylamine as a yellowish solid (8.7 mg, 97% yield) after purification of the crude reaction mixture by reverese column chromatography (water/MeCN mixtures as eluant).

$^1$H NMR (300 MHz, MeOD) 8.48 (s, 2H), 8.06 (s, 2H), 6.72 (s, 1H), 4.00 (s, 2H), 3.49 (s, 8H), 2.93 (m, 10H).

LC/MS (Method 2): Rt 0.479, [M+1]$^+$: 422.2

Preparation of Compound 3-22

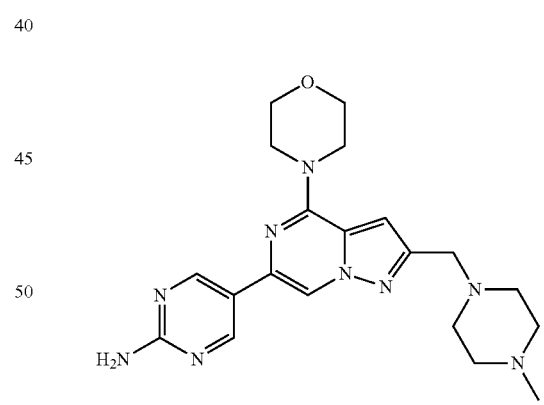

Following a similar procedure described for the synthesis of final product 3-10, afforded 5-[2-(4-Methyl-piperazin-1-ylmethyl)-4-morpholin-4-yl-pyrazolo[1,5-a]pyrazin-6-yl]-pyrimidin-2-ylamine as a white solid.

$^1$H NMR (300 MHz, DMSO) δ 8.71 (s, 2H), 8.51 (s, 1H), 6.76 (s, 1H), 6.69 (s, 2H), 3.62 (s, 8H), 3.48 (s, 2H), 2.28 (s, 2H), 2.16 (s, 2H), 1.99 (s, 3H).

LC/MS (Method 2): Rt 2.151, [M+1]$^+$: 410.2

Preparation of Compound 3-23

Following a similar procedure described for the synthesis of final product 3-10, afforded 5-(4-Morpholin-4-yl-2-piperazin-1-ylmethyl-pyrazolo[1,5-a]pyrazin-6-yl)-pyrimidin-2-ylamine as a white solid.

$^1$H NMR (300 MHz, DMSQ) δ 8.86 (s, 2H), 8.66 (s, 1H), 6.90 (s, 1H), 6.83 (s, 2H), 3.77 (s, 8H), 3.60 (s, 2H), 2.67 (s, 4H), 2.34 (s, 4H).

LC/MS (Method 2): Rt 2.045, [M+1]$^+$: 396.2

Example

Cellular Activity

Compounds of the examples/invention were tested in the PI3K signalling cellular assay described hereinbefore (Western Blot Analysis), which measures AKT phosphorylation inhibition. Cellular activity of representative compounds, is represented in the table below:

TABLE 5

| Compound | p-AKT (IC50, WB) |
|---|---|
| 2-3 | 12 nM |
| 2-4 | 64 nM |
| 3-10 | 14 nM |
| 3-9 | 5 nM |

Example

Combination Therapy

The individual measured $EC_{50}$ values against the particular cell of the exemplary compounds and of the chemotherapeutic agents are compared to the combination $EC_{50}$ value. The combination Index (CI) score is calculated by the Chou and Talalay method (CalcuSyn software, Biosoft). A CI less 0.8 indicates synergy. A CI between 0.8 and 1.2 indicates additivity. A CI greater than 1.2 indicates antagonism. These data are provided in Table 6 below.

Last column on Table 6 represents the CI, where (++++) represents a combination index lower than 0.1, (+++) represents a combination index greater than 0.1 but lower than 0.3, (++) represents a combination index greater than 0.3 but lower than 0.7, (+) represents a combination index greater than 0.7 but lower than 1.2, (−) represents a combination index greater than 1.2.

TABLE 6

In vitro cell proliferation assays of combination of Product No. 2-4 and various chemotherapeutics agents.

| Cell Line | Tumor Types | Gene mutation | Therapeutic (comp. (B)) | Chemot. $EC_{50}$ μM | Compound No. 2-4 (comp. (A)) $EC_{50}$ μM | Combination Index (CI) | Synergy |
|---|---|---|---|---|---|---|---|
| A549 | Lung | Ras G12S | PD-0325901 | 1 | 1 | 0.27 | +++ |
| A549 | Lung | Ras G12S | Lapatinib | 1 | 1 | 2.44 | − |
| SKVO3 | Ovarian | PIK3CA, p53 | Taxotere | 2 | 1 | | |
| HCT116 | Colon | Ras G13D/ PI3K H104 | PD-0325901 | | | | |
| HCT116 | Colon | Ras G13D/ PI3K H104 | Rapamycin | | | | |

The invention claimed is:
1. A compound of formula I,

I wherein:
A$_1$ represents N or C(R$^1$);
A$_4$ represents N or C(R$^{1a}$);
A$_{4a}$ represents N or C(R$^{1b}$);
wherein at least one of A$_4$ and A$_{4a}$ does not represent N;
A$_5$ represents N or C(R$^2$);
wherein when A$_4$, A$_{4a}$ and A$_5$ respectively represent C(R$^{1a}$), C(R$^{1b}$) and C(R$^2$), then A$_1$ does not represent N;
each B$^1$, B$^{1a}$, B$^2$, B$^{2a}$, B$^3$, B$^{3a}$, B$^4$ and B$^{4a}$ independently represent hydrogen or a substituent selected from halo, —C(=Y)—R$^{10a}$, —C(=Y)—OR$^{10a}$, —C(=Y)N(R$^{10a}$)R$^{11a}$, —S(O)$_2$N(R$^{10a}$)R$^{11a}$, C$_{1-12}$alkyl, heterocycloalkyl (which latter two groups are optionally substituted by one or more substituents selected from =O and E$^1$), aryl and/or heteroaryl (which latter two groups are optionally substituted by one or more substituents selected from E$^2$); or any two B$^1$, B$^{1a}$, B$^2$, B$^{2a}$, B$^3$, B$^{3a}$, B$^4$ and B$^{4a}$ substituents that are attached to the same carbon atom may together form a=O group;

or, any two B$^1$, B$^{1a}$, B$^2$, B$^{2a}$, B$^3$, B$^{3a}$, B$^4$ and B$^{4a}$ substituents may be linked together to form a further 3- to 12-membered ring, optionally containing (in addition to the atom(s) of the morpholine ring) one or more heteroatom(s), which ring optionally contains one or more double bonds, and which ring is itself optionally substituted by one or more substituents selected from halo, =O and C$_{1-3}$ alkyl optionally substituted by one or more fluoro atoms;

R$^1$ and R$^2$ independently represents hydrogen or a substituent selected from halo, —CN, —OR$^{10b}$, —N(R$^{10b}$)R$^{11b}$, —C(O)N(R$^{10b}$)R$^{11b}$, C$_{1-12}$ alkyl and heterocycloalkyl, which latter two groups are optionally substituted by one or more substituents selected from E$^3$ and =O;

R$^{1b}$ (when present) represents:
  (i) C$_{1-12}$ alkyl optionally substituted by one or more substituents selected from Q$^{1a}$;
  (ii) heterocycloalkyl (linked via a carbon atom) optionally substituted by one or more substituents selected from =O and Q$^{1b}$; or
  (iii) a fragment of formula IA;

R$^{1a}$ (when present) represents:
  (i) hydrogen;
  (ii) Q$^1$;
  (iii) C$_{1-12}$ alkyl optionally substituted by one or more substituents selected from =O, =S, =N(R$^{10a}$) and Q$^2$; or
  (iv) a fragment of formula IA;

the fragment of formula IA represents:

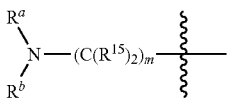

IA wherein:
m represents 1, 2, 3, 4, 5 or 6;
each R$^{15}$ represents hydrogen, halo or C$_{1-6}$ alkyl optionally substituted by one or more substituents selected from E$^4$; or
the two R$^{15}$ groups may be linked together to form (along with the requisite carbon atom to which those R$^{15}$ groups are necessarily attached) a 3- to 6-membered (spirocyclic) ring, which ring optionally contains one or more double bonds, and optionally contains a further heteroatom selected from nitrogen, sulfur and oxygen, and which ring is optionally substituted by one or more substituents selected from E$^5$;
R$^a$ and R$^b$ are linked together, along with the requisite nitrogen atom to which they are necessarily attached, to form a first 3- to 7-membered cyclic group, optionally containing one further heteroatom selected from nitrogen, sulfur and oxygen, and which ring:
  (a) is fused to a second ring that is either a 3- to 7-membered saturated heterocycloalkyl group containing one to four heteroatoms selected from oxygen, sulfur and nitrogen, a 3- to 12-membered saturated carbocyclic ring, or an unsaturated 5- to 12-membered carbocyclic or heterocyclic ring;
  (b) comprises a linker group —(C(R$^x$)$_2$)$_p$— and/or —(C(R$^x$)$_2$)$_r$—O—(C(R$^x$)$_2$)$_s$— (wherein p is 1 or 2; r is 0 or 1; s is 0 or 1; and each R$^x$ independently represents hydrogen or C$_{1-6}$ alkyl), linking together any two non-adjacent atoms of the first 3- to 7-membered ring; or
  (c) comprises a second ring that is either a 3- to 12-membered saturated carbocyclic ring or a 3- to 7-membered saturated heterocycloalkyl group containing one to four heteroatoms selected from oxygen and nitrogen, and which second ring is linked together with the first ring via a single carbon atom common to both rings,
all of which cyclic groups, defined by the linkage of R$^a$ and R$^b$, are optionally substituted by one or more substituents selected from =O, =NOR$^{1a}$ and E$^6$;
R$^3$ represents aryl or heteroaryl (both of which are optionally substituted by one or more substituents selected from E$^7$);
each Q$^{1a}$, Q$^{1b}$, Q$^1$ and Q$^2$ independently represents, on each occasion when used herein: halo, —CN, —NO$_2$, —N(R$^{10a}$)R$^{11a}$, —OR$^{10a}$, —C(=Y)—R$^{10a}$, —C(=Y)—OR$^{10a}$, —C(=Y)N(R$^{10a}$)R$^{11a}$, —C(=Y)N(R$^{10a}$)—OR$^{11c}$, —OC(=Y)—R$^{10a}$, —OC(=Y)—OR$^{11a}$, —OC(=Y)N(R$^{10a}$)R$^{11a}$, —OS(O)$_2$OR$^{10a}$, —OP(=Y)(OR$^{10a}$)(OR$^{11a}$), —OP(OR$^{10a}$)(OR$^{11a}$), —N(R$^{12a}$)C(=Y)R$^{11a}$, —N(R$^{12a}$)C(=Y)OR$^{11a}$, —N(R$^{12a}$)C(=Y)N(R$^{10a}$)R$^{11a}$, —NR$^{12a}$S(O)$_2$R$^{10a}$, —NR$^{12a}$S(O)$_2$N(R$^{10a}$)R$^{11a}$, —S(O)$_2$N (R$^{10a}$)R$^{11a}$, —SC(=Y)R$_{10a}$, —S(O)$_2$R$^{10a}$, —SR$^{10a}$, —S(O)R$^{10a}$, C$_{1-12}$ alkyl, heterocycloalkyl (which latter two groups are optionally substituted by one or more substituents selected from =O, =S, =N(R$^{10a}$) and E$^8$), aryl or heteroaryl (which latter two groups are optionally substituted by one or more substituents selected from E$^9$);
each R$^{11c}$ independently represents C$_{1-12}$ alkyl, heterocycloalkyl (which latter two groups are optionally substituted by one or more substituents selected from =O, =S, =N(R$^{20}$) and E$^{10}$), aryl or heteroaryl (which latter two groups are optionally substituted by one or more substituents selected from E$^{11}$);
each R$^{10a}$, R$^{11a}$, R$^{10b}$, R$^{11b}$ and R$^{12a}$ independently represent, on each occasion when used herein, hydrogen, C$_{1-12}$ alkyl, heterocycloalkyl (which latter two groups are optionally substituted by one or more substituents selected from =O, =S, =N(R$^{20}$) and E$^{10}$), aryl or heteroaryl (which latter two groups are optionally substituted by one or more substituents selected from E$^{11}$); or
any relevant pair of R$^{10a}$ and R$^{11a}$ or R$^{10b}$ and R$^{11b}$ may be linked together to form a 4- to 20-membered ring, optionally containing one or more heteroatoms, optionally containing one or more unsaturations, and which ring is optionally substituted by one or more substituents selected from =O, =S, =N(R$^{20}$) and E$^{12}$;
each E$^1$, E$^2$, E$^3$, E$^4$, E$^5$, E$^6$, E$^7$, E$^8$, E$^9$, E$^{10}$, E$^{11}$ and E$^{12}$ independently represents, on each occasion when used herein:
  (i) Q$^4$;
  (ii) C$_{1-12}$ alkyl optionally substituted by one or more substituents selected from =O and Q$^5$; or
any two E$^1$, E$^2$, E$^3$, E$^4$, E$^5$, E$^6$, E$^7$, E$^8$, E$^9$, E$^{10}$, E$^{11}$ and E$^{12}$ groups may be linked together to form a 3- to 12-membered ring, optionally containing one or more unsaturations, and which ring is optionally substituted by one or more substituents selected from =O and J$^1$;

each $Q^4$ and $Q^5$ independently represent, on each occasion when used herein: halo, —CN, —NO$_2$, —N(R$^{20}$)R$^{21}$, —OR$^{20}$, —C(=Y)—R$^{20}$, —C(=Y)—OR$^{20}$, —C(=Y)N(R$^{20}$)R$^{21}$, —C(=Y)N(R$^{20}$)—O—R$^{21a}$, —OC(=Y)—R$^{20}$, —OC(=Y)—OR$^{20}$, —OC(=Y)N(R$^{20}$)R$^{21}$, —OS(O)$_2$OR$^{20}$, —OP(=Y)(OR$^{20}$)(OR$^{21}$), —OP(OR$^{20}$)(OR$^{21}$), —N(R$^{22}$)C(=Y)R$^{21}$, —N(R$^{22}$)C(=Y)OR$^{21}$, —N(R$^{22}$)C(=Y)N(R$^{20}$)R$^{21}$, —NR$^{22}$S(O)$_2$R$^{20}$), —NR$^{22}$S(O)$_2$N(R$^{20}$)R$^{21}$, —S(O)$_2$N(R$^{20}$)R$^{21}$, —SC(=Y)R$^{20}$, —S(O)$_2$R$^{20}$, —SR$^{20}$, —S(O)R$^{20}$, C$_{1-6}$ alkyl, heterocycloalkyl (which latter two groups are optionally substituted by one or more substituents selected from =O and J$^2$), aryl or heteroaryl (which latter two groups are optionally substituted by one or more substituents selected from J$^3$);

each Y independently represents, on each occasion when used herein, =O, =S, =NR$^{23}$ or =N—CN;

each R$^{21a}$ represents C$_{1-6}$ alkyl, heterocycloalkyl (which latter two groups are optionally substituted by one or more substituents selected from J$^4$ and =O), aryl or heteroaryl (which latter two groups are optionally substituted by one or more substituents selected from J$^5$);

each R$^{20}$, R$^{21}$, R$^{22}$ and R$^{23}$ independently represent, on each occasion when used herein, hydrogen, C$_{1-6}$ alkyl, heterocycloalkyl (which latter two groups are optionally substituted by one or more substituents selected from J$^4$ and =O), aryl or heteroaryl (which latter two groups are optionally substituted by one or more substituents selected from J$^5$); or any relevant pair of R$^{20}$, R$^{21}$ and R$^{22}$, may be linked together to form a 4- to 20-membered ring, optionally containing one or more heteroatoms, optionally containing one or more unsaturations, and which ring is optionally substituted by one or more substituents selected from J$^6$ and =O;

each J$^1$, J$^2$, J$^3$, J$^4$, J$^5$ and J$^6$ independently represents, on each occasion when used herein:
(i) Q$^7$;
(ii) C$_{1-6}$ alkyl or heterocycloalkyl, both of which are optionally substituted by one or more substituents selected from =O and Q$^8$;

each Q$^7$ and Q$^8$ independently represents, on each occasion when used herein:
halo, —CN, —N(R$^{50}$)R$^{51}$, —OR$^{50}$, —C(=Y$^a$)—R$^{50}$, —C(=Y$^a$)—OR$^{50}$), —C(=Y$^a$)N(R$^{50}$)R$^{51}$, —N(R$^{52}$)C(=Y$^a$)R$^{51}$, —NR$^{52}$S(O)$_2$R$^{50}$, —S(O)$_2$N(R$^{50}$)R$^{51}$, —N(R$^{52}$)—C(=Y$^a$)—N(R$^{50}$)R$^{51}$, —S(O)$_2$R$^{50}$, —SR$^{50}$, —S(O)R$^{50}$, C$_{1-6}$ alkyl (optionally substituted by one or more fluoro atoms), heterocyclalkyl, aryl or heteroaryl (which latter three groups are optionally substituted by one or more substituents selected from halo, —OR$^{60}$ and —N(R$^{61}$)R$^{62}$);

each Y$^a$ independently represents, on each occasion when used herein, =O, =S, =NR$^{53}$ or =N—CN;

each R$^{50}$, R$^{51}$, R$^{52}$ and R$^{53}$ independently represents, on each occasion when used herein, hydrogen or C$_{1-6}$ alkyl optionally substituted by one or more substituents selected from fluoro, —OR$^{60}$ and —N(R$^{61}$)R$^{62}$; or any relevant pair of R$^{50}$, R$^{51}$ and R$^{52}$ may be linked together to form, a 3- to 8-membered ring, optionally containing one or more heteroatoms, optionally containing one or more unsaturations, and which ring is optionally substituted by one or more substituents selected from =O and C$_{1-3}$ alkyl;

each R$^{60}$, R$^{61}$ and R$^{62}$ independently represent hydrogen or C$_{1-6}$ alkyl optionally substituted by one or more fluoro atoms, or a pharmaceutically acceptable ester, amide, solvate or salt thereof.

2. A compound as claimed in claim 1, wherein the requisite bicyclic core (containing A$_1$, A$_4$, A$_{4a}$ and A$_5$) represents anyone of the following:

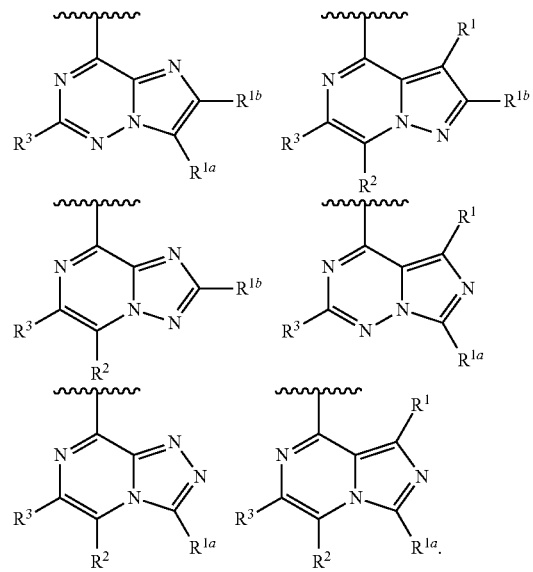

3. A compound as claimed in claim 1, wherein: R$^{1b}$ (when present) represents: (i) a fragment of formula IA; (ii) C$_{1-12}$ alkyl optionally substituted by one or more substituents selected from Q$^{1a}$; or (iii) heterocycloalkyl (linked to the requisite bicycle of formula I via a carbon atom) optionally substituted by one or more substituents selected from =O and Q$^{1b}$; R$^{1a}$ represents hydrogen, C$_{1-12}$ alkyl optionally substituted by one or more substituents selected from =S, =N(R$^{10a}$), =O and Q$^2$; Q$^1$ (when present) represents —C(=Y)N(R$^{10a}$)R$^{11a}$; Q$^{1a}$ and Q$^2$ independently represent —OR$^{10a}$, —N(R$^{10a}$)R$^{11a}$ or heterocycloalkyl, which is optionally substituted by one or more substituent selected from E$^8$; Q$^{1b}$ represents halo, —CN, —OR$^{10a}$ or —N(R$^{10a}$)R$^{11a}$; R$^{15}$ represents hydrogen; m represents 1; R$^a$ and R$^b$ are linked together to form a 5- or 6-membered ring fused to another 5- or 6-membered ring; R$^2$ represents hydrogen or halo; R$^3$ represents aryl or heteroaryl both of which are optionally substituted by one or more substituent(s) selected from E$^7$; E$^1$ to E$^{12}$ independently represent C$_{1-6}$ alkyl optionally substituted by one or more Q$^5$ substituents, or E$^1$ to E$^{12}$ represent Q$^4$; Q$^4$ represents —OR$^{20}$, —N(R$^{20}$)R$^{21}$, —S(O)$_2$R$^{20}$, heterocycloalkyl, aryl or heteroaryl; Q$^5$ represents halo; and/or Y represents =O.

4. A compound as claimed in claim 1, wherein: R$^{20}$ and R$^{21}$ independently represent hydrogen, C$_{1-3}$ alkyl, which latter group is optionally substituted by one or) more substituent(s) selected from J$^4$; when there is a —N(R$^{20}$)R$^{21}$ moiety present, then one of R$^{20}$ and R$^{21}$ represents hydrogen, and the other represents hydrogen, C$_{1-3}$ alkyl, which latter group is optionally substituted by one or more substituent(s) selected from J$^4$; J$^3$ represents Q$^7$; J$^4$ represents Q$^7$ or C$_{1-6}$ alkyl; Q$^7$ represents aryl (optionally substituted by —OR$^{60}$) or —S(O)$_2$R$^{50}$; and/or R$^{50}$ and R$^{60}$ independently represent C$_{1-3}$ alkyl.

5. A compound as claimed in claim 1, wherein: R$^2$ represents hydrogen or chloro; R$^3$ represents hydroxyphenyl, methoxyphenyl, indazolyl, pyrimidinyl, azaindolyl, indolyl, pyridyl; and/or $B^1$, $B^{1a}$, $B^2$, $B^{2a}$, $B^3$, $B^{3a}$, $B^4$ and $B^{4a}$ independently represent hydrogen.

6. A pharmaceutical formulation comprising a compound of formula I, as defined in claim 1, or a pharmaceutically acceptable ester, amide, solvate or salt thereof, in admixture with a pharmaceutically acceptable adjuvant, diluent or carrier.

7. A combination product comprising:
(A) a compound of formula I as defined in claim 1, or a pharmaceutically-acceptable ester, amide, solvate or salt thereof; and
(B) another therapeutic agent that is useful in the treatment of cancer and/or a proliferative disease,
wherein each of components (A) and (B) is formulated in admixture with a pharmaceutically-acceptable adjuvant, diluent or carrier.

8. A process for the preparation of a compound of formula I as defined in claim 1, which process comprises:
(i) reaction of a compound of formula II,

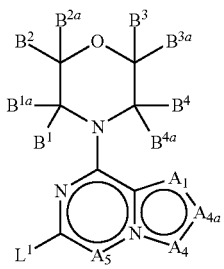

II wherein $L^1$ represents a suitable leaving group, and $A_1$, $A_4$, $A_{4a}$, $A_5$, $B^1$, $B^{1a}$, $B^2$, $B^{2a}$, $B^3$, $B^{3a}$, $B^4$ and $B^{4a}$ as defined in claim 1, with a compound of formula III, $$R^3\text{-}L^2 \quad \text{III}$$

wherein $R^3$ is as defined in claim 1; $L^2$ represents a suitable group;
(ii) reaction of a compound of formula IV,

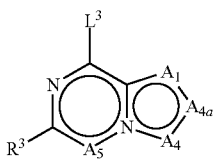

IV wherein $L^3$ represents a suitable leaving group, and $A_1$, $A_4$, $A_{4a}$, $A_5$ and $R^3$ as defined in claim 1, with a compound of formula V,

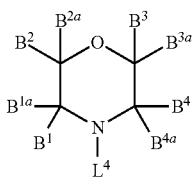

V wherein $L^4$ may represent hydrogen (so forming an amine group), and $B^1$, $B^{1a}$, $B^2$, $B^{2a}$, $B^3$, $B^{3a}$, $B^4$ and $B^{4a}$ are as defined in claim 1;
(iii) for compounds of formula I in which ($A^5$ represents $C(R^2)$) and $R^2$ represents halo, reaction of a corresponding compound of formula I, in which $R^2$ represents hydrogen, with a reagent that is a source of halide ions (a halogenating reagent);
(iv) for compounds of formula I in which $R^2$ (if present) represents a substituent other that than hydrogen, or halo, reaction of a corresponding compound of formula I, in which $R^2$ represents halo, with a compound of formula VI, $$R^{2a}\text{-}L^7 \quad \text{VI}$$

wherein $R^{2a}$ represents $R^2$ as described in claim 1 provided that it does not represent hydrogen or halo, and $L^7$ represents a suitable leaving group;
(v) for compounds of formula I in which $A^{4a}$ represents $C(R^{1b})$ and $R^{1b}$ represents $C_{1-12}$ alkyl or heterocycloalkyl (which latter two groups are optionally substituted as defined in claim 1) or $R^{1a}$ is present, which represents —$C(O)OR^{10a}$, halo, $C_{1-12}$ alkyl or heterocycloalkyl (which latter two groups are optionally substituted as defined in claim 1) may be prepared from corresponding compounds of formula I in which $R^{1a}$ or $R^{1b}$ (as appropriate) represents hydrogen, by reaction in the presence of a suitable base, followed by reaction in the presence of an electrophile that is a source of halide ions, or a compound of formula VII, $$L^8\text{-}R^{1b1} \quad \text{VII}$$

$L^8$ represents a suitable leaving group, or —$N(CH_3)_2$, and $R^{1b1}$ represents —$C(O)OR^{10a}$, $C_{1-12}$ alkyl or heterocycloalkyl (which latter two groups are optionally substituted by one or more substituents defined in claim 1; $R^{11a}$ is as defined in claim 1;
(vi) for compounds of formula I which contain a —$C(OH)(H)$—$C_{1-11}$ alkyl group (which alkyl group may be substituted by one or more substituents selected from those defined in claim 1), for example when there is a $R^1$, $R^{1a}$, $R^{1b}$ and/or $R^2$ group present which represents such a —$C(OH)(H)$—$C_{1-11}$ alkyl group, reaction of a corresponding compound of formula I in which there is a —$C(O)H$ group present, with a compound of formula VIII, $$R^{xx}MgX^1 \quad \text{VIII}$$

wherein $R^{xx}$ represents $C_{1-11}$ alkyl optionally substituted by one or more substituents selected from those defined in claim 1 and $X^1$ represents halo;
(vii) compounds of formula I in which $A_1$ and $A_4$ both represent N, $A_5$ represents $C(R^2)$ and $A_{4a}$ represents $C(R^{1b})$ may be prepared by reaction of a compound of formula IX,

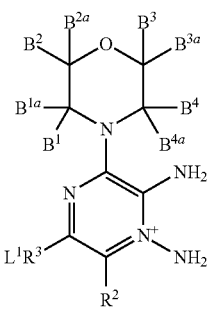

IX wherein $L^1R^3$ represents either $L^1$ as defined above or $R^3$ as defined in claim 1, and $R^2$, $B^1$, $B^{1a}$, $B^2$, $B^{2a}$, $B^3$, $B^{3a}$, $B^4$ and $B^{4a}$ are as defined in claim 1, with a compound of formula X, $$H\text{—}C(O)\text{—}R^{1b} \quad \text{X}$$

wherein $R^{1b}$ is as defined in claim 1, and, when $L^1R^3$ in the compound of formula IX represents $L^1$, then this process step may be proceeded by process step (i) as defined above;
(viii) compounds of formula I in which $A_1$ represents N, $A_4$ represents $C(R^{1a})$, $A_{4a}$ represents N and $A_5$ represents $C(R^2)$ may also be prepared by reaction of a compound of formula XI,

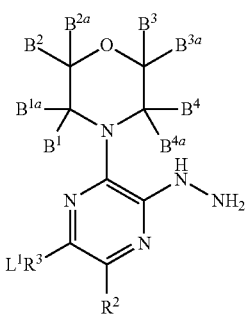

wherein L¹R³ is as defined above and R², B¹, B¹ᵃ, B², B²ᵃ, B³, B³ᵃ, B⁴ and B⁴ᵃ are as defined in claim 1, with a compound of formula XII, $$R^{1a}\text{—}C(OC_{1\text{-}6}\text{ alkyl})_3 \qquad \text{XII}$$

or, a compound of formula XIII, $$R^{1a}\text{—}C(O)OH \qquad \text{XIII}$$

wherein R¹ᵃ is as defined in claim 1 and when L¹R³ in the compound of formula XI represents L¹, then this process step may be proceeded by process step (i) as defined above.

9. A process for the preparation of a pharmaceutical formulation comprising a compound of formula I, as defined in claim 1, or a pharmaceutically acceptable ester, amide, solvate or salt thereof, in admixture with a pharmaceutically acceptable adjuvant, diluent or carrier, which process comprises bringing into association a compound of formula I, as defined in claim 1, or a pharmaceutically acceptable ester, amide, solvate or salt thereof with a pharmaceutically-acceptable adjuvant, diluent or carrier.

10. A process for the preparation of a combination product comprising
   (A) a compound of formula I as defined in claim 1, or a pharmaceutically-acceptable ester, amide, solvate or salt thereof; and
   (B) another therapeutic agent that is useful in the treatment of cancer and/or a proliferative disease,
wherein each of components (A) and (B) is formulated in admixture with a pharmaceutically-acceptable adjuvant, diluent or carrier, which process comprises bringing into association a compound of formula I, as defined in claim 1, or a pharmaceutically acceptable ester, amide, solvate or salt thereof with the other therapeutic agent that is useful in the treatment of cancer and/or a proliferative disease, and at least one pharmaceutically-acceptable adjuvant, diluent or carrier.

11. A compound having the structure:

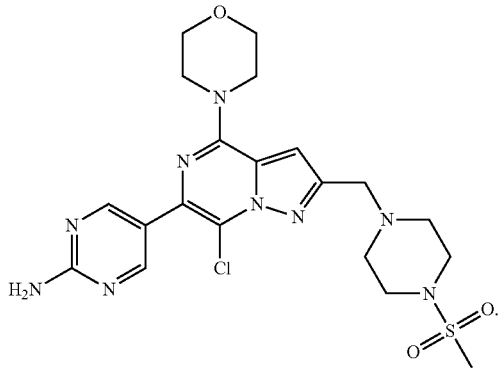

12. A compound as claimed in claim 1, wherein E⁹ represents Q⁴ or C₁₋₆ alkyl optionally substituted by one or more Q⁵ substituents.

13. A compound as claimed in claim 1, wherein each Q¹ᵃ, Q¹ᵇ, Q¹ and Q² independently represents, on each occasion when used herein:

halo, —CN, —NO₂, —N(R¹⁰ᵃ)R¹¹ᵃ, —OR¹⁰ᵃ, —C(=Y)—R¹⁰ᵃ, —C(=Y)—OR¹⁰ᵃ, —C(=Y)N(R¹⁰ᵃ)R¹¹ᵃ, —C(=Y)N(R¹⁰ᵃ)—OR¹¹ᶜ, —OC(=Y)—R¹⁰ᵃ, —OC(=Y)—OR¹⁰ᵃ, —OC(=Y)N(R¹⁰ᵃ)R¹¹ᵃ, —OS(O)₂OR¹⁰ᵃ, —OP(=Y)(OR¹⁰ᵃ)(OR¹¹ᵃ), —OP(OR¹⁰ᵃ)(OR¹¹ᵃ), —N(R¹²ᵃ)C(=Y)R¹¹ᵃ, —N(R¹²ᵃ)C(=Y)OR¹¹ᵃ, —N(R¹²ᵃ)C(=Y)N(R¹⁰ᵃ)R¹¹ᵃ, —NR¹²ᵃS(O)₂R¹⁰ᵃ, —NR¹²ᵃS(O)₂N(R¹⁰ᵃ)R¹¹ᵃ, —S(O)₂N(R¹⁰ᵃ)R¹¹ᵃ, —SC(=Y)R¹⁰ᵃ, —S(O)₂R¹⁰ᵃ, —SR¹⁰ᵃ, —S(O)R¹⁰ᵃ, C₁₋₁₂ alkyl, heterocycloalkyl (which latter two groups are optionally substituted by one or more substituents selected from =O, =S, =N(R¹⁰ᵃ) and E⁸), aryl or heteroaryl.

14. A compound as claimed in claim 1, wherein E¹ to E¹² independently represent Q⁴ or C₁₋₆ alkyl optionally substituted by one or more Q⁵ substituents.

15. A compound as claimed in claim 1, wherein the compound is selected from the group consisting of:

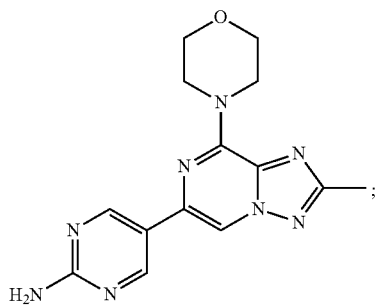

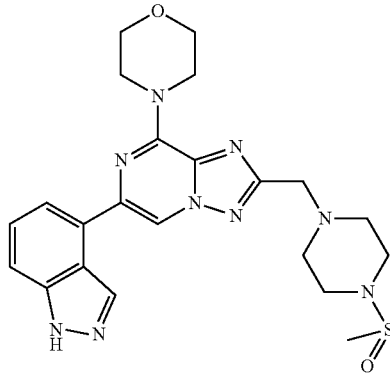

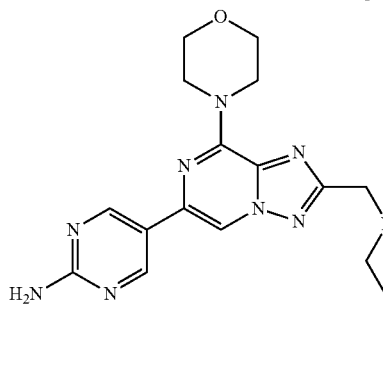

123
-continued
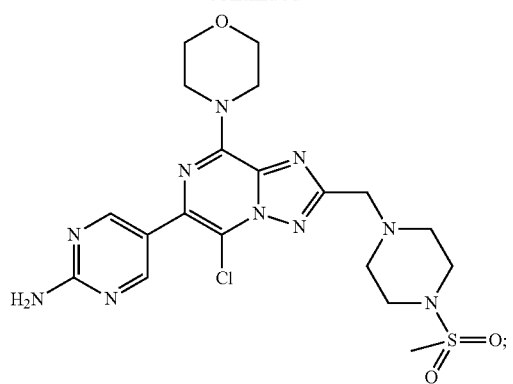
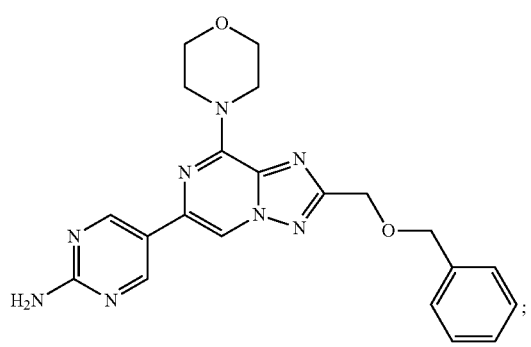
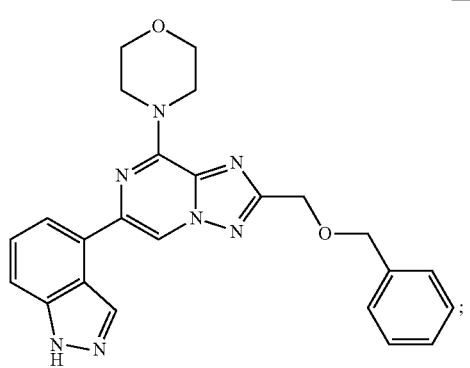
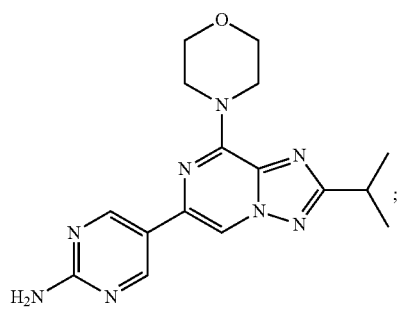
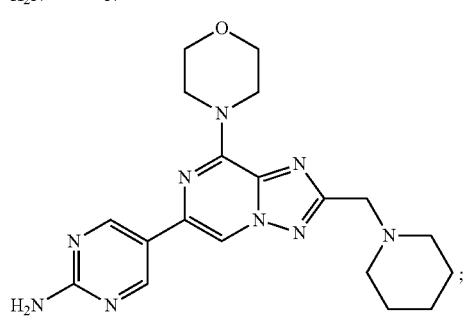
124
-continued
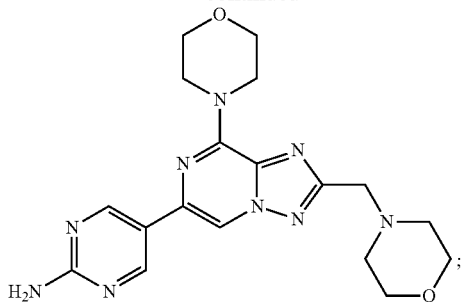
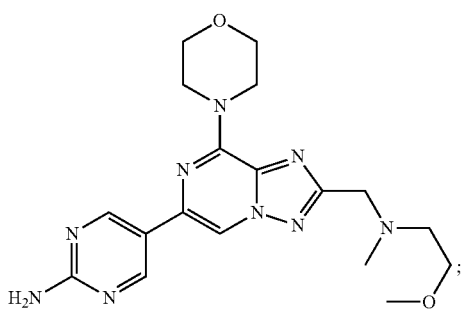
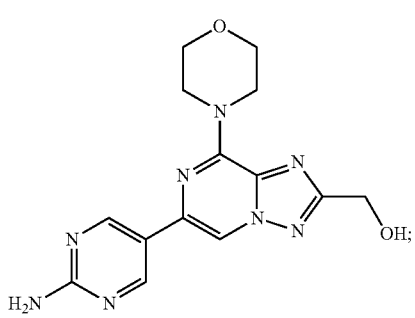
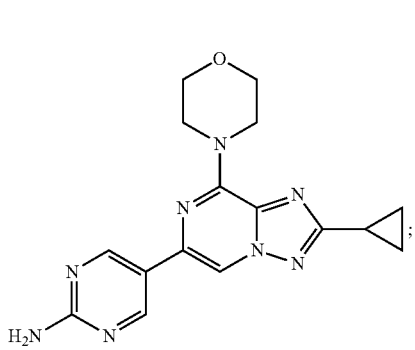
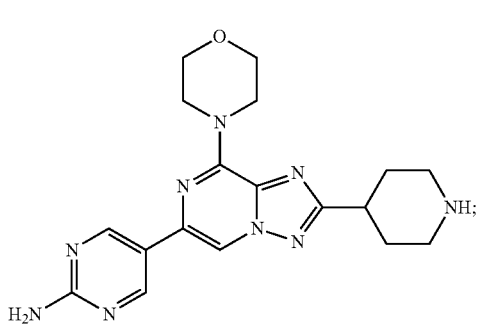

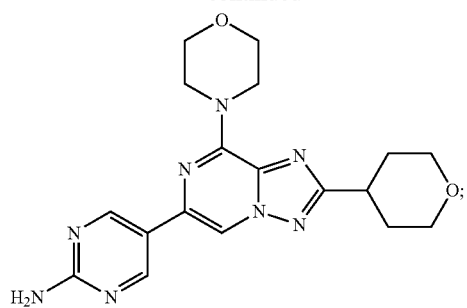
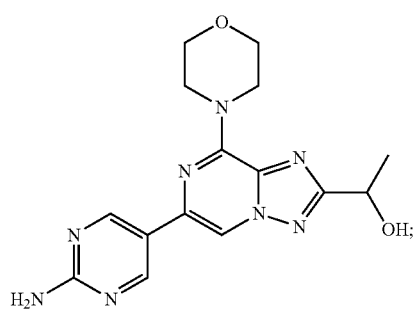
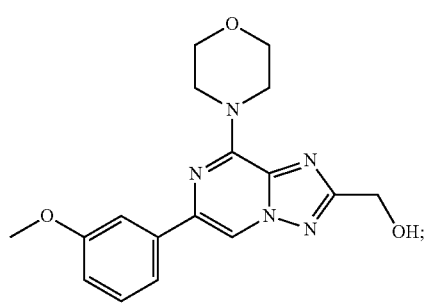
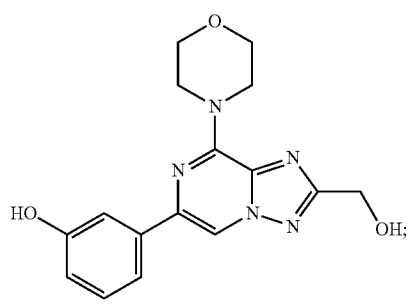
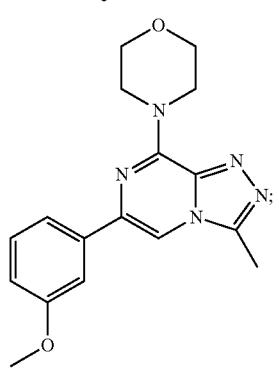
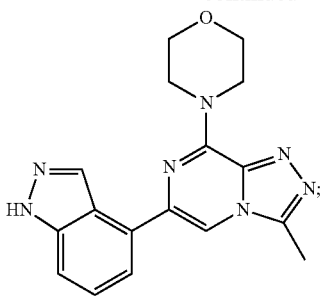
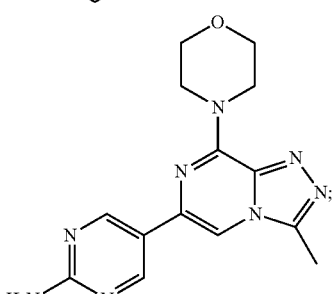
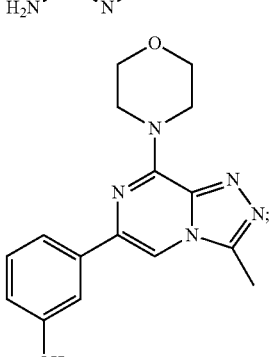
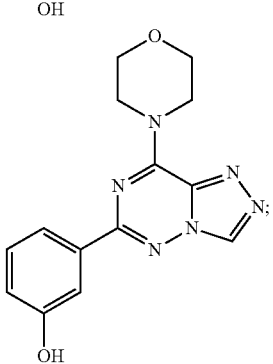
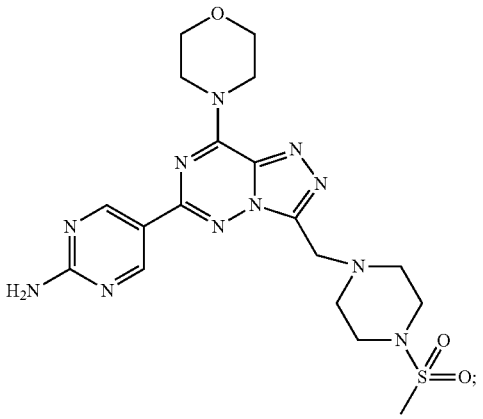

-continued

-continued
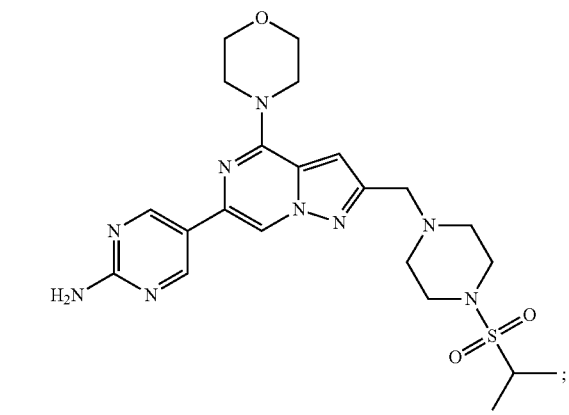
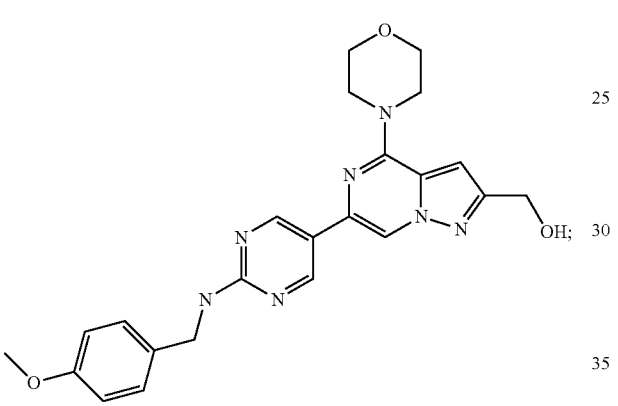
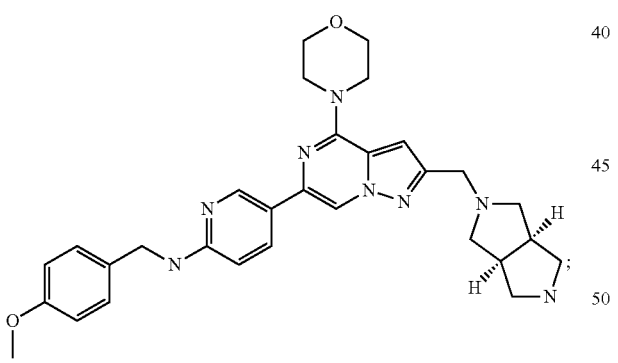
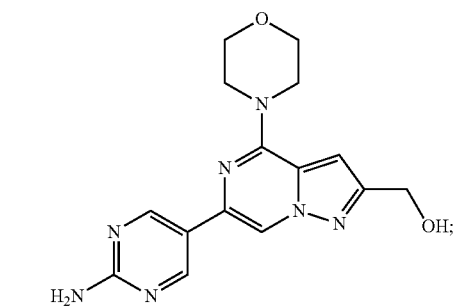
-continued
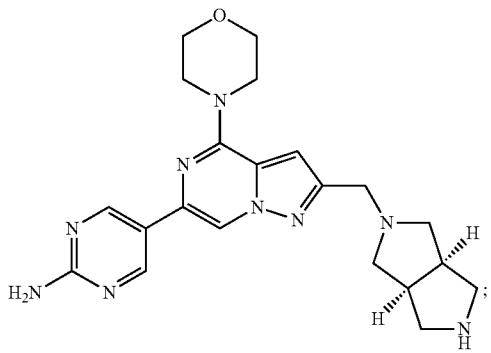 [SMILES: Nc1ncc(-c2cn3nc(CN4C[C@H]5CNC[C@H]5C4)cc3c(N3CCOCC3)n2)cn1]
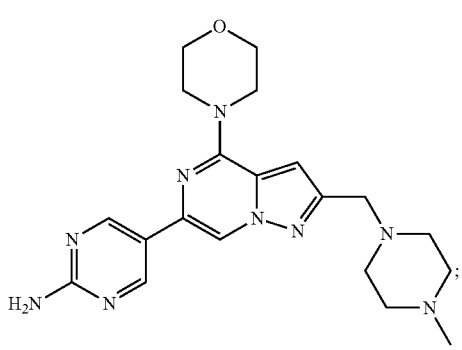
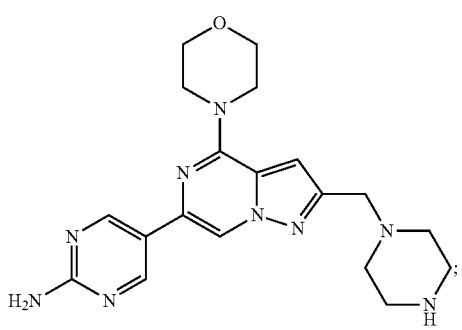
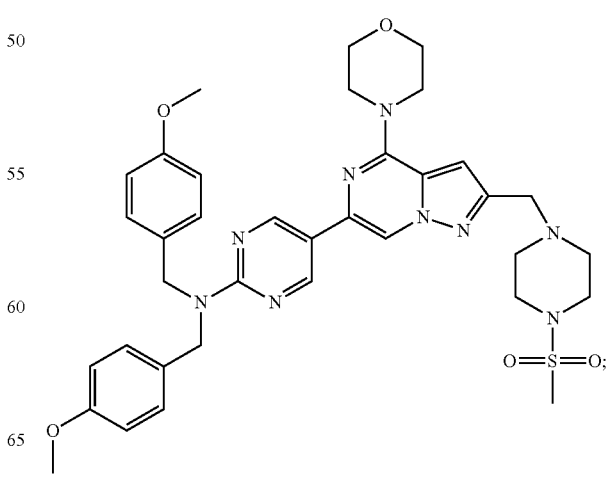

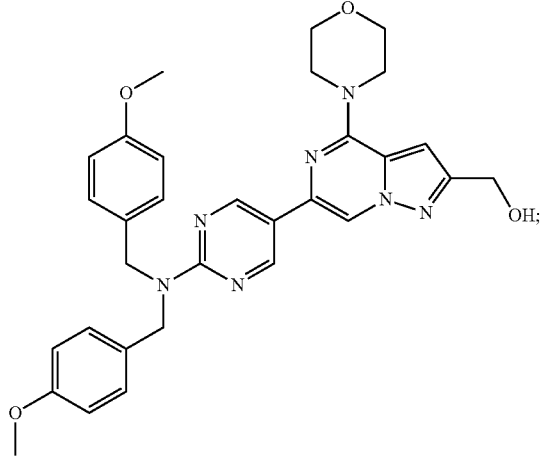
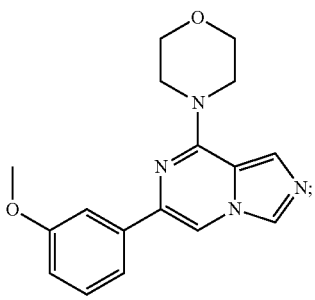
and pharmaceutically acceptable esters, amides, solvates or salts thereof.
* * * * *